US011298396B2

(12) United States Patent
Furukawa

(10) Patent No.: US 11,298,396 B2
(45) Date of Patent: Apr. 12, 2022

(54) AGENT FOR INHIBITING OR REDUCING LIGHT SENSITIVITY

(71) Applicant: Osaka University, Osaka (JP)

(72) Inventor: Takahisa Furukawa, Osaka (JP)

(73) Assignee: Osaka University, Osaka (JP)

( * ) Notice: Subject to any disclaimer, the term of this patent is extended or adjusted under 35 U.S.C. 154(b) by 0 days.

(21) Appl. No.: 16/494,464

(22) PCT Filed: Mar. 16, 2018

(86) PCT No.: PCT/JP2018/010660
§ 371 (c)(1),
(2) Date: Sep. 16, 2019

(87) PCT Pub. No.: WO2018/169090
PCT Pub. Date: Sep. 20, 2018

(65) Prior Publication Data

US 2020/0016229 A1 Jan. 16, 2020

(30) Foreign Application Priority Data

Mar. 17, 2017 (JP) ............................ JP2017-053811
Dec. 25, 2017 (JP) ............................ JP2017-248490

(51) Int. Cl.
*A61K 38/00* (2006.01)
*A61P 27/02* (2006.01)
*A61K 9/00* (2006.01)
*G01N 33/50* (2006.01)

(52) U.S. Cl.
CPC .......... *A61K 38/005* (2013.01); *A61K 9/0048* (2013.01); *A61P 27/02* (2018.01); *G01N 33/502* (2013.01)

(58) Field of Classification Search
None
See application file for complete search history.

(56) References Cited

U.S. PATENT DOCUMENTS

2004/0235733 A1 11/2004 Steffan et al.
2011/0268705 A1 11/2011 Cepko et al.
2013/0115619 A1 5/2013 Clark

FOREIGN PATENT DOCUMENTS

WO WO 2010/019786 A1 2/2010

OTHER PUBLICATIONS

Hadziahmetovic et al. ("Age-related Macular Degeneration Revisted: From Pathology and Cellular Stress to Potential Therapies" Front. Cell Dev. Biol. Jan. 2021).*

Chaya, Taro et al., "Cul3-Klhl18 ubiquitin ligase modulates rod transducin translocation during light-dark adaptation" The EMBO Journal, Dec. 2019, pp. 1-22, vol. 38, No. 23.

Kaewkhaw, Rossukon et al., "Transcriptome Dynamics of Developing Photoreceptors in Three-Dimensional Retina Cultures Recapitulates Temporal Sequence of Human Cone and Rod Differentiation Revealing Cell Surface Markers and Gene Networks" Stem Cells, Dec. 2015, pp. 3504-3518, vol. 33, No. 12.

Supplementary European Search Report for EP 18766987 dated Feb. 13, 2020.

Endo, Tomoyuki et al., "The Screening for the Ubiquitination Targets of KLHL7, a Retinitis Pigmentosa Causative Gene Product" Tsukuba Journal of Biology, 2014, p. 85, vol. 13, No. 1.

Fujiyama-Nakamura, Sally et al., "BTB protein, dKLHL18/CG3571, serves as an adaptor subunit for a dCul3 ubiquitin ligase complex" Genes to Cells, 2009, pp. 965-973, vol. 14.

Hu, Longqin et al., "Discovery of a small-molecule inhibitor and cellular probe of Keap1-Nrf2 protein-protein interaction" Bioorganic & Medicinal Chemistry Letters, 2013, pp. 3039-3043, vol. 23.

Jeong, Joo-Won et al., "Regulation and Destabilization of HIF-1α by ARD1-Mediated Acetylation" Cell, Nov. 2002, pp. 709-720, vol. 111.

Kigoshi, Yu et al., "Ubiquitin Ligase Activity of Cul3-KLHL7 Protein Is Attenuated by Autosomal Dominant Retinitis Pigmentosa Causative Mutation" The Journal of Biological Chemistry, Sep. 2011, pp. 33613-33621, vol. 286, No. 38.

Lu, Meng-Chen et al., "An inhibitor of the Keap1-Nrf2 protein-protein interaction protects NCM460 colonic cells and alleviates experimental colitis" Scientific Reports, 2016, pp. 1-13, vol. 6.

Moghe, Saili et al., "The CUL3-KLHL18 ligase regulates mitotic entry and ubiquitylates Aurora-A" Biology Open, 2011, pp. 82-91, vol. 1.

Obin, Martin S. et al., "Ubiquitinylation and Ubiquitin-dependent Proteolysis in Vertebrate Photoreceptors (Rod Outer Segments)" The Journal of Biological Chemistry, Jun. 1996, pp. 14473-14484, vol. 271, No. 24.

Omori, Yoshihiro et al., "Analysis of Transcriptional Regulatory Pathways of Photoreceptor Genes by Expression Profiling of the Otx2-Deficient Retina" PLoS ONE, May 2011, pp. 1-12, vol. 6, Issue 5, e19685.

Winkel, Angelika F. et al., "Characterization of RA839, a Noncovalent Small Molecule Binder to Keap1 and Selective Activator of Nrf2 Signaling" The Journal of Biological Chemistry, Nov. 2015, pp. 28446-28455, vol. 290, No. 47.

International Search Report for PCT/JP2018/010660 dated Jun. 19, 2018.

(Continued)

*Primary Examiner* — Julie Ha
*Assistant Examiner* — Tara L Martinez
(74) *Attorney, Agent, or Firm* — Knobbe, Martens, Olson & Bear, LLP

(57) ABSTRACT

Disclosed is an agent for inhibiting or reducing light sensitivity comprising a substance that inhibits or reduces ubiquitination, for example, an agent for inhibiting or reducing light sensitivity capable of protecting a retina, reducing retinal degeneration, reducing aging of a retina and/or reducing hyperesthesia. The present invention is suitable for use in amelioration or prevention of a symptom associated with light reception, such as age-related macular degeneration, retinitis pigmentosa, Leber congenital amaurosis, Stargardt disease, cone-rod dystrophy, diabetic retinopathy, macular edema, retinal ischemia, photosensitive seizure, photosensitive epilepsy, psychiatric disorders, photic maculopathy, asthenopia, retinal dysfunction, sleep disorders, migraine and light-induced damage.

6 Claims, 16 Drawing Sheets

Specification includes a Sequence Listing.

(56) References Cited

OTHER PUBLICATIONS

International Preliminary Report on Patentability for PCT/JP2018/010660.
Marquioni-Ramella MD, Suburo AM (2015) Photo-damage, photo-protection and age-related macular degeneration. Photochem Photobiol Sci 14: 1560-1577.
Mitchell P, Liew G, Gopinath B, Wong TY (2018) Age-related macular degeneration. Lancet 392: 1147-1159.
Parmeggiani F, Sato G, De Nadai K, Romano MR, Binotto A, Costagliola C (2011) Clinical and Rehabilitative Management of Retinitis Pigmentosa: Up-to-Date. Curr Genomics 12: 250-259.
Schick T, Ersoy L, Lechanteur YT, Saksens NT, Hoyng CB, den Hollander AI, Kirchhof B, Fauser S (2016) History of Sunlight Exposure Is a Risk Factor for Age-Related Macular Degeneration. Retina 36: 787-790.

* cited by examiner

FIG.14
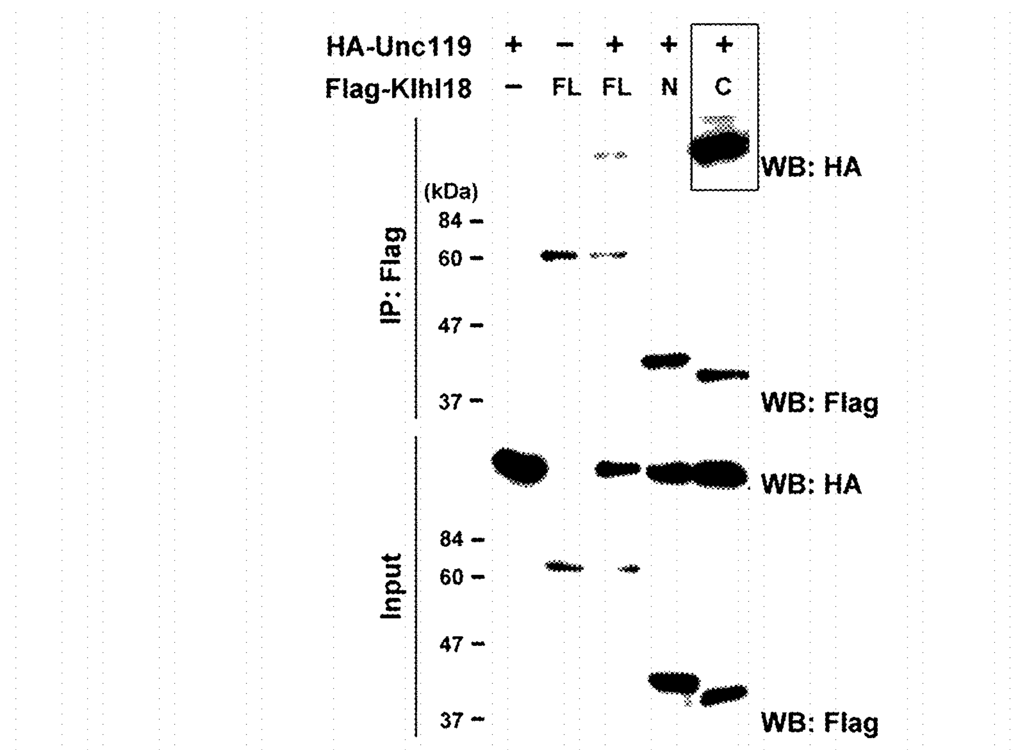
FIG.15
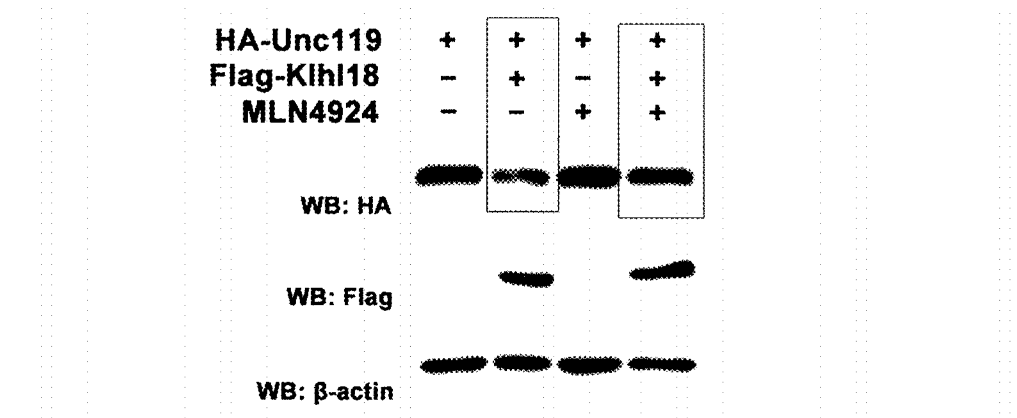
FIG.16
Control — CAG | IRES | EGFP →
Unc119 — CAG | Unc119 | IRES | EGFP →

SEQUENCE LISTING

```
<160> NUMBER OF SEQ ID NOS: 85

<210> SEQ ID NO 1
<211> LENGTH: 4573
<212> TYPE: DNA
<213> ORGANISM: Mus musculus

<400> SEQUENCE: 1

ggcttcgcgt tctgggcagc cttcagcgtg agcccttgcc ccgccctggt tagtgtgaag      60

cctgctggcc aggcctgcgc agttgcggcg gccggggaag atggtggagg acggcgcgga     120

ggagctggag gacttggtgc atttctccgt gtcggagttg cctagtcgcg gctacggcgt     180

catggaggag atccggcggc agggcaagct atgcgacgtg acgctaaaga ttggggacca     240

caagttcagt gctcaccgga tcgtcttagc ggcctccatc ccgtacttcc atgctatgtt     300

tacgaacgac atgatggagt gcaagcagga tgagattgta atgcagggaa tggacccaag     360

tgccctggag gctctcatca actttgctta taatggcaac cttgctatcg accagcagaa     420

tgtgcagtcc ctgctgatgg gggcaagctt cctgcagctg cagagcatca aagatgcttg     480

ctgcacgttc ctccgagaaa ggcttcaccc caaaaattgc ctgggtgtgc gccagtttgc     540

cgagacgatg atgtgtgctg tgttgtacga tgcagccaac agcttcatcc accagcactt     600

tgtagaggtg tctctgtccg aagagttcct ggccctgccc ttggaagacg tgcttgagct     660

ggtgtcccgg gatgagctga atgtgaagtc agaggagcag gtttttgaag ctgcattggc     720

ctgggtcagg tatgaccggg agcagagggg accatgcctg cccgagctgc tgtccaatat     780

ccgcctgcct ctttgccggc cccagttctt atcagatcga gtgcagcaag atgacctggt     840

acggtgctgt cacaaatgca gggacctggt cgatgaagca aaggactatc atctgatgcc     900

agagcgccgg ccccacctgc cagctttcag gactcggccc cgatgctgca cgtccatcgc     960

tgggctcatc tacgctgtgg ggggcctcaa ctcagcaggt gattccctga atgtggtgga    1020
```

```
agtgttcgac cctatcgcca atcgctggga aaagtgccat cccatgacaa cagcccgaag   1080
ccgtgtgggt gtggctgtgg tgaacgggct cctctatgct atcgggggat atgatggtca   1140
gttgcggctg agcaccgtgg aggcctacaa tcctgagacg gacacatgga cccgagtggg   1200
gagcatgaat agcaagcgaa gtgccatggg gacagtcgtg ctggatggac agatctacgt   1260
gtgtggaggc tatgacggca actcctccct caactctgtg gagacctact cacctgagac   1320
ggacaagtgg acagtggtga ctccgatgag ctcaaaccgg agtgctgctg gggtgacagt   1380
ctttgagggc aggatatatg tgtcaggagg ccacgatggc ttgcagatct tcagcagtgt   1440
ggaacactac aaccaccaca cggccacctg gcacccggca gccagcatgc tcaacaagcg   1500
ctgccgacac ggagccgcct ccctgggaag caagatgttt gtctgtgggg gctatgatgg   1560
ctctggcttc ctcagtattg ctgagatgta cagctctgtg gcagaccagt ggtgtctcat   1620
agtacccatg cacacacgcc ggagccgggt ctccctcgtg gccagctgtg ggcgcctcta   1680
tgcagtggga ggttacgatg gacagtcaaa cctaagctca gtggagatgt acgacccaga   1740
gacggaccgc tggacattta tggcccccat ggcatgccac gagggggggg ttggtgtggg   1800
ctgcatccct cttctcacca tctaaggaga ggatgggacg tggtgggcta gggatctggt   1860
acaagcatag gcgcttcctt ccaggggaga gtcctctcag aagaggcagt ggtggaccag   1920
aagacggggt gtaatgtgag cttgccagag ggacagtttt tccaggtgct taagtcctct   1980
ctcactgtgc tgcccttgtg accttaggtt gtcaagatgc acagcacagg acaggagtcc   2040
ctctggggtc ccacagccag taacacggaa gtgctttgct ggtccaggca cacaggctcc   2100
atccaagccc agcgaacacc tgctgcagca ctggcccagc tccccccttgc cacagggagc   2160
actcatgggc aggaggtctt ccagccgagc cttcccttct cctgcagccc tgctgtggcc   2220
gcttgggaag tgtgggtaaa gctgggagag aagggacacc ctggtgttgt cactgcctgt   2280
ggtggtgcag ctacagcagc tagcatgctg cgagtgcacg ggctctccct tcgacagggg   2340
cacagaggac ttggcccctg tctccagcaa gcagggagaa cagaagtctt ccccatgcct   2400
gattttttgg gaatccagtg aggtctttct ccacttgtcc ccaagaaaca ggaagggaat   2460
ggagatgctc gagagaaact ggaggaaatg gaaacaagaa aatgttgaag agaaactgga   2520
aggaaaaggc ttgaagtgaa cattttccac aggacggaaa cagaaaagac actaaaaaca   2580
aacacacatt tacatggaga accatcaacc atgacaacag tggtgtccac tcccacattc   2640
ggatcccagg gtcctacgtc ctcctaaagc agtcggggtt tcctctgaat cccacagtgt   2700
gtctgaaatc aggacattct tgactgacct gtagcaaggt gctcatgggg tttggtctcc   2760
tcacccacgt cagaggactt tttaaatcat aggcttaggg agcgggttaa attactgcca   2820
ctcacctctg cccgagctcc caactgtcac cccatggtta cctccctaca ccacccagcg   2880
ctcccacaga tccccactcc cacgtacatc ctttcccttt ttggccagca agaaacaaca   2940
tgtctgccca gattcgcact cacccatcca ccatccttga ataactctcc ctcatcacaa   3000
cgcttccaga gcacattgac catttgtacc tctaggacct aaccaggggc ttgctcctac   3060
cagccatgga ccagcttggt caggtgactc gtcttccctg ccattccgct attttccatc   3120
catttgccaa ccctgggtgt ccgtccacct tctctccagc aagatgggcc tttacattca   3180
agctacgaac gctggcgtca tggtataaag gcttacaaag aaatgtcttt tgctgctgca   3240
aggaagagat tttctatttc ttcccctgat cttggcaaat gacctcgtga agagactcaa   3300
tgctcctcct ccctctggat gggaccttac catagcacag aaggacccag agggagactg   3360
```

```
tctcttacca gtgcactggg cagtggggca gaccttcaac tgccgctgcc aaaatctgct   3420
ttcctaaaat ccttccagta gcgacgagaa ggatataatt gtttctagcc ccaaactggg   3480
tcttagggtc cggtctgttc cactgtccac ctgattggtt tcttgccctc tgctgcctgc   3540
ctggatcggc ctagaagacg gttcaggcgg ctctgggtga agcctgcggg ggcagggggg   3600
tggtcccttt ccccagacca tcaggtttcc cagtgtgtgc aattgccata gattcagaag   3660
gaaggactct tgttccctgc aatgtaaaga gccgggcctc tgctctaagc acttgaaaat   3720
aatgttttta tcttaaaaga ctgaacaatc tggtaactga tacatcttaa ctaggctccc   3780
agtggagcgc cagcatttct tcctgcccct cagtttgcct gctgaggtag actctagggg   3840
actatgggtc ttggtttcct cttagtccta ttaggagggg tgtatccacg ctcctcttat   3900
taagtccttc tgtgaatgta ctgcccagcc tcgactgtga aggtgctgag aaccagtccg   3960
tgggctccca ggtgggcctc ctgggtcctc acgatgcaag cagactgcat ccctagagat   4020
gatacgccat ctccccaccc cccccgccac cccaccccgg cctgctgctg ccaggttaac   4080
cttcctgcct ccactcccac ctcctagtgt agacagtgtt tccaagaacc atcaagtcag   4140
tgttttgatc taggctctga gcacacaagc gaacagaaac atttttatac tcccctgtct   4200
gagggcgatg gctgatctgt ctcagtgtca gaactgtagg atcatgtgag aacaggcatc   4260
acccaaggac actggaaaga atgtagcagg aggtgggtcc gacacgcctg gtgggccatg   4320
gggtctggcc actgcacttc ctcttctcct ctctctctgg gcttcaccag aggtcacaag   4380
cagaagagag ctgaagccca gcctctgatg gaactaagta ggaatcctga ccctcttcac   4440
ccacagctat ttcacgggaa acttttattt ataggacgca tgtcttttgt gttgagaaac   4500
caaagagaaa taaagagaac acgcctaata aaaaaaaaaa aaaaaaaaaa aaaaaaaaaa   4560
aaaaaaaaaa aaa                                                      4573
```

```
<210> SEQ ID NO 2
<211> LENGTH: 1725
<212> TYPE: DNA
<213> ORGANISM: Mus musculus

<400> SEQUENCE: 2
```

```
atggtggagg acggcgcgga ggagctggag gacttggtgc atttctccgt gtcggagttg     60
cctagtcgcg gctacggcgt catggaggag atccggcggc agggcaagct atgcgacgtg    120
acgctaaaga ttggggacca caagttcagt gctcaccgga tcgtcttagc ggcctccatc    180
ccgtacttcc atgctatgtt tacgaacgac atgatggagt gcaagcagga tgagattgta    240
atgcagggaa tggacccaag tgccctggag gctctcatca actttgctta taatggcaac    300
cttgctatcg accagcagaa tgtgcagtcc ctgctgatgg gggcaagctt cctgcagctg    360
cagagcatca aagatgcttg ctgcacgttc ctccgagaaa ggcttcaccc caaaaattgc    420
ctgggtgtgc gccagtttgc cgagacgatg atgtgtgctg tgttgtacga tgcagccaac    480
agcttcatcc accagcactt tgtagaggtg tctctgtccg aagagttcct ggccctgccc    540
ttggaagacg tgcttgagct ggtgtcccgg gatgagctga atgtgaagtc agaggagcag    600
gtttttgaag ctgcattggc ctgggtcagg tatgaccggg agcagagggg accatgcctg    660
cccgagctgc tgtccaatat ccgcctgcct ctttgccggc cccagttctt atcagatcga    720
gtgcagcaag atgacctggt acggtgctgt cacaaatgca gggacctggt cgatgaagca    780
aaggactatc atctgatgcc agagcgccgg ccccacctgc cagctttcag gactcggccc    840
cgatgctgca cgtccatcgc tgggctcatc tacgctgtgg ggggcctcaa ctcagcaggt    900
```

```
gattccctga atgtggtgga agtgttcgac cctatcgcca atcgctggga aaagtgccat    960

cccatgacaa cagcccgaag ccgtgtgggt gtggctgtgg tgaacgggct cctctatgct   1020

atcgggggat atgatggtca gttgcggctg agcaccgtgg aggcctacaa tcctgagacg   1080

gacacatgga cccgagtggg gagcatgaat agcaagcgaa gtgccatggg gacagtcgtg   1140

ctggatggac agatctacgt gtgtggaggc tatgacggca actcctccct caactctgtg   1200

gagacctact cacctgagac ggacaagtgg acagtggtga ctccgatgag ctcaaaccgg   1260

agtgctgctg gggtgacagt ctttgagggc aggatatatg tgtcaggagg ccacgatggc   1320

ttgcagatct tcagcagtgt ggaacactac aaccaccaca cggccacctg gcacccggca   1380

gccagcatgc tcaacaagcg ctgccgacac ggagccgcct ccctgggaag caagatgttt   1440

gtctgtgggg gctatgatgg ctctggcttc ctcagtattg ctgagatgta cagctctgtg   1500

gcagaccagt ggtgtctcat agtacccatg cacacacgcc ggagccgggt ctccctcgtg   1560

gccagctgtg ggcgcctcta tgcagtggga ggttacgatg gacagtcaaa cctaagctca   1620

gtggagatgt acgacccaga gacggaccgc tggacattta tggcccccat ggcatgccac   1680

gaggggggggg ttggtgtggg ctgcatccct cttctcacca tctaa                   1725
```

```
<210> SEQ ID NO 3
<211> LENGTH: 574
<212> TYPE: PRT
<213> ORGANISM: Mus musculus

<400> SEQUENCE: 3

Met Val Glu Asp Gly Ala Glu Glu Leu Glu Asp Leu Val His Phe Ser
1               5                   10                  15

Val Ser Glu Leu Pro Ser Arg Gly Tyr Gly Val Met Glu Glu Ile Arg
            20                  25                  30

Arg Gln Gly Lys Leu Cys Asp Val Thr Leu Lys Ile Gly Asp His Lys
        35                  40                  45

Phe Ser Ala His Arg Ile Val Leu Ala Ala Ser Ile Pro Tyr Phe His
    50                  55                  60

Ala Met Phe Thr Asn Asp Met Met Glu Cys Lys Gln Asp Glu Ile Val
65                  70                  75                  80

Met Gln Gly Met Asp Pro Ser Ala Leu Glu Ala Leu Ile Asn Phe Ala
                85                  90                  95

Tyr Asn Gly Asn Leu Ala Ile Asp Gln Gln Asn Val Gln Ser Leu Leu
            100                 105                 110

Met Gly Ala Ser Phe Leu Gln Leu Gln Ser Ile Lys Asp Ala Cys Cys
        115                 120                 125

Thr Phe Leu Arg Glu Arg Leu His Pro Lys Asn Cys Leu Gly Val Arg
    130                 135                 140

Gln Phe Ala Glu Thr Met Met Cys Ala Val Leu Tyr Asp Ala Ala Asn
145                 150                 155                 160

Ser Phe Ile His Gln His Phe Val Glu Val Ser Leu Ser Glu Glu Phe
                165                 170                 175

Leu Ala Leu Pro Leu Glu Asp Val Leu Glu Leu Val Ser Arg Asp Glu
            180                 185                 190

Leu Asn Val Lys Ser Glu Glu Gln Val Phe Glu Ala Ala Leu Ala Trp
        195                 200                 205

Val Arg Tyr Asp Arg Glu Gln Arg Gly Pro Cys Leu Pro Glu Leu Leu
    210                 215                 220
```

```
Ser Asn Ile Arg Leu Pro Leu Cys Arg Pro Gln Phe Leu Ser Asp Arg
225                 230                 235                 240

Val Gln Gln Asp Asp Leu Val Arg Cys Cys His Lys Cys Arg Asp Leu
                245                 250                 255

Val Asp Glu Ala Lys Asp Tyr His Leu Met Pro Glu Arg Arg Pro His
            260                 265                 270

Leu Pro Ala Phe Arg Thr Arg Pro Arg Cys Cys Thr Ser Ile Ala Gly
        275                 280                 285

Leu Ile Tyr Ala Val Gly Gly Leu Asn Ser Ala Gly Asp Ser Leu Asn
    290                 295                 300

Val Val Glu Val Phe Asp Pro Ile Ala Asn Arg Trp Glu Lys Cys His
305                 310                 315                 320

Pro Met Thr Thr Ala Arg Ser Arg Val Gly Val Ala Val Val Asn Gly
                325                 330                 335

Leu Leu Tyr Ala Ile Gly Gly Tyr Asp Gly Gln Leu Arg Leu Ser Thr
            340                 345                 350

Val Glu Ala Tyr Asn Pro Glu Thr Asp Thr Trp Thr Arg Val Gly Ser
        355                 360                 365

Met Asn Ser Lys Arg Ser Ala Met Gly Thr Val Val Leu Asp Gly Gln
    370                 375                 380

Ile Tyr Val Cys Gly Gly Tyr Asp Gly Asn Ser Ser Leu Asn Ser Val
385                 390                 395                 400

Glu Thr Tyr Ser Pro Glu Thr Asp Lys Trp Thr Val Val Thr Pro Met
                405                 410                 415

Ser Ser Asn Arg Ser Ala Ala Gly Val Thr Val Phe Glu Gly Arg Ile
            420                 425                 430

Tyr Val Ser Gly Gly His Asp Gly Leu Gln Ile Phe Ser Ser Val Glu
        435                 440                 445

His Tyr Asn His His Thr Ala Thr Trp His Pro Ala Ala Ser Met Leu
    450                 455                 460

Asn Lys Arg Cys Arg His Gly Ala Ala Ser Leu Gly Ser Lys Met Phe
465                 470                 475                 480

Val Cys Gly Gly Tyr Asp Gly Ser Gly Phe Leu Ser Ile Ala Glu Met
                485                 490                 495

Tyr Ser Ser Val Ala Asp Gln Trp Cys Leu Ile Val Pro Met His Thr
            500                 505                 510

Arg Arg Ser Arg Val Ser Leu Val Ala Ser Cys Gly Arg Leu Tyr Ala
        515                 520                 525

Val Gly Gly Tyr Asp Gly Gln Ser Asn Leu Ser Ser Val Glu Met Tyr
    530                 535                 540

Asp Pro Glu Thr Asp Arg Trp Thr Phe Met Ala Pro Met Ala Cys His
545                 550                 555                 560

Glu Gly Gly Val Gly Val Gly Cys Ile Pro Leu Leu Thr Ile
                565                 570
```

<210> SEQ ID NO 4
<211> LENGTH: 4538
<212> TYPE: DNA
<213> ORGANISM: Mus musculus

<400> SEQUENCE: 4

```
cgcgttctgg gcagccttca gcgtgagccc ttgccccgcc ctggttagtg tgaagcctgc      60

tggccaggcc tgcgcagttg cggcggccgg ggaagatggt ggaggacggc gcggaggagc     120

tggaggactt ggtgcatttc tccgtgtcgg agttgcctag tcgcggctac ggcgtcatgg     180
```

```
aggagatccg gcggcagggc aagctatgcg acgtgacgct aaagattggg gaccacaagt    240
tcagtgctca ccggatcgtc ttagcggcct ccatcccgta cttccatgct atgtttacga    300
acgacatgat ggagtgcaag caggatgaga ttgtaatgca gggaatggac ccaagtgccc    360
tggaggctct catcaacttt gcttataatg gcaaccttgc tatcgaccag cagaatgtgc    420
agtccctgct gatgggggca agcttcctgc agctgcagag catcaaagat gcttgctgca    480
cgttcctccg agaaaggctt caccccaaaa attgcctggg tgtgcgccag tttgccgaga    540
cgatgatgtg tgctgtgttg tacgatgcag ccaacagctt catccaccag cactttgtag    600
aggtgtctct gtccgaagag ttcctggccc tgcccttgga agacgtgctt gagctggtgt    660
cccgggatga gctgaatgtg aagtcagagg agcaggtttt tgaagctgca ttggcctggg    720
tcaggtatga ccgggagcag aggggaccat gcctgcccga gctgctgtcc aatatccgcc    780
tgcctctttg ccggccccag ttcttatcag atcgagtgca gcaagatgac ctggtacggt    840
gctgtcacaa atgcagggac ctggtcgatg aagcaaagga ctatcatctg atgccagagc    900
gccggcccca cctgccagct ttcaggactc ggccccgatg ctgcacgtcc atcgctgggc    960
tcatctacgc tgtggggggc ctcaactcag cagcaaattt ttatgcaggt gattccctga   1020
atgtggtgga agtgttcgac cctatcgcca atcgctggga aaagtgccat cccatgacaa   1080
cagcccgaag ccgtgtgggt gtggctgtgg tgaacgggct cctctatgct atcgggggat   1140
atgatggtca gttgcggctg agcaccgtgg aggcctacaa tcctgagacg gacacatgga   1200
cccgagtggg gagcatgaat agcaagcgaa gtgccatggg gacagtcgtg ctggatggac   1260
agatctacgt gtgtggaggc tatgacggca actcctccct caactctgtg gagacctact   1320
cacctgagac ggacaagtgg acagtggtga ctccgatgag ctcaaaccgg agtgctgctg   1380
ggtgacagt ctttgagggc aggatatatg tgtcaggagg ccacgatggc ttgcagatct   1440
tcagcagtgt ggaacactac aaccaccaca cggccacctg gcacccggca gccagcatgc   1500
tcaacaagcg ctgccgacac ggagccgcct ccctgggaag caagatgttt gtctgtgggg   1560
gctatgatgg ctctggcttc ctcagtattg ctgagatgta cagctctgtg gcagaccagt   1620
ggtgtctcat agtacccatg cacacacgcc ggagccgggt ctccctcgtg gccagctgtg   1680
ggcgcctcta tgcagtggga ggttacgatg gacagtcaaa cctaagctca gtggagatgt   1740
acgacccaga gacggaccgc tggacattta tggcccccat ggcatgccac gagggggggg   1800
ttggtgtggg ctgcatccct cttctcacca tctaaggaga ggatgggacg tggtgggcta   1860
gggatctggt acaagcatag gcgcttcctt ccaggggaga gtcctctcag aagaggcagt   1920
ggtggaccag aagacggggt gtaatgtgag cttgccagag ggacagtttt tccaggtgct   1980
taagtcctct ctcactgtgc tgcccttgtg accttaggtt gtcaagatgc acagcacagg   2040
acaggagtcc ctctggggtc ccacagccag taacacggaa gtgctttgct ggtccaggca   2100
cacaggctcc atccaagccc agcgaacacc tgctgcagca ctggcccagc tccccccttgc   2160
cacagggagc actcatgggc aggaggtctt ccagccgagc cttcccttct cctgcagccc   2220
tgctgtggcc gcttgggaag tgtgggtaaa gctgggagag aagggacacc ctggtgttgt   2280
cactgcctgt ggtggtgcag ctacagcagc tagcatgctg cgagtgcacg ggctctccct   2340
tcgacagggg cacagaggac ttggcccctg tctccagcaa gcagggagaa cagaagtctt   2400
ccccatgcct gattttttgg gaatccagtg aggtctttct ccacttgtcc ccaagaaaca   2460
ggaagggaat ggagatgctc gagagaaact ggaggaaatg gaaacaagaa aatgttgaag   2520
```

```
agaaactgga aggaaaaggc ttgaagtgaa cattttccac aggacggaaa cagaaaagac   2580
actaaaaaca aacacacatt tacatggaga accatcaacc atgacaacag tggtgtccac   2640
tcccacattc ggatcccagg gtcctacgtc ctcctaaagc agtcggggtt tcctctgaat   2700
cccacagtgt gtctgaaatc aggacattct tgactgacct gtagcaaggt gctcatgggg   2760
tttggtctcc tcacccacgt cagaggactt tttaaatcat aggcttaggg agcgggttaa   2820
attactgcca ctcacctctg cccgagctcc caactgtcac cccatggtta cctccctaca   2880
ccacccagcg ctcccacaga tccccactcc cacgtacatc ctttcccttt ttggccagca   2940
agaaacaaca tgtctgccca gattcgcact cacccatcca ccatccttga ataactctcc   3000
ctcatcacaa cgcttccaga gcacattgac catttgtacc tctaggacct aaccaggggc   3060
ttgctcctac cagccatgga ccagcttggt caggtgactc gtcttccctg ccattccgct   3120
attttccatc catttgccaa ccctgggtgt ccgtccacct tctctccagc aagatgggcc   3180
tttacattca agctacgaac gctggcgtca tggtataaag gcttacaaag aaatgtcttt   3240
tgctgctgca aggaagagat ttctatttc ttcccctgat cttggcaaat gacctcgtga   3300
agagactcaa tgctcctcct ccctctggat gggaccttac catagcacag aaggacccag   3360
agggagactg tctcttacca gtgcactggg cagtggggca gaccttcaac tgccgctgcc   3420
aaaatctgct ttcctaaaat ccttccagta gcgacgagaa ggatataatt gtttctagcc   3480
ccaaactggg tcttagggtc cggtctgttc cactgtccac ctgattggtt tcttgccctc   3540
tgctgcctgc ctggatcggc ctagaagacg gttcaggcgg ctctgggtga agcctgcggg   3600
ggcagggggg tggtcccttt ccccagacca tcaggtttcc cagtgtgtgc aattgccata   3660
gattcagaag gaaggactct tgttccctgc aatgtaaaga gccgggcctc tgctctaagc   3720
acttgaaaat aatgttttta tcttaaaaga ctgaacaatc tggtaactga tacatcttaa   3780
ctaggctccc agtggagcgc cagcatttct tcctgcccct cagtttgcct gctgaggtag   3840
actctagggg actatgggtc ttggtttcct cttagtccta ttaggagggg tgtatccacg   3900
ctcctcttat taagtccttc tgtgaatgta ctgcccagcc tcgactgtga aggtgctgag   3960
aaccagtccg tgggctccca ggtgggcctc ctgggtcctc acgatgcaag cagactgcat   4020
ccctagagat gatacgccat ctccccaccc cccccgccac cccaccccgg cctgctgctg   4080
ccaggttaac cttcctgcct ccactcccac ctcctagtgt agacagtgtt tccaagaacc   4140
atcaagtcag tgttttgatc taggctctga gcacacaagc gaacagaaac atttttatac   4200
tcccctgtct gagggcgatg gctgatctgt ctcagtgtca gaactgtagg atcatgtgag   4260
aacaggcatc acccaaggac actggaaaga atgtagcagg aggtgggtcc gacacgcctg   4320
gtgggccatg ggtctggcc actgcacttc ctcttctcct ctctctctgg gcttcaccag   4380
aggtcacaag cagaagagag ctgaagccca gcctctgatg gaactaagta ggaatcctga   4440
ccctcttcac ccacagctat ttcacgggaa acttttattt ataggacgca tgtcttttgt   4500
gttgagaaac caaagagaaa taaagagaac acgcctaa                            4538
```

<210> SEQ ID NO 5
<211> LENGTH: 1740
<212> TYPE: DNA
<213> ORGANISM: Mus musculus

<400> SEQUENCE: 5

```
atggtggagg acggcgcgga ggagctggag gacttggtgc atttctccgt gtcggagttg     60
cctagtcgcg gctacggcgt catggaggag atccggcggc agggcaagct atgcgacgtg    120
```

acgctaaaga ttggggacca caagttcagt gctcaccgga tcgtcttagc ggcctccatc 180
ccgtacttcc atgctatgtt tacgaacgac atgatggagt gcaagcagga tgagattgta 240
atgcagggaa tggacccaag tgccctggag gctctcatca actttgctta taatggcaac 300
cttgctatcg accagcagaa tgtgcagtcc ctgctgatgg gggcaagctt cctgcagctg 360
cagagcatca aagatgcttg ctgcacgttc ctccgagaaa ggcttcaccc caaaaattgc 420
ctgggtgtgc gccagtttgc cgagacgatg atgtgtgctg tgttgtacga tgcagccaac 480
agcttcatcc accagcactt tgtagaggtg tctctgtccg aagagttcct ggccctgccc 540
ttggaagacg tgcttgagct ggtgtcccgg gatgagctga atgtgaagtc agaggagcag 600
gtttttgaag ctgcattggc ctgggtcagg tatgaccggg agcagagggg accatgcctg 660
cccgagctgc tgtccaatat ccgcctgcct ctttgccggc cccagttctt atcagatcga 720
gtgcagcaag atgacctggt acggtgctgt cacaaatgca gggacctggt cgatgaagca 780
aaggactatc atctgatgcc agagcgccgg ccccacctgc cagctttcag gactcggccc 840
cgatgctgca cgtccatcgc tgggctcatc tacgctgtgg ggggcctcaa ctcagcagca 900
aatttttatg caggtgattc cctgaatgtg gtggaagtgt tcgaccctat cgccaatcgc 960
tgggaaaagt gccatcccat gacaacagcc cgaagccgtg tgggtgtggc tgtggtgaac 1020
gggctcctct atgctatcgg gggatatgat ggtcagttgc ggctgagcac cgtggaggcc 1080
tacaatcctg agacggacac atggacccga gtggggagca tgaatagcaa gcgaagtgcc 1140
atggggacag tcgtgctgga tggacagatc tacgtgtgtg gaggctatga cggcaactcc 1200
tccctcaact ctgtggagac ctactcacct gagacggaca agtggacagt ggtgactccg 1260
atgagctcaa accggagtgc tgctggggtg acagtctttg agggcaggat atatgtgtca 1320
ggaggccacg atggcttgca gatcttcagc agtgtggaac actacaacca ccacacggcc 1380
acctggcacc cggcagccag catgctcaac aagcgctgcc gacacggagc cgcctccctg 1440
ggaagcaaga tgtttgtctg tgggggctat gatggctctg gcttcctcag tattgctgag 1500
atgtacagct ctgtggcaga ccagtggtgt ctcatagtac ccatgcacac acgccggagc 1560
cgggtctccc tcgtggccag ctgtgggcgc ctctatgcag tgggaggtta cgatggacag 1620
tcaaacctaa gctcagtgga gatgtacgac ccagagacgg accgctggac atttatggcc 1680
cccatggcat gccacgaggg gggggttggt gtgggctgca tccctcttct caccatctaa 1740

<210> SEQ ID NO 6
<211> LENGTH: 579
<212> TYPE: PRT
<213> ORGANISM: Mus musculus

<400> SEQUENCE: 6

Met Val Glu Asp Gly Ala Glu Glu Leu Glu Asp Leu Val His Phe Ser
1 5 10 15

Val Ser Glu Leu Pro Ser Arg Gly Tyr Gly Val Met Glu Glu Ile Arg
20 25 30

Arg Gln Gly Lys Leu Cys Asp Val Thr Leu Lys Ile Gly Asp His Lys
35 40 45

Phe Ser Ala His Arg Ile Val Leu Ala Ala Ser Ile Pro Tyr Phe His
50 55 60

Ala Met Phe Thr Asn Asp Met Met Glu Cys Lys Gln Asp Glu Ile Val
65 70 75 80

Met Gln Gly Met Asp Pro Ser Ala Leu Glu Ala Leu Ile Asn Phe Ala

```
                85                  90                  95

Tyr Asn Gly Asn Leu Ala Ile Asp Gln Gln Asn Val Gln Ser Leu Leu
            100                 105                 110

Met Gly Ala Ser Phe Leu Gln Leu Gln Ser Ile Lys Asp Ala Cys Cys
        115                 120                 125

Thr Phe Leu Arg Glu Arg Leu His Pro Lys Asn Cys Leu Gly Val Arg
    130                 135                 140

Gln Phe Ala Glu Thr Met Met Cys Ala Val Leu Tyr Asp Ala Ala Asn
145                 150                 155                 160

Ser Phe Ile His Gln His Phe Val Glu Val Ser Leu Ser Glu Glu Phe
                165                 170                 175

Leu Ala Leu Pro Leu Glu Asp Val Leu Glu Leu Val Ser Arg Asp Glu
            180                 185                 190

Leu Asn Val Lys Ser Glu Glu Gln Val Phe Glu Ala Ala Leu Ala Trp
        195                 200                 205

Val Arg Tyr Asp Arg Glu Gln Arg Gly Pro Cys Leu Pro Glu Leu Leu
    210                 215                 220

Ser Asn Ile Arg Leu Pro Leu Cys Arg Pro Gln Phe Leu Ser Asp Arg
225                 230                 235                 240

Val Gln Gln Asp Asp Leu Val Arg Cys Cys His Lys Cys Arg Asp Leu
                245                 250                 255

Val Asp Glu Ala Lys Asp Tyr His Leu Met Pro Glu Arg Arg Pro His
            260                 265                 270

Leu Pro Ala Phe Arg Thr Arg Pro Arg Cys Cys Thr Ser Ile Ala Gly
        275                 280                 285

Leu Ile Tyr Ala Val Gly Gly Leu Asn Ser Ala Ala Asn Phe Tyr Ala
    290                 295                 300

Gly Asp Ser Leu Asn Val Val Glu Val Phe Asp Pro Ile Ala Asn Arg
305                 310                 315                 320

Trp Glu Lys Cys His Pro Met Thr Thr Ala Arg Ser Arg Val Gly Val
                325                 330                 335

Ala Val Val Asn Gly Leu Leu Tyr Ala Ile Gly Gly Tyr Asp Gly Gln
            340                 345                 350

Leu Arg Leu Ser Thr Val Glu Ala Tyr Asn Pro Glu Thr Asp Thr Trp
        355                 360                 365

Thr Arg Val Gly Ser Met Asn Ser Lys Arg Ser Ala Met Gly Thr Val
    370                 375                 380

Val Leu Asp Gly Gln Ile Tyr Val Cys Gly Gly Tyr Asp Gly Asn Ser
385                 390                 395                 400

Ser Leu Asn Ser Val Glu Thr Tyr Ser Pro Glu Thr Asp Lys Trp Thr
                405                 410                 415

Val Val Thr Pro Met Ser Ser Asn Arg Ser Ala Ala Gly Val Thr Val
            420                 425                 430

Phe Glu Gly Arg Ile Tyr Val Ser Gly Gly His Asp Gly Leu Gln Ile
        435                 440                 445

Phe Ser Ser Val Glu His Tyr Asn His His Thr Ala Thr Trp His Pro
    450                 455                 460

Ala Ala Ser Met Leu Asn Lys Arg Cys Arg His Gly Ala Ala Ser Leu
465                 470                 475                 480

Gly Ser Lys Met Phe Val Cys Gly Gly Tyr Asp Gly Ser Gly Phe Leu
                485                 490                 495

Ser Ile Ala Glu Met Tyr Ser Ser Val Ala Asp Gln Trp Cys Leu Ile
            500                 505                 510
```

```
Val Pro Met His Thr Arg Arg Ser Arg Val Ser Leu Val Ala Ser Cys
        515                 520                 525

Gly Arg Leu Tyr Ala Val Gly Gly Tyr Asp Gly Gln Ser Asn Leu Ser
    530                 535                 540

Ser Val Glu Met Tyr Asp Pro Glu Thr Asp Arg Trp Thr Phe Met Ala
545                 550                 555                 560

Pro Met Ala Cys His Glu Gly Gly Val Gly Val Gly Cys Ile Pro Leu
                565                 570                 575

Leu Thr Ile


<210> SEQ ID NO 7
<211> LENGTH: 3165
<212> TYPE: DNA
<213> ORGANISM: Mus musculus

<400> SEQUENCE: 7

cttcgcgttc tgggcagcct tcagcgtgag cccttgcccc gccctggtta gtgtgaagcc      60

tgctggccag gcctgcgcag ttgcggcggc cggggaagat ggtggaggac ggcgcggagg     120

agctggagga cttggtgcat ttctccgtgt cggagttgcc tagtcgcggc tacggcgtca     180

tggaggagat ccggcggcag ggcaagctat gcgacgtgac gctaaagatt ggggaccaca     240

agttcagtgc tcaccggatc gtcttagcgg cctccatccc gtacttccat gctatgttta     300

cgaacgacat gatggagtgc aagcaggatg agattgtaat gcagggaatg gacccaagtg     360

ccctggaggc tctcatcaac tttgcttata atggcaacct tgctatcgac cagcagaatg     420

tgcagtccct gctgatgggg gcaagcttcc tgcagctgca gagcatcaaa gatgcttgct     480

gcacgttcct ccgagaaagg cttcacccca aaaattgcct gggtgtgcgc cagtttgccg     540

agacgatgat gtgtgctgtg ttgtacgatg cagccaacag cttcatccac cagcactttg     600

tagaggtgtc tctgtccgaa gagttcctgg ccctgccctt ggaagacgtg cttgagctgg     660

tgtcccggga tgagctgaat gtgaagtcag aggagcagag tgagcatgtc caaaggaggg     720

aggagcttgg cacaggaatg gaggacaccc atgtagccat ctctagaaca caggtcagca     780

gagaggtttt tgaagctgca ttggcctggg tcaggtatga ccgggagcag aggggaccat     840

gcctgcccga gctgctgtcc aatatccgcc tgcctctttg ccggccccag ttcttatcag     900

atcgagtgca gcaagatgac ctggtacggt gctgtcacaa atgcagggac ctggtcgatg     960

aagcaaagga ctatcatctg atgccagagc gccggcccca cctgccagct ttcaggactc    1020

ggccccgatg ctgcacgtcc atcgctgggc tcatctacgc tgtgggggc ctcaactcag    1080

cagcaaattt ttatgcaggt gattccctga atgtggtgga agtgttcgac cctatcgcca    1140

atcgctggga aaagtgccat cccatgacaa cagcccgaag ccgtgtgggt gtggctgtgg    1200

tgaacgggct cctctatgct atcgggggat atgatggtca gttgcggctg agcaccgtgg    1260

aggcctacaa tcctgagacg gacacatgga cccgagtggg gagcatgaat agcaagcgaa    1320

gtgccatggg gacagtcgtg ctggatggac agatctacgt gtgtggaggc tatgacggca    1380

actcctccct caactctgtg gagacctact cacctgagac ggacaagtaa ggctgactta    1440

tccccctgcc tcagcttctt gagtgctgaa attacagata gaaactatta tactcggcct    1500

accttcccca cctccaggcc tttgtgcttg ccaggcttcc agcccccctc cccccacccc    1560

cactcccacc tcttgtttag ttttgctttg ctttgttgga gaaaaggtct caacctcagg    1620

actctgatga gccacctcag ccacagagac atgccgtggc acggagctta aagcttctcc    1680
```

```
tggctaggaa gtgacttaac aatacttgca tgtagtcgat gtctacatcc ttggctaaat   1740

gtcagacacg gtgatgcgcc cctttgatcc ctttacttga aggcagaggc aagtgtgtct   1800

ccgtgagttc aaaaccagtc tgctttatgt agtgcattct agactagcca aggctacaaa   1860

gcaggacttg gtctcaaaaa aacaaaacaa aaaaatatat tttttaattc cttgtttaag   1920

tgaaatttca tggttaaatt tcaaaagagc taaagcaatg gtggttcaat cccaagactt   1980

gaggtggagg caggaggctc aggagttcga ggtgacatga acccatttca aataaacgaa   2040

aggctgagat gtttggaaac acttattcct tggtcacgtc agtccactgt actggaagtg   2100

caggtgcaga tgctccttag aagcagataa ggagcatctg cacagcttgt tccacagcag   2160

tgaggcctgc tgtgaaggac tgtggggtca gagaaccccg ggcagagttg gtatctgttt   2220

cttcagagcc tttgtcttgc caccacacat acgacattgc aaaagttcta gaaaatctgg   2280

cggtgaggaa tcccgtttaa acttgcgttc tctgtaacac ccattacaat cgtgtaggat   2340

gcttttgtgg aacactagaa acactggcaa tgctggctga attactcatt ctggtgtttg   2400

tatcctcccg tcttagataa ctgactgagc ggatgggttg agccaactca tcagcacatt   2460

ctaaagccag tcttctgttg cctagcaact gactgcagct cttatcaagt agaaaggagg   2520

ctggtcctcc ctggtgctcc cttttggtta tcctcaggta ggctggtcct ccctggtgcc   2580

tgcttttttt tttatcagat tgacaggttc ctcctagcgc tcagtttggt aggccatgag   2640

cgcactgtca ctgtctttcc ttggaggtct gtgctgtgtc tggagctctt atcatggtgt   2700

ggggagcatt catcactcta gggcaggggc acaaggtgga ctcaccagac agacagtgag   2760

gctgagggga tggcttacgt ttataaaata tttgccctgc aagaatgaat ccaaaaatgc   2820

caggcatgat agttcatgct tatagtcctg gctgagaagg tggagacagg aggatccctc   2880

agagcttgct ggcctgccag tctagcttaa tagatgagct ccaggccagt aagatcctgt   2940

gtctcagcac ttgagagcta caacaggagg actccagtcc aaagccagcc cgagctacag   3000

aatgagagcc ttcctcagca aacaaacaga accaggcagg atggcacatg cctttaattc   3060

caggactaag gaggcagagg tagagggttc gaggctagcc ctgtctacag agttctagga   3120

cagccagggc tacacagggc tacaggtctc aaagaaagaa agaaa                   3165
```

```
<210> SEQ ID NO 8
<211> LENGTH: 1332
<212> TYPE: DNA
<213> ORGANISM: Mus musculus

<400> SEQUENCE: 8

atggtggagg acggcgcgga ggagctggag gacttggtgc atttctccgt gtcggagttg     60

cctagtcgcg gctacggcgt catggaggag atccggcggc agggcaagct atgcgacgtg    120

acgctaaaga ttggggacca caagttcagt gctcaccgga tcgtcttagc ggcctccatc    180

ccgtacttcc atgctatgtt tacgaacgac atgatggagt gcaagcagga tgagattgta    240

atgcagggaa tggacccaag tgccctggag gctctcatca actttgctta taatggcaac    300

cttgctatcg accagcagaa tgtgcagtcc ctgctgatgg gggcaagctt cctgcagctg    360

cagagcatca aagatgcttg ctgcacgttc ctccgagaaa ggcttcaccc caaaaattgc    420

ctgggtgtgc gccagtttgc cgagacgatg atgtgtgctg tgttgtacga tgcagccaac    480

agcttcatcc accagcactt tgtagaggtg tctctgtccg aagagttcct ggccctgccc    540

ttggaagacg tgcttgagct ggtgtcccgg gatgagctga atgtgaagtc agaggagcag    600

agtgagcatg tccaaaggag ggaggagctt ggcacaggaa tggaggacac ccatgtagcc    660
```

```
atctctagaa cacaggtcag cagagaggtt tttgaagctg cattggcctg ggtcaggtat    720

gaccgggagc agaggggacc atgcctgccc gagctgctgt ccaatatccg cctgcctctt    780

tgccggcccc agttcttatc agatcgagtg cagcaagatg acctggtacg gtgctgtcac    840

aaatgcaggg acctggtcga tgaagcaaag gactatcatc tgatgccaga gcgccggccc    900

cacctgccag ctttcaggac tcggccccga tgctgcacgt ccatcgctgg gctcatctac    960

gctgtggggg gcctcaactc agcagcaaat tttatgcag gtgattccct gaatgtggtg    1020

gaagtgttcg accctatcgc caatcgctgg gaaaagtgcc atcccatgac aacagcccga   1080

agccgtgtgg gtgtggctgt ggtgaacggg ctcctctatg ctatcggggg atatgatggt   1140

cagttgcggc tgagcaccgt ggaggcctac aatcctgaga cggacacatg gacccgagtg   1200

gggagcatga atagcaagcg aagtgccatg ggacagtcg tgctggatgg acagatctac    1260

gtgtgtggag gctatgacgg caactcctcc ctcaactctg tggagaccta ctcacctgag   1320

acggacaagt aa                                                       1332
```

<210> SEQ ID NO 9
<211> LENGTH: 443
<212> TYPE: PRT
<213> ORGANISM: Mus musculus

<400> SEQUENCE: 9

```
Met Val Glu Asp Gly Ala Glu Glu Leu Glu Asp Leu Val His Phe Ser
1               5                   10                  15

Val Ser Glu Leu Pro Ser Arg Gly Tyr Gly Val Met Glu Glu Ile Arg
            20                  25                  30

Arg Gln Gly Lys Leu Cys Asp Val Thr Leu Lys Ile Gly Asp His Lys
        35                  40                  45

Phe Ser Ala His Arg Ile Val Leu Ala Ala Ser Ile Pro Tyr Phe His
    50                  55                  60

Ala Met Phe Thr Asn Asp Met Met Glu Cys Lys Gln Asp Glu Ile Val
65                  70                  75                  80

Met Gln Gly Met Asp Pro Ser Ala Leu Glu Ala Leu Ile Asn Phe Ala
                85                  90                  95

Tyr Asn Gly Asn Leu Ala Ile Asp Gln Gln Asn Val Gln Ser Leu Leu
            100                 105                 110

Met Gly Ala Ser Phe Leu Gln Leu Gln Ser Ile Lys Asp Ala Cys Cys
        115                 120                 125

Thr Phe Leu Arg Glu Arg Leu His Pro Lys Asn Cys Leu Gly Val Arg
    130                 135                 140

Gln Phe Ala Glu Thr Met Met Cys Ala Val Leu Tyr Asp Ala Ala Asn
145                 150                 155                 160

Ser Phe Ile His Gln His Phe Val Glu Val Ser Leu Ser Glu Glu Phe
                165                 170                 175

Leu Ala Leu Pro Leu Glu Asp Val Leu Glu Leu Val Ser Arg Asp Glu
            180                 185                 190

Leu Asn Val Lys Ser Glu Glu Gln Ser Glu His Val Gln Arg Arg Glu
        195                 200                 205

Glu Leu Gly Thr Gly Met Glu Asp Thr His Val Ala Ile Ser Arg Thr
    210                 215                 220

Gln Val Ser Arg Glu Val Phe Glu Ala Ala Leu Ala Trp Val Arg Tyr
225                 230                 235                 240

Asp Arg Glu Gln Arg Gly Pro Cys Leu Pro Glu Leu Leu Ser Asn Ile
```

```
                245                 250                 255

Arg Leu Pro Leu Cys Arg Pro Gln Phe Leu Ser Asp Arg Val Gln Gln
            260                 265                 270

Asp Asp Leu Val Arg Cys Cys His Lys Cys Arg Asp Leu Val Asp Glu
        275                 280                 285

Ala Lys Asp Tyr His Leu Met Pro Glu Arg Arg Pro His Leu Pro Ala
    290                 295                 300

Phe Arg Thr Arg Pro Arg Cys Cys Thr Ser Ile Ala Gly Leu Ile Tyr
305                 310                 315                 320

Ala Val Gly Gly Leu Asn Ser Ala Ala Asn Phe Tyr Ala Gly Asp Ser
                325                 330                 335

Leu Asn Val Val Glu Val Phe Asp Pro Ile Ala Asn Arg Trp Glu Lys
            340                 345                 350

Cys His Pro Met Thr Thr Ala Arg Ser Arg Val Gly Val Ala Val Val
        355                 360                 365

Asn Gly Leu Leu Tyr Ala Ile Gly Gly Tyr Asp Gly Gln Leu Arg Leu
    370                 375                 380

Ser Thr Val Glu Ala Tyr Asn Pro Glu Thr Asp Thr Trp Thr Arg Val
385                 390                 395                 400

Gly Ser Met Asn Ser Lys Arg Ser Ala Met Gly Thr Val Val Leu Asp
                405                 410                 415

Gly Gln Ile Tyr Val Cys Gly Gly Tyr Asp Gly Asn Ser Ser Leu Asn
            420                 425                 430

Ser Val Glu Thr Tyr Ser Pro Glu Thr Asp Lys
        435                 440


<210> SEQ ID NO 10
<211> LENGTH: 4743
<212> TYPE: DNA
<213> ORGANISM: Homo sapiens

<400> SEQUENCE: 10

gcggccgcgg aggcccgtcc gattgctgct ccgcgctccg agcggctgtc ggcgtgcgct     60

atcgccccgc cctggttagt gtctagccgg ccggcgaggc ctgcgcagtt gcagcggccg    120

gggaagatgg tggaggacgg cgcggaggag ctggaggatc tggtgcactt ctccgtgtct    180

gagttgccta gtcgcggcta cggcgtcatg gaggagatcc ggcggcaggg caagctgtgc    240

gacgtgaccc tcaagattgg ggaccacaaa ttcagtgccc accggattgt cttagcagcc    300

tcgatcccgt atttccatgc tatgtttaca aatgacatga tggagtgcaa gcaggatgag    360

attgtaatgc aaggaatgga cccaagtgcc ctggaggctc tgatcaactt tgcctacaac    420

ggcaaccttg ccattgacca gcaaaatgtc cagtcattgc tgatgggggc gagcttcctg    480

cagctgcaga gcatcaaaga cgcctgctgc acattccttc gagaacggct tcacccaaaa    540

aactgcctgg gtgtgcgcca gtttgctgag acaatgatgt gtgctgtgct gtacgacgct    600

gccaacagct tcatccacca gcactttgtg gaggtgtcca tgtcagaaga gttcctggcc    660

ctgcccttgg aagacgtgct tgagctggtg tctcgggatg agctgaatgt caaatctgag    720

gagcaggtct ttgaagctgc attggcctgg gtcagatacg accgggagca gaggggtccc    780

tacctgcctg agctgctgtc caatatccgc ctgcccctct gtcggcccca gttcctttca    840

gacagagtac agcaggatga cctggtgcgt tgctgccaca aatgcaggga cctggtagac    900

gaagcaaagg actaccacct catgccagag cgccggcccc acctgccagc tttcagaacc    960

cggccacgct gctgcacatc catcgctgga cttatctacg ctgtaggggg cctcaactca   1020
```

```
gcaggtgatt ccctgaatgt ggtggaagtg ttcgacccca ttgccaattg ctgggagaga   1080
tgccgtccca tgacaacagc ccgcagccgc gttggcgtgg ctgtggtgaa cgggcttctc   1140
tatgccatcg gaggatatga cggccagcta cggctgagca ctgtggaggc ctacaacccg   1200
gagacagaca catggaccag agtggggagc atgaatagca agagaagtgc catggggaca   1260
gtcgtgctgg atgggcagat ctacgtctgt gggggctacg atggcaactc ttccctcagc   1320
tccgtggaga cctactcacc tgagacggac aaatggacag tggtgacctc gatgagctcg   1380
aatcgcagtg ctgctggggt tacagtcttt gagggcagga tatatgtgtc aggcggccat   1440
gatggtttgc agatcttcag cagtgtggaa cactacaacc accacacagc cacctggcac   1500
cctgcagctg gcatgctcaa caagcgctgc cggcacggag ccgcctccct ggggagcaag   1560
atgtttgtct gcgggggcta cgatggctct ggcttcctca gcattgccga gatgtacagc   1620
tctgtggcag accagtggtg cctgattgtc cccatgcaca cgcgcaggag ccgggtctcc   1680
ctggtggcca gctgtgggcg cctctacgct gttgggggct acgacggaca gtcaaaccta   1740
agctcagtgg agatgtatga cccagagaca gactgctgga cattcatggc ccccatggcg   1800
tgccatgagg gaggggtcgg tgtgggctgc atccctctcc tcaccatcta aggcagagga   1860
tgggatgtgg tggggcaggg atctggtaca gacataggcg cttccttcca ggaacagtcc   1920
ctcaggagag gcagtggacc agaagagatg gcgaaacgtg agctcgccgg aggtacagtt   1980
tttccaggtg cttaagccct cccccactgt gccacccttg tgaccttcag gcttgggtca   2040
tcaagatgca cagcatggaa cacaagctcc tctggatcct gcagctggtg acatggaact   2100
gttttctggt ccacatgaac acaggctcca tccaggccca gctcctaccc accgcctctc   2160
tgtgggccag ctgttcacag aaggccttcc atctgatgct ccccatcgcc tgcttgctct   2220
ccagccgagt ctggccaatt tgccatgggg aggctgcagt gtccaagcct gctggaaact   2280
gggatgtagc tggggacgaa aggacagacc caagcgttct ccctgcctga gatggtgtgg   2340
ccacagcagt ggaaggctgc acacaggcac attccttctt ccacagtggg gcaccaagga   2400
ttctgtcctc attgctgggt aagcagggag aagagaagtt ttccccatgt ctaattttgg   2460
gatttcagtg aggccttttc catctgtcca ggagaacaga agggaaaaaa agatacttga   2520
aagaaactga aggaaattta aacaaagaaa cacttgaaag aaactggaaa gaaaaataat   2580
tttttatgt gaacaaattt tgcaagaaga aaaaagcata aaagacacta acggcaaatc   2640
tatgtttaaa tggaaaatcg tctaactgga gaagggcggt atccacccca cattcggatc   2700
ccagggtcct gaggcctcgc attgagctgg gggttccctc tgagccccag tgtgtgtgga   2760
atcagtgcac tcttgactgg gcctgtagta aggtgctcat ggggtttgtc ttctcaccca   2820
ccatcagagg acttttaaaa tcataggcgt agagagttag ctatctgctg aattactgcc   2880
actcttcttg gtgggggctc ctagctgtgg ctgggggctc caggcgcccc tgtgattacc   2940
tcctactgcc accatggcgc tcattcagat tccccactct cactaacatt gcttcctttt   3000
ttgaccagca ggaaacagca ggtctggcca gattctcact tgcccatcaa tctcgttctt   3060
ggatgatttc cctcattgtg atgcttctgg ggcacgttga ccatatgcac ctctagaacc   3120
taaccagggc ttccttctac cagctgtggg cgggcttggt ctggtaacct tgtctgctct   3180
gccattccac tgctcctcca tccactcgcc aatcccaaga gtctggcctc cctccagccc   3240
tgggcagact gaccagcaag gtggaccttt acattcaagc acagctggct tttatgacat   3300
aaagaactaa aggccgaaag aatctcttgc tgctgcaaag aacagatttt atatttcttc   3360
```

```
ctctaatctt ggcaaatgac ctttaccttt tggaaagatt tcatattgct tcctcctccc   3420

tggataggac ctaatgtagc acagcgggac tcaaagagga ggacattttc tcttgccagt   3480

gcactgggca gtggggctgt ccttcaactg ctgctgccaa aattggtttt ctaaaattct   3540

tccagtagag actaaaagaa gattcaattc ctgtaaccca agactgagtc ttagggctcc   3600

agtctccacc tgcttggttt cctatccttt gctgcctgcc tggggtggcc tggaagcctg   3660

ttcagaaagg cacaatgtgg agcctggggt gtctccccca ccccaggacc gtcaggttta   3720

ccagtgtgtg caatcgccat gtattcagag ggaagtacct ttgttaccta caacttagga   3780

gctaggcctc tgctacaagc acttgaaaat gatattttta tttttaacgt ctcaacaatc   3840

tgatatcgga tgtcgtttaa cctgggctcg tggtagggct ccagcatttc tccctccttc   3900

ctggtttgcc tgtaggggta gactcggaag gtgggtgggg tgtgcatttc ctgttaggag   3960

tgtatcagtg cttgtcttat tataagcccc tttcttttgt gaatttgaag tagcaccaac   4020

aagcctggat tgtgaaggta ttaagaatcg gtctgtgggc tactgagtgg gtccttagga   4080

tactggccca gattttgcca ctgggtatgg cagatcattt tctaccatgg cctgctgctc   4140

ttgtagtgga cttcctgagt ccaatcccac ctcctggtgt agaatttaca ctgctgcacc   4200

tgaggtcgat gtttcaaagt aagatcaagc cagtgttttg atctgggctc tgagcacaag   4260

tcaggaaaca ccaacatatt cacactctcc cagtaggttc ctcagtccga tggtgaatgg   4320

ctattcgtaa atggctggtc tggctctttg gtgttggagc ctttccaata gccccatgaa   4380

aagaagcatc acccaaggat attgtaaaaa ggatgtaaca aggagatagg gtagacattg   4440

tactcagtgg gccttggggc ctagcccagc tctgagcaga ggactgtggc attcactgtc   4500

cttgagtgtt tcaccttctt ggataacaca cgggccttct cttctggatt tcatcagaga   4560

ttacagccag atgggggctg aagaccatcc tcttgaccac agaggtgtga ctgtgggaat   4620

tcctcccaat ttatggtttc ccagaaaatc ttagttcctt ttatttatag aatgcatgtc   4680

ttttgtgtta agaaaccaaa gagaaataaa gagaacactc ctaataaaaa aaaaaaaaaa   4740

aaa                                                                 4743
```

<210> SEQ ID NO 11
<211> LENGTH: 1725
<212> TYPE: DNA
<213> ORGANISM: Homo sapiens

<400> SEQUENCE: 11

```
atggtggagg acggcgcgga ggagctggag gatctggtgc acttctccgt gtctgagttg     60

cctagtcgcg gctacggcgt catggaggag atccggcggc agggcaagct gtgcgacgtg    120

accctcaaga ttggggacca caaattcagt gcccaccgga ttgtcttagc agcctcgatc    180

ccgtatttcc atgctatgtt tacaaatgac atgatggagt gcaagcagga tgagattgta    240

atgcaaggaa tggacccaag tgccctggag gctctgatca actttgccta caacggcaac    300

cttgccattg accagcaaaa tgtccagtca ttgctgatgg gggcgagctt cctgcagctg    360

cagagcatca aagacgcctg ctgcacattc cttcgagaac ggcttcaccc aaaaaactgc    420

ctgggtgtgc gccagtttgc tgagacaatg atgtgtgctg tgctgtacga cgctgccaac    480

agcttcatcc accagcactt tgtggaggtg tccatgtcag aagagttcct ggccctgccc    540

ttggaagacg tgcttgagct ggtgtctcgg gatgagctga atgtcaaatc tgaggagcag    600

gtctttgaag ctgcattggc ctgggtcaga tacgaccggg agcagagggg tccctacctg    660

cctgagctgc tgtccaatat ccgcctgccc ctctgtcggc cccagttcct ttcagacaga    720
```

```
gtacagcagg atgacctggt gcgttgctgc cacaaatgca gggacctggt agacgaagca    780

aaggactacc acctcatgcc agagcgccgg ccccacctgc cagctttcag aacccggcca    840

cgctgctgca catccatcgc tggacttatc tacgctgtag ggggcctcaa ctcagcaggt    900

gattccctga atgtggtgga agtgttcgac cccattgcca attgctggga gagatgccgt    960

cccatgacaa cagcccgcag ccgcgttggc gtggctgtgg tgaacgggct tctctatgcc   1020

atcggaggat atgacggcca gctacggctg agcactgtgg aggcctacaa cccggagaca   1080

gacacatgga ccagagtggg gagcatgaat agcaagagaa gtgccatggg gacagtcgtg   1140

ctggatgggc agatctacgt ctgtgggggc tacgatggca actcttccct cagctccgtg   1200

gagacctact cacctgagac ggacaaatgg acagtggtga cctcgatgag ctcgaatcgc   1260

agtgctgctg gggttacagt ctttgagggc aggatatatg tgtcaggcgg ccatgatggt   1320

ttgcagatct tcagcagtgt ggaacactac aaccaccaca cagccacctg gcaccctgca   1380

gctggcatgc tcaacaagcg ctgccggcac ggagccgcct ccctggggag caagatgttt   1440

gtctgcgggg gctacgatgg ctctggcttc ctcagcattg ccgagatgta cagctctgtg   1500

gcagaccagt ggtgcctgat tgtccccatg cacacgcgca ggagccgggt ctccctggtg   1560

gccagctgtg ggcgcctcta cgctgttggg ggctacgacg gacagtcaaa cctaagctca   1620

gtggagatgt atgacccaga gacagactgc tggacattca tggcccccat ggcgtgccat   1680

gagggagggg tcggtgtggg ctgcatccct ctcctcacca tctaa                   1725
```

<210> SEQ ID NO 12
<211> LENGTH: 574
<212> TYPE: PRT
<213> ORGANISM: Homo sapiens

<400> SEQUENCE: 12

```
Met Val Glu Asp Gly Ala Glu Glu Leu Glu Asp Leu Val His Phe Ser
1               5                   10                  15

Val Ser Glu Leu Pro Ser Arg Gly Tyr Gly Val Met Glu Glu Ile Arg
            20                  25                  30

Arg Gln Gly Lys Leu Cys Asp Val Thr Leu Lys Ile Gly Asp His Lys
        35                  40                  45

Phe Ser Ala His Arg Ile Val Leu Ala Ala Ser Ile Pro Tyr Phe His
    50                  55                  60

Ala Met Phe Thr Asn Asp Met Met Glu Cys Lys Gln Asp Glu Ile Val
65                  70                  75                  80

Met Gln Gly Met Asp Pro Ser Ala Leu Glu Ala Leu Ile Asn Phe Ala
                85                  90                  95

Tyr Asn Gly Asn Leu Ala Ile Asp Gln Gln Asn Val Gln Ser Leu Leu
            100                 105                 110

Met Gly Ala Ser Phe Leu Gln Leu Gln Ser Ile Lys Asp Ala Cys Cys
        115                 120                 125

Thr Phe Leu Arg Glu Arg Leu His Pro Lys Asn Cys Leu Gly Val Arg
    130                 135                 140

Gln Phe Ala Glu Thr Met Met Cys Ala Val Leu Tyr Asp Ala Ala Asn
145                 150                 155                 160

Ser Phe Ile His Gln His Phe Val Glu Val Ser Met Ser Glu Glu Phe
                165                 170                 175

Leu Ala Leu Pro Leu Glu Asp Val Leu Glu Leu Val Ser Arg Asp Glu
            180                 185                 190
```

```
Leu Asn Val Lys Ser Glu Glu Gln Val Phe Glu Ala Ala Leu Ala Trp
        195                 200                 205

Val Arg Tyr Asp Arg Glu Gln Arg Gly Pro Tyr Leu Pro Glu Leu Leu
    210                 215                 220

Ser Asn Ile Arg Leu Pro Leu Cys Arg Pro Gln Phe Leu Ser Asp Arg
225                 230                 235                 240

Val Gln Gln Asp Asp Leu Val Arg Cys Cys His Lys Cys Arg Asp Leu
                245                 250                 255

Val Asp Glu Ala Lys Asp Tyr His Leu Met Pro Glu Arg Arg Pro His
            260                 265                 270

Leu Pro Ala Phe Arg Thr Arg Pro Arg Cys Cys Thr Ser Ile Ala Gly
        275                 280                 285

Leu Ile Tyr Ala Val Gly Gly Leu Asn Ser Ala Gly Asp Ser Leu Asn
    290                 295                 300

Val Val Glu Val Phe Asp Pro Ile Ala Asn Cys Trp Glu Arg Cys Arg
305                 310                 315                 320

Pro Met Thr Thr Ala Arg Ser Arg Val Gly Val Ala Val Val Asn Gly
                325                 330                 335

Leu Leu Tyr Ala Ile Gly Gly Tyr Asp Gly Gln Leu Arg Leu Ser Thr
            340                 345                 350

Val Glu Ala Tyr Asn Pro Glu Thr Asp Thr Trp Thr Arg Val Gly Ser
        355                 360                 365

Met Asn Ser Lys Arg Ser Ala Met Gly Thr Val Val Leu Asp Gly Gln
    370                 375                 380

Ile Tyr Val Cys Gly Gly Tyr Asp Gly Asn Ser Ser Leu Ser Ser Val
385                 390                 395                 400

Glu Thr Tyr Ser Pro Glu Thr Asp Lys Trp Thr Val Val Thr Ser Met
                405                 410                 415

Ser Ser Asn Arg Ser Ala Ala Gly Val Thr Val Phe Glu Gly Arg Ile
            420                 425                 430

Tyr Val Ser Gly Gly His Asp Gly Leu Gln Ile Phe Ser Ser Val Glu
        435                 440                 445

His Tyr Asn His His Thr Ala Thr Trp His Pro Ala Ala Gly Met Leu
    450                 455                 460

Asn Lys Arg Cys Arg His Gly Ala Ala Ser Leu Gly Ser Lys Met Phe
465                 470                 475                 480

Val Cys Gly Gly Tyr Asp Gly Ser Gly Phe Leu Ser Ile Ala Glu Met
                485                 490                 495

Tyr Ser Ser Val Ala Asp Gln Trp Cys Leu Ile Val Pro Met His Thr
            500                 505                 510

Arg Arg Ser Arg Val Ser Leu Val Ala Ser Cys Gly Arg Leu Tyr Ala
        515                 520                 525

Val Gly Gly Tyr Asp Gly Gln Ser Asn Leu Ser Ser Val Glu Met Tyr
    530                 535                 540

Asp Pro Glu Thr Asp Cys Trp Thr Phe Met Ala Pro Met Ala Cys His
545                 550                 555                 560

Glu Gly Gly Val Gly Val Gly Cys Ile Pro Leu Leu Thr Ile
                565                 570
```

<210> SEQ ID NO 13
<211> LENGTH: 4656
<212> TYPE: DNA
<213> ORGANISM: Homo sapiens

<400> SEQUENCE: 13

```
ctgcgcagtt gcagcggccg gggaagatgg tggaggacgg cgcggaggag ctggaggatc     60
tggtgcactt ctccgtgtct gagttgccta gtcgcggcta cggcgtcatg gaggagatcc    120
ggcggcaggg caagctgtgc gacgtgaccc tcaagattgg ggaccacaaa ttcagtgccc    180
accggattgt cttagcagcc tcgatcccgt atttccatgc tatgtttaca aatgacatga    240
tggagtgcaa gcaggatgag attgtaatgc aaggaatgga cccaagtgcc ctggaggctc    300
tgatcaactt tgcctacaac ggcaaccttg ccattgacca gcaaaatgtc cagtcattgc    360
tgatgggggc gagcttcctg cagctgcaga gcatcaaaga cgcctgctgc acattccttc    420
gagaacggct tcacccaaaa aactgcctgg gtgtgcgcca gtttgctgag acaatgatgt    480
gtgctgtgct gtacgacgct gccaacagct tcatccacca gcactttgtg gaggtgtcca    540
tgtcagaaga gttcctggcc ctgcccttgg aagacgtgct tgagctggtg tctcgggatg    600
agctgaatgt caaatctgag gagcaggtct ttgaagctgc attggcctgg gtcagatacg    660
accgggagca gaggggtccc tacctgcctg agctgctgtc caatatccgc ctgcccctct    720
gtcggcccca gttcctttca gacagagtac agcaggatga cctggtgcgt tgctgccaca    780
aatgcaggga cctggtagac gaagcaaagg actaccacct catgccagag cgccggcccc    840
acctgccagc tttcagaacc cggccacgct gctgcacatc catcgctgga cttatctacg    900
ctgtaggggg cctcaactca gcagcaaatt tttatgcagg tgattccctg aatgtggtgg    960
aagtgttcga ccccattgcc aattgctggg agagatgccg tcccatgaca acagcccgca   1020
gccgcgttgg cgtggctgtg gtgaacgggc ttctctatgc catcggagga tatgacggcc   1080
agctacggct gagcactgtg gaggcctaca acccggagac agacacatgg accagagtgg   1140
ggagcatgaa tagcaagaga agctctgtct gtttcagtgc catggggaca gtcgtgctgg   1200
atgggcagat ctacgtctgt gggggctacg atggcaactc ttccctcagc tccgtggaga   1260
cctactcacc tgagacggac aaatggacag tggtgacctc gatgagctcg aatcgcagtg   1320
ctgctggggt tacagtcttt gagggcagga tatatgtgtc aggcggccat gatggtttgc   1380
agatcttcag cagtgtggaa cactacaacc accacacagc cacctggcac cctgcagctg   1440
gcatgctcaa caagcgctgc cggcacggag ccgcctccct ggggagcaag atgtttgtct   1500
gcgggggcta cgatggctct ggcttcctca gcattgccga gatgtacagc tctgtggcag   1560
accagtggtg cctgattgtc cccatgcaca cgcgcaggag ccgggtctcc ctggtggcca   1620
gctgtgggcg cctctacgct gttgggggct acgacggaca gtcaaaccta agctcagtgg   1680
agatgtatga cccagagaca gactgctgga cattcatggc ccccatggcg tgccatgagg   1740
gaggggtcgg tgtgggctgc atccctctcc tcaccatcta aggcagagga tgggatgtgg   1800
tggggcaggg atctggtaca gacataggcg cttccttcca ggaacagtcc ctcaggagag   1860
gcagtggacc agaagagatg gcgaaacgtg agctcgccgg aggtacagtt tttccaggtg   1920
cttaagccct cccccactgt gccacccttg tgaccttcag gcttgggtca tcaagatgca   1980
cagcatggaa cacaagctcc tctggatcct gcagctggtg acatggaact gttttctggt   2040
ccacatgaac acaggctcca tccaggccca gctcctaccc accgcctctc tgtgggccag   2100
ctgttcacag aaggccttcc atctgatgct ccccatcgcc tgcttgctct ccagccgagt   2160
ctggccaatt tgccatgggg aggctgcagt gtccaagcct gctggaaact gggatgtagc   2220
tggggacgaa aggacagacc caagcgttct ccctgcctga gatggtgtgg ccacagcagt   2280
ggaaggctgc acacaggcac attccttctt ccacagtggg gcaccaagga ttctgtcctc   2340
```

-continued

```
attgctgggt aagcagggag aagagaagtt ttccccatgt ctaattttgg gatttcagtg   2400
aggccttttg atctgtccag gagaacagaa gggaaaaaaa gatacttgaa agaaactgaa   2460
ggaaatttaa acaaagaaac acttgaaaga aactggaaag aaaaataatt tttttatgtg   2520
aacaaatttt gcaagaagaa aaaagcataa aagacactaa cggcaaatct atgtttaaat   2580
ggaaaatcgt ctaactggag aagggcggta tccaccccac attcggatcc cagggtcctg   2640
aggcctcgca ttgagctggg ggttccctct gagccccagt gtgtgtggaa tcagtgcact   2700
cttgactggg cctgtagtaa ggtgctcatg ggtttgtct tctcacccac catcagagga    2760
cttttaaaat cataggcgta gagagttagg ctatctgctg aattactgcc actcttcttg   2820
gtgggggctc ctagctgtgg ctgggggctc caggcgcccc tgtgattacc tcctactgcc   2880
accatggcgc tcattcagat tccccactct cactaacatt gcttcctttt ttgaccagca   2940
ggaaacagca ggtctggcca gattctcact tgcccatcaa tctcgttctt ggatgatttc   3000
cctcattgtg atgcttctgg ggcacgttga ccatatgcac ctctagaacc taaccagggc   3060
ttccttctac cagctgtggg cgggcttggt ctggtaacct tgtctgctct gccattccac   3120
tgctcctcca tccactcgcc aatcccaaga gtctggcctc cctccagccc tgggcagact   3180
gaccagcaag gtggaccttt acattcaagc acagctggct tttatgacat aaagaactaa   3240
aggccgaaag aatctcttgc tgctgcaaag aacagatttt atatttcttc ctctaatctt   3300
ggcaaatgac ctttaccttt tggaaagatt tcatattgct tcctcctccc tggataggac   3360
ctaatgtagc acagcgggac tcaaagagga ggacattttc tcttgccagt gcactgggca   3420
gtggggctgt ccttcaactg ctgctgccaa aattggtttt ctaaaattct tccagtagag   3480
actaaaagaa gattcaattc ctgtaaccca agactgagtc ttagggctcc agtctccacc   3540
tgcttggttt cctatccttt gctgcctgcc tggggtggcc tggaagcctg ttcagaaagg   3600
cacaatgtgg agcctggggt gtctccccca ccccaggacc gtcaggttta ccagtgtgtg   3660
caatcgccat gtattcagag ggaagtacct ttgttaccta caacttagga gctaggcctc   3720
tgctacaagc acttgaaaat gatattttta tttttaacgt ctcaacaatc tgatatcgga   3780
tgtcgtttaa cctgggctcg tggtagggct ccagcatttc tccctccttc ctggtttgcc   3840
tgtaggggta gactcggaag gtgggtgggg tgtgcatttc ctgttaggag tgtatcagtg   3900
cttgtcttat tataagcccc tttcttttgt gaatttgaag tagcaccaac aagcctggat   3960
tgtgaaggta ttaagaatcg gtctgtgggc tactgagtgg gtccttagga tactggccca   4020
gattttgcca ctgggtatgg cagatcattt tctaccatgg cctgctgctc ttgtagtgga   4080
cttcctgagt ccaatcccac ctcctggtgt agaatttaca ctgctgcacc tgaggtcgat   4140
gtttcaaagt aagatcaagc cagtgttttg atctgggctc tgagcacaag tcaggaaaca   4200
ccaacatatt cacactctcc cagtaggttc ctcagtccga tggtgaatgg ctattcgtaa   4260
atggctggtc tggctctttg gtgttggagc ctttccaata gccccatgaa aagaagcatc   4320
acccaaggat attgtaaaaa ggatgtaaca aggagatagg gtagacattg tactcagtgg   4380
gccttggggc ctagcccagc tctgagcaga ggactgtggc attcactgtc cttgagtgtt   4440
tcaccttctt ggataacaca cgggccttct cttctggatt tcatcagaga ttacagccag   4500
atgggggctg aagaccatcc tcttgaccac agaggtgtga ctgtgggaat tcctcccaat   4560
ttatggtttc ccagaaaatc ttagttcctt ttatttatag aatgcatgtc ttttgtgtta   4620
agaaaccaaa gagaaataaa gagaacactc ctaata                              4656
```

<210> SEQ ID NO 14
<211> LENGTH: 1755
<212> TYPE: DNA
<213> ORGANISM: Homo sapiens

<400> SEQUENCE: 14

```
atggtggagg acggcgcgga ggagctggag gatctggtgc acttctccgt gtctgagttg     60

cctagtcgcg gctacggcgt catggaggag atccggcggc agggcaagct gtgcgacgtg    120

accctcaaga ttggggacca caaattcagt gcccaccgga ttgtcttagc agcctcgatc    180

ccgtatttcc atgctatgtt tacaaatgac atgatggagt gcaagcagga tgagattgta    240

atgcaaggaa tggacccaag tgccctggag gctctgatca actttgccta caacggcaac    300

cttgccattg accagcaaaa tgtccagtca ttgctgatgg gggcgagctt cctgcagctg    360

cagagcatca aagacgcctg ctgcacattc cttcgagaac ggcttcaccc aaaaaactgc    420

ctgggtgtgc gccagtttgc tgagacaatg atgtgtgctg tgctgtacga cgctgccaac    480

agcttcatcc accagcactt tgtggaggtg tccatgtcag aagagttcct ggccctgccc    540

ttggaagacg tgcttgagct ggtgtctcgg gatgagctga atgtcaaatc tgaggagcag    600

gtctttgaag ctgcattggc ctgggtcaga tacgaccggg agcagagggg tccctacctg    660

cctgagctgc tgtccaatat ccgcctgccc ctctgtcggc cccagttcct ttcagacaga    720

gtacagcagg atgacctggt gcgttgctgc cacaaatgca gggacctggt agacgaagca    780

aaggactacc acctcatgcc agagcgccgg ccccacctgc cagctttcag aacccggcca    840

cgctgctgca catccatcgc tggacttatc tacgctgtag gggcctcaa ctcagcagca    900

aatttttatg caggtgattc cctgaatgtg gtggaagtgt tcgaccccat tgccaattgc    960

tgggagagat gccgtcccat gacaacagcc cgcagccgcg ttggcgtggc tgtggtgaac   1020

gggcttctct atgccatcgg aggatatgac ggccagctac ggctgagcac tgtggaggcc   1080

tacaacccgg agacagacac atggaccaga gtggggagca tgaatagcaa gagaagctct   1140

gtctgtttca gtgccatggg gacagtcgtg ctggatgggc agatctacgt ctgtgggggc   1200

tacgatggca actcttccct cagctccgtg gagacctact cacctgagac ggacaaatgg   1260

acagtggtga cctcgatgag ctcgaatcgc agtgctgctg gggttacagt ctttgagggc   1320

aggatatatg tgtcaggcgg ccatgatggt ttgcagatct tcagcagtgt ggaacactac   1380

aaccaccaca cagccacctg gcaccctgca gctggcatgc tcaacaagcg ctgccggcac   1440

ggagccgcct ccctggggag caagatgttt gtctgcgggg gctacgatgg ctctggcttc   1500

ctcagcattg ccgagatgta cagctctgtg gcagaccagt ggtgcctgat tgtccccatg   1560

cacacgcgca ggagccgggt ctccctggtg gccagctgtg ggcgcctcta cgctgttggg   1620

ggctacgacg gacagtcaaa cctaagctca gtggagatgt atgacccaga gacagactgc   1680

tggacattca tggcccccat ggcgtgccat gagggagggg tcggtgtggg ctgcatccct   1740

ctcctcacca tctaa                                                    1755
```

<210> SEQ ID NO 15
<211> LENGTH: 584
<212> TYPE: PRT
<213> ORGANISM: Homo sapiens

<400> SEQUENCE: 15

```
Met Val Glu Asp Gly Ala Glu Glu Leu Glu Asp Leu Val His Phe Ser
1               5                   10                  15

Val Ser Glu Leu Pro Ser Arg Gly Tyr Gly Val Met Glu Glu Ile Arg
```

-continued

```
            20                  25                  30

Arg Gln Gly Lys Leu Cys Asp Val Thr Leu Lys Ile Gly Asp His Lys
        35                  40                  45

Phe Ser Ala His Arg Ile Val Leu Ala Ala Ser Ile Pro Tyr Phe His
    50                  55                  60

Ala Met Phe Thr Asn Asp Met Met Glu Cys Lys Gln Asp Glu Ile Val
65                  70                  75                  80

Met Gln Gly Met Asp Pro Ser Ala Leu Glu Ala Leu Ile Asn Phe Ala
                85                  90                  95

Tyr Asn Gly Asn Leu Ala Ile Asp Gln Gln Asn Val Gln Ser Leu Leu
            100                 105                 110

Met Gly Ala Ser Phe Leu Gln Leu Gln Ser Ile Lys Asp Ala Cys Cys
        115                 120                 125

Thr Phe Leu Arg Glu Arg Leu His Pro Lys Asn Cys Leu Gly Val Arg
    130                 135                 140

Gln Phe Ala Glu Thr Met Met Cys Ala Val Leu Tyr Asp Ala Ala Asn
145                 150                 155                 160

Ser Phe Ile His Gln His Phe Val Glu Val Ser Met Ser Glu Glu Phe
                165                 170                 175

Leu Ala Leu Pro Leu Glu Asp Val Leu Glu Leu Val Ser Arg Asp Glu
            180                 185                 190

Leu Asn Val Lys Ser Glu Glu Gln Val Phe Glu Ala Ala Leu Ala Trp
        195                 200                 205

Val Arg Tyr Asp Arg Glu Gln Arg Gly Pro Tyr Leu Pro Glu Leu Leu
    210                 215                 220

Ser Asn Ile Arg Leu Pro Leu Cys Arg Pro Gln Phe Leu Ser Asp Arg
225                 230                 235                 240

Val Gln Gln Asp Asp Leu Val Arg Cys Cys His Lys Cys Arg Asp Leu
                245                 250                 255

Val Asp Glu Ala Lys Asp Tyr His Leu Met Pro Glu Arg Arg Pro His
            260                 265                 270

Leu Pro Ala Phe Arg Thr Arg Pro Arg Cys Cys Thr Ser Ile Ala Gly
        275                 280                 285

Leu Ile Tyr Ala Val Gly Gly Leu Asn Ser Ala Ala Asn Phe Tyr Ala
    290                 295                 300

Gly Asp Ser Leu Asn Val Val Glu Val Phe Asp Pro Ile Ala Asn Cys
305                 310                 315                 320

Trp Glu Arg Cys Arg Pro Met Thr Thr Ala Arg Ser Arg Val Gly Val
                325                 330                 335

Ala Val Val Asn Gly Leu Leu Tyr Ala Ile Gly Gly Tyr Asp Gly Gln
            340                 345                 350

Leu Arg Leu Ser Thr Val Glu Ala Tyr Asn Pro Glu Thr Asp Thr Trp
        355                 360                 365

Thr Arg Val Gly Ser Met Asn Ser Lys Arg Ser Ser Val Cys Phe Ser
    370                 375                 380

Ala Met Gly Thr Val Val Leu Asp Gly Gln Ile Tyr Val Cys Gly Gly
385                 390                 395                 400

Tyr Asp Gly Asn Ser Ser Leu Ser Ser Val Glu Thr Tyr Ser Pro Glu
                405                 410                 415

Thr Asp Lys Trp Thr Val Val Thr Ser Met Ser Ser Asn Arg Ser Ala
            420                 425                 430

Ala Gly Val Thr Val Phe Glu Gly Arg Ile Tyr Val Ser Gly Gly His
        435                 440                 445
```

```
Asp Gly Leu Gln Ile Phe Ser Ser Val Glu His Tyr Asn His His Thr
    450                 455                 460

Ala Thr Trp His Pro Ala Ala Gly Met Leu Asn Lys Arg Cys Arg His
465                 470                 475                 480

Gly Ala Ala Ser Leu Gly Ser Lys Met Phe Val Cys Gly Gly Tyr Asp
                485                 490                 495

Gly Ser Gly Phe Leu Ser Ile Ala Glu Met Tyr Ser Ser Val Ala Asp
            500                 505                 510

Gln Trp Cys Leu Ile Val Pro Met His Thr Arg Arg Ser Arg Val Ser
        515                 520                 525

Leu Val Ala Ser Cys Gly Arg Leu Tyr Ala Val Gly Gly Tyr Asp Gly
    530                 535                 540

Gln Ser Asn Leu Ser Ser Val Glu Met Tyr Asp Pro Glu Thr Asp Cys
545                 550                 555                 560

Trp Thr Phe Met Ala Pro Met Ala Cys His Glu Gly Gly Val Gly Val
                565                 570                 575

Gly Cys Ile Pro Leu Leu Thr Ile
            580


<210> SEQ ID NO 16
<211> LENGTH: 4641
<212> TYPE: DNA
<213> ORGANISM: Homo sapiens

<400> SEQUENCE: 16

ctgcgcagtt gcagcggccg gggaagatgg tggaggacgg cgcggaggag ctggaggatc      60

tggtgcactt ctccgtgtct gagttgccta gtcgcggcta cggcgtcatg gaggagatcc     120

ggcggcaggg caagctgtgc gacgtgaccc tcaagattgg ggaccacaaa ttcagtgccc     180

accggattgt cttagcagcc tcgatcccgt atttccatgc tatgtttaca aatgacatga     240

tggagtgcaa gcaggatgag attgtaatgc aaggaatgga cccaagtgcc ctggaggctc     300

tgatcaactt tgcctacaac ggcaaccttg ccattgacca gcaaaatgtc cagtcattgc     360

tgatgggggc gagcttcctg cagctgcaga gcatcaaaga cgcctgctgc acattccttc     420

gagaacggct tcacccaaaa aactgcctgg gtgtgcgcca gtttgctgag acaatgatgt     480

gtgctgtgct gtacgacgct gccaacagct tcatccacca gcactttgtg gaggtgtcca     540

tgtcagaaga gttcctggcc ctgcccttgg aagacgtgct tgagctggtg tctcgggatg     600

agctgaatgt caaatctgag gagcaggtct ttgaagctgc attggcctgg gtcagatacg     660

accgggagca gaggggtccc tacctgcctg agctgctgtc caatatccgc ctgcccctct     720

gtcggcccca gttcctttca gacagagtac agcaggatga cctggtgcgt tgctgccaca     780

aatgcaggga cctggtagac gaagcaaagg actaccacct catgccagag cgccggcccc     840

acctgccagc tttcagaacc cggccacgct gctgcacatc catcgctgga cttatctacg     900

ctgtaggggg cctcaactca gcaggtgatt ccctgaatgt ggtggaagtg ttcgacccca     960

ttgccaattg ctgggagaga tgccgtccca tgacaacagc ccgcagccgc gttggcgtgg    1020

ctgtggtgaa cgggcttctc tatgccatcg gaggatatga cggccagcta cggctgagca    1080

ctgtggaggc ctacaacccg gagacagaca catggaccag agtggggagc atgaatagca    1140

agagaagctc tgtctgtttc agtgccatgg ggacagtcgt gctggatggg cagatctacg    1200

tctgtggggg ctacgatggc aactcttccc tcagctccgt ggagacctac tcacctgaga    1260

cggacaaatg gacagtggtg acctcgatga gctcgaatcg cagtgctgct ggggttacag    1320
```

-continued

```
tctttgaggg caggatatat gtgtcaggcg gccatgatgg tttgcagatc ttcagcagtg   1380
tggaacacta caaccaccac acagccacct ggcaccctgc agctggcatg ctcaacaagc   1440
gctgccggca cggagccgcc tccctgggga gcaagatgtt tgtctgcggg ggctacgatg   1500
gctctggctt cctcagcatt gccgagatgt acagctctgt ggcagaccag tggtgcctga   1560
ttgtccccat gcacacgcgc aggagccggg tctccctggt ggccagctgt gggcgcctct   1620
acgctgttgg gggctacgac ggacagtcaa acctaagctc agtggagatg tatgacccag   1680
agacagactg ctggacattc atggccccca tggcgtgcca tgagggaggg gtcggtgtgg   1740
gctgcatccc tctcctcacc atctaaggca gaggatggga tgtggtgggg cagggatctg   1800
gtacagacat aggcgcttcc ttccaggaac agtccctcag gagaggcagt ggaccagaag   1860
agatggcgaa acgtgagctc gccggaggta cagtttttcc aggtgcttaa gccctccccc   1920
actgtgccac ccttgtgacc ttcaggcttg ggtcatcaag atgcacagca tggaacacaa   1980
gctcctctgg atcctgcagc tggtgacatg gaactgtttt ctggtccaca tgaacacagg   2040
ctccatccag gcccagctcc tacccaccgc ctctctgtgg gccagctgtt cacagaaggc   2100
cttccatctg atgctcccca tcgcctgctt gctctccagc cgagtctggc caatttgcca   2160
tggggaggct gcagtgtcca agcctgctgg aaactgggat gtagctgggg acgaaaggac   2220
agacccaagc gttctccctg cctgagatgg tgtggccaca gcagtggaag gctgcacaca   2280
ggcacattcc ttcttccaca gtggggcacc aaggattctg tcctcattgc tgggtaagca   2340
gggagaagag aagttttccc catgtctaat tttgggattt cagtgaggcc ttttgatctg   2400
tccaggagaa cagaagggaa aaaaagatac ttgaaagaaa ctgaaggaaa tttaaacaaa   2460
gaaacacttg aaagaaactg gaaagaaaaa taattttttt atgtgaacaa attttgcaag   2520
aagaaaaaag cataaaagac actaacggca aatctatgtt taaatggaaa atcgtctaac   2580
tggagaaggg cggtatccac cccacattcg gatcccaggg tcctgaggcc tcgcattgag   2640
ctgggggttc cctctgagcc ccagtgtgtg tggaatcagt gcactcttga ctgggcctgt   2700
agtaaggtgc tcatggggtt tgtcttctca cccaccatca gaggactttt aaaatcatag   2760
gcgtagagag ttaggctatc tgctgaatta ctgccactct tcttggtggg ggctcctagc   2820
tgtggctggg ggctccaggc gcccctgtga ttacctccta ctgccaccat ggcgctcatt   2880
cagattcccc actctcacta acattgcttc ctttttgac cagcaggaaa cagcaggtct   2940
ggccagattc tcacttgccc atcaatctcg ttcttggatg atttccctca ttgtgatgct   3000
tctggggcac gttgaccata tgcacctcta gaacctaacc agggcttcct tctaccagct   3060
gtgggcgggc ttggtctggt aaccttgtct gctctgccat tccactgctc ctccatccac   3120
tcgccaatcc caagagtctg gcctccctcc agccctgggc agactgacca gcaaggtgga   3180
cctttacatt caagcacagc tggcttttat gacataaaga actaaaggcc gaaagaatct   3240
cttgctgctg caaagaacag attttatatt tcttcctcta atcttggcaa atgaccttta   3300
ccttttggaa agatttcata ttgcttcctc ctccctggat aggacctaat gtagcacagc   3360
gggactcaaa gaggaggaca ttttctcttg ccagtgcact gggcagtggg gctgtccttc   3420
aactgctgct gccaaaattg gttttctaaa attcttccag tagagactaa aagaagattc   3480
aattcctgta acccaagact gagtcttagg gctccagtct ccacctgctt ggtttcctat   3540
cctttgctgc ctgcctgggg tggcctggaa gcctgttcag aaaggcacaa tgtggagcct   3600
ggggtgtctc ccccacccca ggaccgtcag gtttaccagt gtgtgcaatc gccatgtatt   3660
```

```
cagagggaag tacctttgtt acctacaact taggagctag gcctctgcta caagcacttg   3720
aaaatgatat ttttattttt aacgtctcaa caatctgata tcggatgtcg tttaacctgg   3780
gctcgtggta gggctccagc atttctccct ccttcctggt ttgcctgtag ggtagactc    3840
ggaaggtggg tggggtgtgc atttcctgtt aggagtgtat cagtgcttgt cttattataa   3900
gccccttcct tttgtgaatt tgaagtagca ccaacaagcc tggattgtga aggtattaag   3960
aatcggtctg tgggctactg agtgggtcct taggatactg gcccagattt tgccactggg   4020
tatggcagat cattttctac catggcctgc tgctcttgta gtggacttcc tgagtccaat   4080
cccacctcct ggtgtagaat ttacactgct gcacctgagg tcgatgtttc aaagtaagat   4140
caagccagtg ttttgatctg ggctctgagc acaagtcagg aaacaccaac atattcacac   4200
tctcccagta ggttcctcag tccgatggtg aatggctatt cgtaaatggc tggtctggct   4260
ctttggtgtt ggagcctttc caatagcccc atgaaaagaa gcatcaccca aggatattgt   4320
aaaaaggatg taacaaggag atagggtaga cattgtactc agtgggcctt ggggcctagc   4380
ccagctctga gcagaggact gtggcattca ctgtccttga gtgtttcacc ttcttggata   4440
acacacgggc cttctcttct ggatttcatc agagattaca gccagatggg ggctgaagac   4500
catcctcttg accacagagg tgtgactgtg ggaattcctc ccaatttatg gtttcccaga   4560
aaatcttagt tccttttatt tatagaatgc atgtcttttg tgttaagaaa ccaaagagaa   4620
ataaagagaa cactcctaat a                                             4641
```

<210> SEQ ID NO 17
<211> LENGTH: 1740
<212> TYPE: DNA
<213> ORGANISM: Homo sapiens

<400> SEQUENCE: 17

```
atggtggagg acggcgcgga ggagctggag gatctggtgc acttctccgt gtctgagttg     60
cctagtcgcg gctacggcgt catggaggag atccggcggc agggcaagct gtgcgacgtg    120
accctcaaga ttggggacca caaattcagt gcccaccgga ttgtcttagc agcctcgatc    180
ccgtatttcc atgctatgtt tacaaatgac atgatggagt gcaagcagga tgagattgta    240
atgcaaggaa tggacccaag tgccctggag gctctgatca actttgccta caacggcaac    300
cttgccattg accagcaaaa tgtccagtca ttgctgatgg gggcgagctt cctgcagctg    360
cagagcatca aagacgcctg ctgcacattc cttcgagaac ggcttcaccc aaaaaactgc    420
ctgggtgtgc gccagtttgc tgagacaatg atgtgtgctg tgctgtacga cgctgccaac    480
agcttcatcc accagcactt tgtggaggtg tccatgtcag aagagttcct ggccctgccc    540
ttggaagacg tgcttgagct ggtgtctcgg gatgagctga atgtcaaatc tgaggagcag    600
gtctttgaag ctgcattggc ctgggtcaga tacgaccggg agcagagggg tccctacctg    660
cctgagctgc tgtccaatat ccgcctgccc ctctgtcggc cccagttcct ttcagacaga    720
gtacagcagg atgacctggt gcgttgctgc cacaaatgca gggacctggt agacgaagca    780
aaggactacc acctcatgcc agagcgccgg ccccacctgc cagctttcag aacccggcca    840
cgctgctgca catccatcgc tggacttatc tacgctgtag ggggcctcaa ctcagcaggt    900
gattccctga atgtggtgga agtgttcgac cccattgcca attgctggga gagatgccgt    960
cccatgacaa cagcccgcag ccgcgttggc gtggctgtgg tgaacgggct tctctatgcc   1020
atcggaggat atgacggcca gctacggctg agcactgtgg aggcctacaa cccggagaca   1080
gacacatgga ccagagtggg gagcatgaat agcaagagaa gctctgtctg tttcagtgcc   1140
```

```
atggggacag tcgtgctgga tgggcagatc tacgtctgtg ggggctacga tggcaactct   1200

tccctcagct ccgtggagac ctactcacct gagacggaca aatggacagt ggtgacctcg   1260

atgagctcga atcgcagtgc tgctggggtt acagtctttg agggcaggat atatgtgtca   1320

ggcggccatg atggtttgca gatcttcagc agtgtggaac actacaacca ccacacagcc   1380

acctggcacc ctgcagctgg catgctcaac aagcgctgcc ggcacggagc cgcctccctg   1440

gggagcaaga tgtttgtctg cgggggctac gatggctctg gcttcctcag cattgccgag   1500

atgtacagct ctgtggcaga ccagtggtgc ctgattgtcc ccatgcacac gcgcaggagc   1560

cgggtctccc tggtggccag ctgtgggcgc ctctacgctg ttgggggcta cgacggacag   1620

tcaaacctaa gctcagtgga gatgtatgac ccagagacag actgctggac attcatggcc   1680

cccatggcgt gccatgaggg aggggtcggt gtgggctgca tccctctcct caccatctaa   1740
```

```
<210> SEQ ID NO 18
<211> LENGTH: 579
<212> TYPE: PRT
<213> ORGANISM: Homo sapiens

<400> SEQUENCE: 18

Met Val Glu Asp Gly Ala Glu Glu Leu Glu Asp Leu Val His Phe Ser
1               5                   10                  15

Val Ser Glu Leu Pro Ser Arg Gly Tyr Gly Val Met Glu Glu Ile Arg
            20                  25                  30

Arg Gln Gly Lys Leu Cys Asp Val Thr Leu Lys Ile Gly Asp His Lys
        35                  40                  45

Phe Ser Ala His Arg Ile Val Leu Ala Ala Ser Ile Pro Tyr Phe His
    50                  55                  60

Ala Met Phe Thr Asn Asp Met Met Glu Cys Lys Gln Asp Glu Ile Val
65                  70                  75                  80

Met Gln Gly Met Asp Pro Ser Ala Leu Glu Ala Leu Ile Asn Phe Ala
                85                  90                  95

Tyr Asn Gly Asn Leu Ala Ile Asp Gln Gln Asn Val Gln Ser Leu Leu
            100                 105                 110

Met Gly Ala Ser Phe Leu Gln Leu Gln Ser Ile Lys Asp Ala Cys Cys
        115                 120                 125

Thr Phe Leu Arg Glu Arg Leu His Pro Lys Asn Cys Leu Gly Val Arg
    130                 135                 140

Gln Phe Ala Glu Thr Met Met Cys Ala Val Leu Tyr Asp Ala Ala Asn
145                 150                 155                 160

Ser Phe Ile His Gln His Phe Val Glu Val Ser Met Ser Glu Glu Phe
                165                 170                 175

Leu Ala Leu Pro Leu Glu Asp Val Leu Glu Leu Val Ser Arg Asp Glu
            180                 185                 190

Leu Asn Val Lys Ser Glu Glu Gln Val Phe Glu Ala Ala Leu Ala Trp
        195                 200                 205

Val Arg Tyr Asp Arg Glu Gln Arg Gly Pro Tyr Leu Pro Glu Leu Leu
    210                 215                 220

Ser Asn Ile Arg Leu Pro Leu Cys Arg Pro Gln Phe Leu Ser Asp Arg
225                 230                 235                 240

Val Gln Gln Asp Asp Leu Val Arg Cys Cys His Lys Cys Arg Asp Leu
                245                 250                 255

Val Asp Glu Ala Lys Asp Tyr His Leu Met Pro Glu Arg Arg Pro His
            260                 265                 270
```

```
Leu Pro Ala Phe Arg Thr Arg Pro Arg Cys Cys Thr Ser Ile Ala Gly
        275                 280                 285

Leu Ile Tyr Ala Val Gly Gly Leu Asn Ser Ala Gly Asp Ser Leu Asn
    290                 295                 300

Val Val Glu Val Phe Asp Pro Ile Ala Asn Cys Trp Glu Arg Cys Arg
305                 310                 315                 320

Pro Met Thr Thr Ala Arg Ser Arg Val Gly Val Ala Val Val Asn Gly
                325                 330                 335

Leu Leu Tyr Ala Ile Gly Gly Tyr Asp Gly Gln Leu Arg Leu Ser Thr
            340                 345                 350

Val Glu Ala Tyr Asn Pro Glu Thr Asp Thr Trp Thr Arg Val Gly Ser
        355                 360                 365

Met Asn Ser Lys Arg Ser Ser Val Cys Phe Ser Ala Met Gly Thr Val
    370                 375                 380

Val Leu Asp Gly Gln Ile Tyr Val Cys Gly Gly Tyr Asp Gly Asn Ser
385                 390                 395                 400

Ser Leu Ser Ser Val Glu Thr Tyr Ser Pro Glu Thr Asp Lys Trp Thr
                405                 410                 415

Val Val Thr Ser Met Ser Ser Asn Arg Ser Ala Ala Gly Val Thr Val
            420                 425                 430

Phe Glu Gly Arg Ile Tyr Val Ser Gly Gly His Asp Gly Leu Gln Ile
        435                 440                 445

Phe Ser Ser Val Glu His Tyr Asn His His Thr Ala Thr Trp His Pro
    450                 455                 460

Ala Ala Gly Met Leu Asn Lys Arg Cys Arg His Gly Ala Ala Ser Leu
465                 470                 475                 480

Gly Ser Lys Met Phe Val Cys Gly Gly Tyr Asp Gly Ser Gly Phe Leu
                485                 490                 495

Ser Ile Ala Glu Met Tyr Ser Ser Val Ala Asp Gln Trp Cys Leu Ile
            500                 505                 510

Val Pro Met His Thr Arg Arg Ser Arg Val Ser Leu Val Ala Ser Cys
        515                 520                 525

Gly Arg Leu Tyr Ala Val Gly Gly Tyr Asp Gly Gln Ser Asn Leu Ser
    530                 535                 540

Ser Val Glu Met Tyr Asp Pro Glu Thr Asp Cys Trp Thr Phe Met Ala
545                 550                 555                 560

Pro Met Ala Cys His Glu Gly Gly Val Gly Val Gly Cys Ile Pro Leu
                565                 570                 575

Leu Thr Ile


<210> SEQ ID NO 19
<211> LENGTH: 4609
<212> TYPE: DNA
<213> ORGANISM: Homo sapiens

<400> SEQUENCE: 19

ctgcgcagtt gcagcggccg gggaagatgg tggaggacgg cgcggaggag ctggaggatc     60

tggtgcactt ctccgtgtct gagttgccta gtcgcggcta cggcgtcatg gaggagatcc    120

ggcggcaggg caagctgtgc gacgtgaccc tcaagattgg ggaccacaaa ttcagtgccc    180

accggattgt cttagcagcc tcgatcccgt atttccatgc tatgtttaca aatgacatga    240

tggagtgcaa gcaggatgag attgtaatgc aaggaatgga cccaagtgcc ctggaggctc    300

tgatcaactt tgcctacaac ggcaaccttg ccattgacca gcaaaatgtc cagtcattgc    360
```

```
tgatgggggc gagcttcctg cagctgcaga gcatcaaaga cgcctgctgc acattccttc    420
gagaacggct tcacccaaaa aactgcctgg gtgtgcgcca gtttgctgag acaatgatgt    480
gtgctgtgct gtacgacgct gccaacagct tcatccacca gcactttgtg gaggtgtcca    540
tgtcagaaga gttcctggcc ctgcccttgg aagacgtgct tgagctggtg tctcgggatg    600
agctgaatgt caaatctgag gagcaggtct ttgaagctgc attggcctgg gtcagatacg    660
accgggagca gaggggtccc tacctgcctg agctgctgtc caatatccgc ctgcccctct    720
gtcggcccca gttcctttca gacagagtac agcaggatga cctggtgcgt tgctgccaca    780
aatgcaggga cctggtagac gaagcaaagg actaccacct catgccagag cgccggcccc    840
acctgccagc tttcagaacc cggccacgct gctgcacatc catcgctgga cttatctacg    900
ctgtaggggg cctcaactca gcagcaaatt tttatgcagg tgattccctg aatgtggtgg    960
aagtgttcga ccccattgcc aattgctggg agagatgccg tcccatgaca acagcccgca   1020
gccgcgttgg cgtggctgtg gtgaacgggc ttctctatgc catcggagga tatgacggcc   1080
agctacggct gagcactgtg gaggcctaca acccggagac agacacatgg accagagtgg   1140
ggagcatgaa tagcaagaga agtgccatgg ggacagtcgt gctggatggg cagatctacg   1200
tctgtggggg ctacgatggc aactcttccc tcagctccgt ggagacctac tcacctgaga   1260
cggacaaatg gacagtggtg acctcgatga gctcgaatcg cagtgctgct ggggttacag   1320
tctttgaggg caggatatat gtgtcaggcg gccatgatgg tttgcagatc ttcagcagtg   1380
tggaacacta caaccaccac acagccacct ggcaccctgc agctggcatg ctcaacaagc   1440
gctgccggca cggagccgcc tccctgggga gcaagatgtt tgtctgcggg ggctacgatg   1500
gctctggctt cctcagcatt gccgagatgt acagctctgt ggcagaccag tggtgcctga   1560
ttgtccccat gcacacgcgc aggagccggg tctccctggt ggccagctgt gggcgcctct   1620
acgctgttgg gggctacgac ggacagtcaa acctaagctc agtggagatg tatgacccag   1680
agacagactg ctggacattc atggccccca tggcgtgcca tgagggaggg gtcggtgtgg   1740
gctgcatccc tctcctcacc atctaaggca gaggatggga tgtggtgggg cagggatctg   1800
gtacagacat aggcgcttcc ttccaggaac agtccctcag gagaggcagt ggaccagaag   1860
agatggcgaa acgtgagctc gccggaggta cagtttttcc aggtgcttaa gccctccccc   1920
actgtgccac ccttgtgacc ttcaggcttg ggtcatcaag atgcacagca tggaacacaa   1980
gctcctctgg atcctgcagc tggtgacatg gaactgtttt ctggtccaca tgaacacagg   2040
ctccatccag gcccagctcc tacccaccgc ctctctgtgg gccagctgtt cacagaaggc   2100
cttccatctg atgctcccca tcgcctgctt gctctccagc cgagtctggc caatttgcca   2160
tggggaggct gcagtgtcca agcctgctgg aaactgggat gtagctgggg acgaaaggac   2220
agacccaagc gttctccctg cctgagatgg tgtggccaca gcagtggaag gctgcacaca   2280
ggcacattcc ttcttccaca gtggggcacc aaggattctg tcctcattgc tgggtaagca   2340
gggagaagag aagttttccc catgtctaat tttgggattt cagtgaggcc ttttgatctg   2400
tccaggagaa cagaagggaa aaaaagatac ttgaaagaaa ctgaaggaaa tttaaacaaa   2460
gaaacacttg aaagaaactg gaaagaaaaa taattttttt atgtgaacaa attttgcaag   2520
aagaaaaaag cataaaagac actaacggca aatctatgtt taaatggaaa atcgtctaac   2580
tggagaaggg cggtatccac cccacattcg gatcccaggg tcctgaggcc tcgcattgag   2640
ctgggggttc cctctgagcc ccagtgtgtg tggaatcagt gcactcttga ctgggcctgt   2700
```

```
agtaaggtgc tcatggggtt tgtcttctca cccaccatca gaggactttt aaaatcatag   2760
gcgtagagag ttaggctatc tgctgaatta ctgccactct tcttggtggg ggctcctagc   2820
tgtggctggg ggctccaggc gcccctgtga ttacctccta ctgccaccat ggcgctcatt   2880
cagattcccc actctcacta acattgcttc ctttttgac cagcaggaaa cagcaggtct   2940
ggccagattc tcacttgccc atcaatctcg ttcttggatg atttccctca ttgtgatgct   3000
tctggggcac gttgaccata tgcacctcta gaacctaacc agggcttcct tctaccagct   3060
gtgggcgggc ttggtctggt aaccttgtct gctctgccat tccactgctc ctccatccac   3120
tcgccaatcc caagagtctg gcctccctcc agccctgggc agactgacca gcaaggtgga   3180
cctttacatt caagcacagc tggcttttat gacataaaga actaaaggcc gaaagaatct   3240
cttgctgctg caaagaacag attttatatt tcttcctcta atcttggcaa atgaccttta   3300
ccttttggaa agatttcata ttgcttcctc ctccctggat aggacctaat gtagcacagc   3360
gggactcaaa gaggaggaca ttttctcttg ccagtgcact gggcagtggg gctgtccttc   3420
aactgctgct gccaaaattg gttttctaaa attcttccag tagagactaa aagaagattc   3480
aattcctgta acccaagact gagtcttagg gctccagtct ccacctgctt ggtttcctat   3540
cctttgctgc ctgcctgggg tggcctggaa gcctgttcag aaaggcacaa tgtggagcct   3600
ggggtgtctc ccccacccca ggaccgtcag gtttaccagt gtgtgcaatc gccatgtatt   3660
cagagggaag tacctttgtt acctacaact taggagctag gcctctgcta caagcacttg   3720
aaaatgatat ttttattttt aacgtctcaa caatctgata tcggatgtcg tttaacctgg   3780
gctcgtggta gggctccagc atttctccct ccttcctggt ttgcctgtag gggtagactc   3840
ggaaggtggg tggggtgtgc atttcctgtt aggagtgtat cagtgcttgt cttattataa   3900
gccccttct tttgtgaatt tgaagtagca ccaacaagcc tggattgtga aggtattaag   3960
aatcggtctg tgggctactg agtgggtcct taggatactg gcccagattt tgccactggg   4020
tatggcagat cattttctac catggcctgc tgctcttgta gtggacttcc tgagtccaat   4080
cccacctcct ggtgtagaat ttacactgct gcacctgagg tcgatgtttc aaagtaagat   4140
caagccagtg ttttgatctg ggctctgagc acaagtcagg aaacaccaac atattcacac   4200
tctcccagta ggttcctcag tccgatggtg aatggctatt cgtaaatggc tggtctggct   4260
ctttggtgtt ggagcctttc caatagcccc atgaaaagaa gcatcaccca aggatattgt   4320
aaaaaggatg taacaaggag atagggtaga cattgtactc agtgggcctt ggggcctagc   4380
ccagctctga gcagaggact gtggcattca ctgtccttga gtgtttcacc ttcttggata   4440
acacacgggc cttctcttct ggatttcatc agagattaca gccagatggg ggctgaagac   4500
catcctcttg accacagagg tgtgactgtg ggaattcctc ccaatttatg gtttcccaga   4560
aaatcttagt tccttttatt tatagaatgc atgtcttttg tgttaagaa              4609
```

<210> SEQ ID NO 20
<211> LENGTH: 1740
<212> TYPE: DNA
<213> ORGANISM: Homo sapiens

<400> SEQUENCE: 20

```
atggtggagg acggcgcgga ggagctggag gatctggtgc acttctccgt gtctgagttg     60
cctagtcgcg gctacggcgt catggaggag atccggcggc agggcaagct gtgcgacgtg    120
accctcaaga ttggggacca caaattcagt gcccaccgga ttgtcttagc agcctcgatc    180
ccgtatttcc atgctatgtt tacaaatgac atgatggagt gcaagcagga tgagattgta    240
```

```
atgcaaggaa tggacccaag tgccctggag gctctgatca actttgccta caacggcaac    300

cttgccattg accagcaaaa tgtccagtca ttgctgatgg gggcgagctt cctgcagctg    360

cagagcatca aagacgcctg ctgcacattc cttcgagaac ggcttcaccc aaaaaactgc    420

ctgggtgtgc gccagtttgc tgagacaatg atgtgtgctg tgctgtacga cgctgccaac    480

agcttcatcc accagcactt tgtggaggtg tccatgtcag aagagttcct ggccctgccc    540

ttggaagacg tgcttgagct ggtgtctcgg gatgagctga atgtcaaatc tgaggagcag    600

gtctttgaag ctgcattggc ctgggtcaga tacgaccggg agcagagggg tccctacctg    660

cctgagctgc tgtccaatat ccgcctgccc ctctgtcggc cccagttcct ttcagacaga    720

gtacagcagg atgacctggt gcgttgctgc cacaaatgca gggacctggt agacgaagca    780

aaggactacc acctcatgcc agagcgccgg ccccacctgc cagctttcag aacccggcca    840

cgctgctgca catccatcgc tggacttatc tacgctgtag ggggcctcaa ctcagcagca    900

aatttttatg caggtgattc cctgaatgtg gtggaagtgt tcgaccccat tgccaattgc    960

tgggagagat gccgtcccat gacaacagcc cgcagccgcg ttggcgtggc tgtggtgaac   1020

gggcttctct atgccatcgg aggatatgac ggccagctac ggctgagcac tgtggaggcc   1080

tacaacccgg agacagacac atggaccaga gtggggagca tgaatagcaa gagaagtgcc   1140

atggggacag tcgtgctgga tgggcagatc tacgtctgtg gggctacga tggcaactct   1200

tccctcagct ccgtggagac ctactcacct gagacggaca aatggacagt ggtgacctcg   1260

atgagctcga atcgcagtgc tgctggggtt acagtctttg agggcaggat atatgtgtca   1320

ggcggccatg atggtttgca gatcttcagc agtgtggaac actacaacca ccacacagcc   1380

acctggcacc ctgcagctgg catgctcaac aagcgctgcc ggcacggagc cgcctccctg   1440

gggagcaaga tgtttgtctg cgggggctac gatggctctg gcttcctcag cattgccgag   1500

atgtacagct ctgtggcaga ccagtggtgc ctgattgtcc ccatgcacac gcgcaggagc   1560

cgggtctccc tggtggccag ctgtgggcgc ctctacgctg ttgggggcta cgacggacag   1620

tcaaacctaa gctcagtgga gatgtatgac ccagagacag actgctggac attcatggcc   1680

cccatggcgt gccatgaggg aggggtcggt gtgggctgca tccctctcct caccatctaa   1740
```

<210> SEQ ID NO 21
<211> LENGTH: 579
<212> TYPE: PRT
<213> ORGANISM: Homo sapiens

<400> SEQUENCE: 21

```
Met Val Glu Asp Gly Ala Glu Glu Leu Glu Asp Leu Val His Phe Ser
1               5                   10                  15

Val Ser Glu Leu Pro Ser Arg Gly Tyr Gly Val Met Glu Glu Ile Arg
            20                  25                  30

Arg Gln Gly Lys Leu Cys Asp Val Thr Leu Lys Ile Gly Asp His Lys
        35                  40                  45

Phe Ser Ala His Arg Ile Val Leu Ala Ala Ser Ile Pro Tyr Phe His
    50                  55                  60

Ala Met Phe Thr Asn Asp Met Met Glu Cys Lys Gln Asp Glu Ile Val
65                  70                  75                  80

Met Gln Gly Met Asp Pro Ser Ala Leu Glu Ala Leu Ile Asn Phe Ala
                85                  90                  95

Tyr Asn Gly Asn Leu Ala Ile Asp Gln Gln Asn Val Gln Ser Leu Leu
            100                 105                 110
```

```
Met Gly Ala Ser Phe Leu Gln Leu Gln Ser Ile Lys Asp Ala Cys Cys
        115                 120                 125

Thr Phe Leu Arg Glu Arg Leu His Pro Lys Asn Cys Leu Gly Val Arg
    130                 135                 140

Gln Phe Ala Glu Thr Met Met Cys Ala Val Leu Tyr Asp Ala Ala Asn
145                 150                 155                 160

Ser Phe Ile His Gln His Phe Val Glu Val Ser Met Ser Glu Glu Phe
                165                 170                 175

Leu Ala Leu Pro Leu Glu Asp Val Leu Glu Leu Val Ser Arg Asp Glu
            180                 185                 190

Leu Asn Val Lys Ser Glu Glu Gln Val Phe Glu Ala Ala Leu Ala Trp
        195                 200                 205

Val Arg Tyr Asp Arg Glu Gln Arg Gly Pro Tyr Leu Pro Glu Leu Leu
    210                 215                 220

Ser Asn Ile Arg Leu Pro Leu Cys Arg Pro Gln Phe Leu Ser Asp Arg
225                 230                 235                 240

Val Gln Gln Asp Asp Leu Val Arg Cys Cys His Lys Cys Arg Asp Leu
                245                 250                 255

Val Asp Glu Ala Lys Asp Tyr His Leu Met Pro Glu Arg Arg Pro His
            260                 265                 270

Leu Pro Ala Phe Arg Thr Arg Pro Arg Cys Cys Thr Ser Ile Ala Gly
        275                 280                 285

Leu Ile Tyr Ala Val Gly Gly Leu Asn Ser Ala Ala Asn Phe Tyr Ala
    290                 295                 300

Gly Asp Ser Leu Asn Val Val Glu Val Phe Asp Pro Ile Ala Asn Cys
305                 310                 315                 320

Trp Glu Arg Cys Arg Pro Met Thr Thr Ala Arg Ser Arg Val Gly Val
                325                 330                 335

Ala Val Val Asn Gly Leu Leu Tyr Ala Ile Gly Gly Tyr Asp Gly Gln
            340                 345                 350

Leu Arg Leu Ser Thr Val Glu Ala Tyr Asn Pro Glu Thr Asp Thr Trp
        355                 360                 365

Thr Arg Val Gly Ser Met Asn Ser Lys Arg Ser Ala Met Gly Thr Val
    370                 375                 380

Val Leu Asp Gly Gln Ile Tyr Val Cys Gly Gly Tyr Asp Gly Asn Ser
385                 390                 395                 400

Ser Leu Ser Ser Val Glu Thr Tyr Ser Pro Glu Thr Asp Lys Trp Thr
                405                 410                 415

Val Val Thr Ser Met Ser Ser Asn Arg Ser Ala Ala Gly Val Thr Val
            420                 425                 430

Phe Glu Gly Arg Ile Tyr Val Ser Gly Gly His Asp Gly Leu Gln Ile
        435                 440                 445

Phe Ser Ser Val Glu His Tyr Asn His His Thr Ala Thr Trp His Pro
    450                 455                 460

Ala Ala Gly Met Leu Asn Lys Arg Cys Arg His Gly Ala Ala Ser Leu
465                 470                 475                 480

Gly Ser Lys Met Phe Val Cys Gly Gly Tyr Asp Gly Ser Gly Phe Leu
                485                 490                 495

Ser Ile Ala Glu Met Tyr Ser Ser Val Ala Asp Gln Trp Cys Leu Ile
            500                 505                 510

Val Pro Met His Thr Arg Arg Ser Arg Val Ser Leu Val Ala Ser Cys
        515                 520                 525
```

```
Gly Arg Leu Tyr Ala Val Gly Gly Tyr Asp Gly Gln Ser Asn Leu Ser
    530                 535                 540

Ser Val Glu Met Tyr Asp Pro Glu Thr Asp Cys Trp Thr Phe Met Ala
545                 550                 555                 560

Pro Met Ala Cys His Glu Gly Gly Val Gly Val Gly Cys Ile Pro Leu
                565                 570                 575

Leu Thr Ile


<210> SEQ ID NO 22
<211> LENGTH: 4519
<212> TYPE: DNA
<213> ORGANISM: Homo sapiens

<400> SEQUENCE: 22

agttgcagcg gccggggaag atggtggagg acggcgcgga ggagctggag gatctggtgc      60

acttctccgt gtctgagttg cctagtcgcg gctacggcgt catggaggag atccggcggc     120

agggcaagct gtgcgacgtg accctcaagt gccctggagg ctctgatcaa ctttgcctac     180

aacggcaacc ttgccattga ccagcaaaat gtccagtcat tgctgatggg ggcgagcttc     240

ctgcagctgc agagcatcaa agacgcctgc tgcacattcc ttcgagaacg gcttcaccca     300

aaaaactgcc tgggtgtgcg ccagtttgct gagacaatga tgtgtgctgt gctgtacgac     360

gctgccaaca gcttcatcca ccagcacttt gtggaggtgt ccatgtcaga agagttcctg     420

gccctgccct tggaagacgt gcttgagctg gtgtctcggg atgagctgaa tgtcaaatct     480

gaggagcagg tctttgaagc tgcattggcc tgggtcagat acgaccggga gcagaggggt     540

ccctacctgc ctgagctgct gtccaatatc cgcctgcccc tctgtcggcc ccagttcctt     600

tcagacagag tacagcagga tgacctggtg cgttgctgcc acaaatgcag ggacctggta     660

gacgaagcaa aggactacca cctcatgcca gagcgccggc cccacctgcc agctttcaga     720

acccggccac gctgctgcac atccatcgct ggacttatct acgctgtagg gggcctcaac     780

tcagcagcaa atttttatgc aggtgattcc ctgaatgtgg tggaagtgtt cgaccccatt     840

gccaattgct gggagagatg ccgtcccatg acaacagccc gcagccgcgt tggcgtggct     900

gtggtgaacg ggcttctcta tgccatcgga ggatatgacg gccagctacg gctgagcact     960

gtggaggcct acaacccgga gacagacaca tggaccagag tggggagcat gaatagcaag    1020

agaagctctg tctgtttcag tgccatgggg acagtcgtgc tggatgggca gatctacgtc    1080

tgtgggggct acgatggcaa ctcttccctc agctccgtgg agacctactc acctgagacg    1140

gacaaatgga cagtggtgac ctcgatgagc tcgaatcgca gtgctgctgg ggttacagtc    1200

tttgagggca ggatatatgt gtcaggcggc catgatggtt tgcagatctt cagcagtgtg    1260

gaacactaca accaccacac agccacctgg caccctgcag ctggcatgct caacaagcgc    1320

tgccggcacg gagccgcctc cctggggagc aagatgtttg tctgcggggg ctacgatggc    1380

tctggcttcc tcagcattgc cgagatgtac agctctgtgg cagaccagtg gtgcctgatt    1440

gtccccatgc acacgcgcag gagccgggtc tccctggtgg ccagctgtgg gcgcctctac    1500

gctgttgggg gctacgacgg acagtcaaac ctaagctcag tggagatgta tgacccagag    1560

acagactgct ggacattcat ggcccccatg gcgtgccatg agggaggggt cggtgtgggc    1620

tgcatccctc tcctcaccat ctaaggcaga ggatgggatg tggtggggca gggatctggt    1680

acagacatag gcgcttcctt ccaggaacag tccctcagga gaggcagtgg accagaagag    1740

atggcgaaac gtgagctcgc cggaggtaca gtttttccag gtgcttaagc cctcccccac    1800
```

```
tgtgccaccc ttgtgacctt caggcttggg tcatcaagat gcacagcatg gaacacaagc   1860
tcctctggat cctgcagctg gtgacatgga actgttttct ggtccacatg aacacaggct   1920
ccatccaggc ccagctccta cccaccgcct ctctgtgggc cagctgttca cagaaggcct   1980
tccatctgat gctccccatc gcctgcttgc tctccagccg agtctggcca atttgccatg   2040
gggaggctgc agtgtccaag cctgctggaa actgggatgt agctggggac gaaaggacag   2100
acccaagcgt tctccctgcc tgagatggtg tggccacagc agtggaaggc tgcacacagg   2160
cacattcctt cttccacagt ggggcaccaa ggattctgtc ctcattgctg ggtaagcagg   2220
gagaagagaa gttttcccca tgtctaattt tgggatttca gtgaggcctt ttgatctgtc   2280
caggagaaca gaagggaaaa aaagatactt gaaagaaact gaaggaaatt taaacaaaga   2340
aacacttgaa agaaactgga aagaaaaata attttttat gtgaacaaat tttgcaagaa   2400
gaaaaaagca taaaagacac taacggcaaa tctatgttta aatggaaaat cgtctaactg   2460
gagaagggcg gtatccaccc cacattcgga tcccagggtc ctgaggcctc gcattgagct   2520
gggggttccc tctgagcccc agtgtgtgtg gaatcagtgc actcttgact gggcctgtag   2580
taaggtgctc atggggtttg tcttctcacc caccatcaga ggacttttaa aatcataggc   2640
gtagagagtt aggctatctg ctgaattact gccactcttc ttggtggggg ctcctagctg   2700
tggctggggg ctccaggcgc ccctgtgatt acctcctact gccaccatgg cgctcattca   2760
gattccccac tctcactaac attgcttcct tttttgacca gcaggaaaca gcaggtctgg   2820
ccagattctc acttgcccat caatctcgtt cttggatgat ttccctcatt gtgatgcttc   2880
tggggcacgt tgaccatatg cacctctaga acctaaccag ggcttccttc taccagctgt   2940
gggcgggctt ggtctggtaa ccttgtctgc tctgccattc cactgctcct ccatccactc   3000
gccaatccca agagtctggc ctccctccag ccctgggcag actgaccagc aaggtggacc   3060
tttacattca agcacagctg gcttttatga cataaagaac taaaggccga aagaatctct   3120
tgctgctgca aagaacagat tttatatttc ttcctctaat cttggcaaat gacctttacc   3180
ttttggaaag atttcatatt gcttcctcct ccctggatag gacctaatgt agcacagcgg   3240
gactcaaaga ggaggacatt ttctcttgcc agtgcactgg gcagtggggc tgtccttcaa   3300
ctgctgctgc caaaattggt tttctaaaat tcttccagta gagactaaaa gaagattcaa   3360
ttcctgtaac ccaagactga gtcttagggc tccagtctcc acctgcttgg tttcctatcc   3420
tttgctgcct gcctggggtg gcctggaagc ctgttcagaa aggcacaatg tggagcctgg   3480
ggtgtctccc ccaccccagg accgtcaggt ttaccagtgt gtgcaatcgc catgtattca   3540
gagggaagta cctttgttac ctacaactta ggagctaggc ctctgctaca agcacttgaa   3600
aatgatattt ttatttttaa cgtctcaaca atctgatatc ggatgtcgtt taacctgggc   3660
tcgtggtagg gctccagcat ttctccctcc ttcctggttt gcctgtaggg gtagactcgg   3720
aaggtgggtg gggtgtgcat ttcctgttag gagtgtatca gtgcttgtct tattataagc   3780
ccctttcttt tgtgaatttg aagtagcacc aacaagcctg gattgtgaag gtattaagaa   3840
tcggtctgtg ggctactgag tgggtcctta ggatactggc ccagattttg ccactgggta   3900
tggcagatca ttttctacca tggcctgctg ctcttgtagt ggacttcctg agtccaatcc   3960
cacctcctgg tgtagaattt acactgctgc acctgaggtc gatgtttcaa agtaagatca   4020
agccagtgtt ttgatctggg ctctgagcac aagtcaggaa acaccaacat attcacactc   4080
tcccagtagg ttcctcagtc cgatggtgaa tggctattcg taaatggctg gtctggctct   4140
ttggtgttgg agcctttcca atagccccat gaaaagaagc atcacccaag gatattgtaa   4200
```

```
aaaggatgta acaaggagat agggtagaca ttgtactcag tgggccttgg ggcctagccc   4260

agctctgagc agaggactgt ggcattcact gtccttgagt gtttcacctt cttggataac   4320

acacgggcct tctcttctgg atttcatcag agattacagc cagatggggg ctgaagacca   4380

tcctcttgac cacagaggtg tgactgtggg aattcctccc aatttatggt ttcccagaaa   4440

atcttagttc cttttattta tagaatgcat gtcttttgtg ttaagaaacc aaagagaaat   4500

aaagagaaca ctcctaata                                                 4519
```

<210> SEQ ID NO 23
<211> LENGTH: 1419
<212> TYPE: DNA
<213> ORGANISM: Homo sapiens

<400> SEQUENCE: 23

```
atgggggcga gcttcctgca gctgcagagc atcaaagacg cctgctgcac attccttcga     60

gaacggcttc acccaaaaaa ctgcctgggt gtgcgccagt ttgctgagac aatgatgtgt    120

gctgtgctgt acgacgctgc caacagcttc atccaccagc actttgtgga ggtgtccatg    180

tcagaagagt tcctggccct gcccttggaa gacgtgcttg agctggtgtc tcgggatgag    240

ctgaatgtca aatctgagga gcaggtcttt gaagctgcat tggcctgggt cagatacgac    300

cgggagcaga ggggtcccta cctgcctgag ctgctgtcca atatccgcct gcccctctgt    360

cggccccagt tcctttcaga cagagtacag caggatgacc tggtgcgttg ctgccacaaa    420

tgcagggacc tggtagacga agcaaaggac taccacctca tgccagagcg ccggccccac    480

ctgccagctt tcagaacccg gccacgctgc tgcacatcca tcgctggact tatctacgct    540

gtagggggcc tcaactcagc agcaaatttt tatgcaggtg attccctgaa tgtggtggaa    600

gtgttcgacc ccattgccaa ttgctgggag agatgccgtc ccatgacaac agcccgcagc    660

cgcgttggcg tggctgtggt gaacgggctt ctctatgcca tcggaggata tgacggccag    720

ctacggctga gcactgtgga ggcctacaac ccggagacag acacatggac cagagtgggg    780

agcatgaata gcaagagaag ctctgtctgt ttcagtgcca tggggacagt cgtgctggat    840

gggcagatct acgtctgtgg gggctacgat ggcaactctt ccctcagctc cgtggagacc    900

tactcacctg agacggacaa atggacagtg gtgacctcga tgagctcgaa tcgcagtgct    960

gctggggtta cagtctttga gggcaggata tatgtgtcag gcggccatga tggtttgcag   1020

atcttcagca gtgtggaaca ctacaaccac cacacagcca cctggcaccc tgcagctggc   1080

atgctcaaca agcgctgccg gcacggagcc gcctccctgg ggagcaagat gtttgtctgc   1140

gggggctacg atggctctgg cttcctcagc attgccgaga tgtacagctc tgtggcagac   1200

cagtggtgcc tgattgtccc catgcacacg cgcaggagcc gggtctccct ggtggccagc   1260

tgtgggcgcc tctacgctgt tgggggctac gacggacagt caaacctaag ctcagtggag   1320

atgtatgacc cagagacaga ctgctggaca ttcatggccc ccatggcgtg ccatgaggga   1380

ggggtcggtg tgggctgcat ccctctcctc accatctaa                           1419
```

<210> SEQ ID NO 24
<211> LENGTH: 472
<212> TYPE: PRT
<213> ORGANISM: Homo sapiens

<400> SEQUENCE: 24

```
Met Gly Ala Ser Phe Leu Gln Leu Gln Ser Ile Lys Asp Ala Cys Cys
1               5                   10                  15
```

```
Thr Phe Leu Arg Glu Arg Leu His Pro Lys Asn Cys Leu Gly Val Arg
            20                  25                  30

Gln Phe Ala Glu Thr Met Met Cys Ala Val Leu Tyr Asp Ala Ala Asn
        35                  40                  45

Ser Phe Ile His Gln His Phe Val Glu Val Ser Met Ser Glu Glu Phe
    50                  55                  60

Leu Ala Leu Pro Leu Glu Asp Val Leu Glu Leu Val Ser Arg Asp Glu
65                  70                  75                  80

Leu Asn Val Lys Ser Glu Glu Gln Val Phe Glu Ala Ala Leu Ala Trp
                85                  90                  95

Val Arg Tyr Asp Arg Glu Gln Arg Gly Pro Tyr Leu Pro Glu Leu Leu
            100                 105                 110

Ser Asn Ile Arg Leu Pro Leu Cys Arg Pro Gln Phe Leu Ser Asp Arg
        115                 120                 125

Val Gln Gln Asp Asp Leu Val Arg Cys Cys His Lys Cys Arg Asp Leu
    130                 135                 140

Val Asp Glu Ala Lys Asp Tyr His Leu Met Pro Glu Arg Arg Pro His
145                 150                 155                 160

Leu Pro Ala Phe Arg Thr Arg Pro Arg Cys Cys Thr Ser Ile Ala Gly
                165                 170                 175

Leu Ile Tyr Ala Val Gly Gly Leu Asn Ser Ala Ala Asn Phe Tyr Ala
            180                 185                 190

Gly Asp Ser Leu Asn Val Val Glu Val Phe Asp Pro Ile Ala Asn Cys
        195                 200                 205

Trp Glu Arg Cys Arg Pro Met Thr Thr Ala Arg Ser Arg Val Gly Val
    210                 215                 220

Ala Val Val Asn Gly Leu Leu Tyr Ala Ile Gly Gly Tyr Asp Gly Gln
225                 230                 235                 240

Leu Arg Leu Ser Thr Val Glu Ala Tyr Asn Pro Glu Thr Asp Thr Trp
                245                 250                 255

Thr Arg Val Gly Ser Met Asn Ser Lys Arg Ser Ser Val Cys Phe Ser
            260                 265                 270

Ala Met Gly Thr Val Val Leu Asp Gly Gln Ile Tyr Val Cys Gly Gly
        275                 280                 285

Tyr Asp Gly Asn Ser Ser Leu Ser Ser Val Glu Thr Tyr Ser Pro Glu
    290                 295                 300

Thr Asp Lys Trp Thr Val Val Thr Ser Met Ser Ser Asn Arg Ser Ala
305                 310                 315                 320

Ala Gly Val Thr Val Phe Glu Gly Arg Ile Tyr Val Ser Gly Gly His
                325                 330                 335

Asp Gly Leu Gln Ile Phe Ser Ser Val Glu His Tyr Asn His His Thr
            340                 345                 350

Ala Thr Trp His Pro Ala Ala Gly Met Leu Asn Lys Arg Cys Arg His
        355                 360                 365

Gly Ala Ala Ser Leu Gly Ser Lys Met Phe Val Cys Gly Gly Tyr Asp
    370                 375                 380

Gly Ser Gly Phe Leu Ser Ile Ala Glu Met Tyr Ser Ser Val Ala Asp
385                 390                 395                 400

Gln Trp Cys Leu Ile Val Pro Met His Thr Arg Arg Ser Arg Val Ser
                405                 410                 415

Leu Val Ala Ser Cys Gly Arg Leu Tyr Ala Val Gly Gly Tyr Asp Gly
            420                 425                 430
```

```
Gln Ser Asn Leu Ser Ser Val Glu Met Tyr Asp Pro Glu Thr Asp Cys
        435                 440                 445

Trp Thr Phe Met Ala Pro Met Ala Cys His Glu Gly Gly Val Gly Val
    450                 455                 460

Gly Cys Ile Pro Leu Leu Thr Ile
465                 470


<210> SEQ ID NO 25
<211> LENGTH: 4504
<212> TYPE: DNA
<213> ORGANISM: Homo sapiens

<400> SEQUENCE: 25

agttgcagcg gccggggaag atggtggagg acggcgcgga ggagctggag gatctggtgc      60

acttctccgt gtctgagttg cctagtcgcg gctacggcgt catggaggag atccggcggc     120

agggcaagct gtgcgacgtg accctcaagt gccctggagg ctctgatcaa ctttgcctac     180

aacggcaacc ttgccattga ccagcaaaat gtccagtcat tgctgatggg ggcgagcttc     240

ctgcagctgc agagcatcaa agacgcctgc tgcacattcc ttcgagaacg gcttcaccca     300

aaaaactgcc tgggtgtgcg ccagtttgct gagacaatga tgtgtgctgt gctgtacgac     360

gctgccaaca gcttcatcca ccagcacttt gtggaggtgt ccatgtcaga agagttcctg     420

gccctgccct tggaagacgt gcttgagctg gtgtctcggg atgagctgaa tgtcaaatct     480

gaggagcagg tctttgaagc tgcattggcc tgggtcagat acgaccggga gcagaggggt     540

ccctacctgc ctgagctgct gtccaatatc cgcctgcccc tctgtcggcc ccagttcctt     600

tcagacagag tacagcagga tgacctggtg cgttgctgcc acaaatgcag ggacctggta     660

gacgaagcaa aggactacca cctcatgcca gagcgccggc cccacctgcc agctttcaga     720

acccggccac gctgctgcac atccatcgct ggacttatct acgctgtagg gggcctcaac     780

tcagcagcaa atttttatgc aggtgattcc ctgaatgtgg tggaagtgtt cgaccccatt     840

gccaattgct gggagagatg ccgtcccatg acaacagccc gcagccgcgt tggcgtggct     900

gtggtgaacg ggcttctcta tgccatcgga ggatatgacg gccagctacg gctgagcact     960

gtggaggcct acaacccgga gacagacaca tggaccagag tggggagcat gaatagcaag    1020

agaagtgcca tggggacagt cgtgctggat gggcagatct acgtctgtgg gggctacgat    1080

ggcaactctt ccctcagctc cgtggagacc tactcacctg agacggacaa atggacagtg    1140

gtgacctcga tgagctcgaa tcgcagtgct gctggggtta cagtctttga gggcaggata    1200

tatgtgtcag gcggccatga tggtttgcag atcttcagca gtgtggaaca ctacaaccac    1260

cacacagcca cctggcaccc tgcagctggc atgctcaaca agcgctgccg gcacggagcc    1320

gcctccctgg ggagcaagat gtttgtctgc gggggctacg atggctctgg cttcctcagc    1380

attgccgaga tgtacagctc tgtggcagac cagtggtgcc tgattgtccc catgcacacg    1440

cgcaggagcc gggtctccct ggtggccagc tgtgggcgcc tctacgctgt tgggggctac    1500

gacggacagt caaacctaag ctcagtggag atgtatgacc cagagacaga ctgctggaca    1560

ttcatggccc ccatggcgtg ccatgaggga ggggtcggtg tgggctgcat ccctctcctc    1620

accatctaag gcagaggatg ggatgtggtg gggcagggat ctggtacaga cataggcgct    1680

tccttccagg aacagtccct caggagaggc agtggaccag aagagatggc gaaacgtgag    1740

ctcgccggag gtacagtttt tccaggtgct taagccctcc cccactgtgc cacccttgtg    1800

accttcaggc ttgggtcatc aagatgcaca gcatggaaca caagctcctc tggatcctgc    1860
```

-continued

```
agctggtgac atggaactgt tttctggtcc acatgaacac aggctccatc caggcccagc   1920
tcctacccac cgcctctctg tgggccagct gttcacagaa ggccttccat ctgatgctcc   1980
ccatcgcctg cttgctctcc agccgagtct ggccaatttg ccatggggag gctgcagtgt   2040
ccaagcctgc tggaaactgg gatgtagctg gggacgaaag gacagaccca agcgttctcc   2100
ctgcctgaga tggtgtggcc acagcagtgg aaggctgcac acaggcacat tccttcttcc   2160
acagtggggc accaaggatt ctgtcctcat tgctgggtaa gcagggagaa gagaagtttt   2220
ccccatgtct aattttggga tttcagtgag gccttttgat ctgtccagga gaacagaagg   2280
gaaaaaaaga tacttgaaag aaactgaagg aaatttaaac aaagaaacac ttgaaagaaa   2340
ctggaaagaa aaataatttt tttatgtgaa caaattttgc aagaagaaaa aagcataaaa   2400
gacactaacg gcaaatctat gtttaaatgg aaaatcgtct aactggagaa gggcggtatc   2460
caccccacat tcggatccca gggtcctgag gcctcgcatt gagctggggg ttccctctga   2520
gccccagtgt gtgtggaatc agtgcactct tgactgggcc tgtagtaagg tgctcatggg   2580
gtttgtcttc tcacccacca tcagaggact tttaaaatca taggcgtaga gagttaggct   2640
atctgctgaa ttactgccac tcttcttggt gggggctcct agctgtggct gggggctcca   2700
ggcgcccctg tgattacctc ctactgccac catggcgctc attcagattc cccactctca   2760
ctaacattgc ttcctttttt gaccagcagg aaacagcagg tctggccaga ttctcacttg   2820
cccatcaatc tcgttcttgg atgatttccc tcattgtgat gcttctgggg cacgttgacc   2880
atatgcacct ctagaaccta accagggctt ccttctacca gctgtgggcg ggcttggtct   2940
ggtaaccttg tctgctctgc cattccactg ctcctccatc cactcgccaa tcccaagagt   3000
ctggcctccc tccagccctg ggcagactga ccagcaaggt ggacctttac attcaagcac   3060
agctggcttt tatgacataa agaactaaag gccgaaagaa tctcttgctg ctgcaaagaa   3120
cagattttat atttcttcct ctaatcttgg caaatgacct ttaccttttg gaaagatttc   3180
atattgcttc ctcctccctg gataggacct aatgtagcac agcgggactc aaagaggagg   3240
acatttctc ttgccagtgc actgggcagt ggggctgtcc ttcaactgct gctgccaaaa   3300
ttggttttct aaaattcttc cagtagagac taaaagaaga ttcaattcct gtaacccaag   3360
actgagtctt agggctccag tctccacctg cttggtttcc tatcctttgc tgcctgcctg   3420
gggtggcctg gaagcctgtt cagaaaggca caatgtggag cctggggtgt ctcccccacc   3480
ccaggaccgt caggtttacc agtgtgtgca atcgccatgt attcagaggg aagtaccttt   3540
gttacctaca acttaggagc taggcctctg ctacaagcac ttgaaaatga tatttttatt   3600
tttaacgtct caacaatctg atatcggatg tcgtttaacc tgggctcgtg gtagggctcc   3660
agcatttctc cctccttcct ggtttgcctg taggggtaga ctcggaaggt gggtggggtg   3720
tgcatttcct gttaggagtg tatcagtgct tgtcttatta taagcccctt tcttttgtga   3780
atttgaagta gcaccaacaa gcctggattg tgaaggtatt aagaatcggt ctgtgggcta   3840
ctgagtgggt ccttaggata ctggcccaga ttttgccact gggtatggca gatcattttc   3900
taccatggcc tgctgctctt gtagtggact tcctgagtcc aatcccacct cctggtgtag   3960
aatttacact gctgcacctg aggtcgatgt ttcaaagtaa gatcaagcca gtgttttgat   4020
ctgggctctg agcacaagtc aggaaacacc aacatattca cactctccca gtaggttcct   4080
cagtccgatg gtgaatggct attcgtaaat ggctggtctg gctctttggt gttggagcct   4140
ttccaatagc cccatgaaaa gaagcatcac ccaaggatat tgtaaaaagg atgtaacaag   4200
gagatagggt agacattgta ctcagtgggc cttggggcct agcccagctc tgagcagagg   4260
```

```
actgtggcat tcactgtcct tgagtgtttc accttcttgg ataacacacg ggccttctct   4320

tctggatttc atcagagatt acagccagat gggggctgaa gaccatcctc ttgaccacag   4380

aggtgtgact gtgggaattc ctcccaattt atggtttccc agaaaatctt agttcctttt   4440

atttatagaa tgcatgtctt ttgtgttaag aaaccaaaga gaaataaaga gaacactcct   4500

aata                                                                4504
```

<210> SEQ ID NO 26
<211> LENGTH: 1404
<212> TYPE: DNA
<213> ORGANISM: Homo sapiens

<400> SEQUENCE: 26

```
atgggggcga gcttcctgca gctgcagagc atcaaagacg cctgctgcac attccttcga     60

gaacggcttc acccaaaaaa ctgcctgggt gtgcgccagt ttgctgagac aatgatgtgt    120

gctgtgctgt acgacgctgc caacagcttc atccaccagc actttgtgga ggtgtccatg    180

tcagaagagt tcctggccct gcccttggaa gacgtgcttg agctggtgtc tcgggatgag    240

ctgaatgtca aatctgagga gcaggtcttt gaagctgcat tggcctgggt cagatacgac    300

cgggagcaga ggggtcccta cctgcctgag ctgctgtcca atatccgcct gcccctctgt    360

cggccccagt tcctttcaga cagagtacag caggatgacc tggtgcgttg ctgccacaaa    420

tgcagggacc tggtagacga agcaaaggac taccacctca tgccagagcg ccggccccac    480

ctgccagctt tcagaacccg gccacgctgc tgcacatcca tcgctggact tatctacgct    540

gtagggggcc tcaactcagc agcaaatttt tatgcaggtg attccctgaa tgtggtggaa    600

gtgttcgacc ccattgccaa ttgctgggag agatgccgtc ccatgacaac agcccgcagc    660

cgcgttggcg tggctgtggt gaacgggctt ctctatgcca tcggaggata tgacggccag    720

ctacggctga gcactgtgga ggcctacaac ccggagacag acacatggac cagagtgggg    780

agcatgaata gcaagagaag tgccatgggg acagtcgtgc tggatgggca gatctacgtc    840

tgtgggggct acgatggcaa ctcttccctc agctccgtgg agacctactc acctgagacg    900

gacaaatgga cagtggtgac ctcgatgagc tcgaatcgca gtgctgctgg ggttacagtc    960

tttgagggca ggatatatgt gtcaggcggc catgatggtt tgcagatctt cagcagtgtg   1020

gaacactaca accaccacac agccacctgg caccctgcag ctggcatgct caacaagcgc   1080

tgccggcacg gagccgcctc cctggggagc aagatgtttg tctgcggggg ctacgatggc   1140

tctggcttcc tcagcattgc cgagatgtac agctctgtgg cagaccagtg gtgcctgatt   1200

gtccccatgc acacgcgcag gagccgggtc tccctggtgg ccagctgtgg gcgcctctac   1260

gctgttgggg gctacgacgg acagtcaaac ctaagctcag tggagatgta tgacccagag   1320

acagactgct ggacattcat ggcccccatg gcgtgccatg agggaggggt cggtgtgggc   1380

tgcatccctc tcctcaccat ctaa                                          1404
```

<210> SEQ ID NO 27
<211> LENGTH: 467
<212> TYPE: PRT
<213> ORGANISM: Homo sapiens

<400> SEQUENCE: 27

```
Met Gly Ala Ser Phe Leu Gln Leu Gln Ser Ile Lys Asp Ala Cys Cys
1               5                   10                  15

Thr Phe Leu Arg Glu Arg Leu His Pro Lys Asn Cys Leu Gly Val Arg
```

```
            20                  25                  30

Gln Phe Ala Glu Thr Met Met Cys Ala Val Leu Tyr Asp Ala Ala Asn
        35                  40                  45

Ser Phe Ile His Gln His Phe Val Glu Val Ser Met Ser Glu Glu Phe
    50                  55                  60

Leu Ala Leu Pro Leu Glu Asp Val Leu Glu Leu Val Ser Arg Asp Glu
65                  70                  75                  80

Leu Asn Val Lys Ser Glu Glu Gln Val Phe Glu Ala Ala Leu Ala Trp
                85                  90                  95

Val Arg Tyr Asp Arg Glu Gln Arg Gly Pro Tyr Leu Pro Glu Leu Leu
            100                 105                 110

Ser Asn Ile Arg Leu Pro Leu Cys Arg Pro Gln Phe Leu Ser Asp Arg
        115                 120                 125

Val Gln Gln Asp Asp Leu Val Arg Cys Cys His Lys Cys Arg Asp Leu
    130                 135                 140

Val Asp Glu Ala Lys Asp Tyr His Leu Met Pro Glu Arg Arg Pro His
145                 150                 155                 160

Leu Pro Ala Phe Arg Thr Arg Pro Arg Cys Cys Thr Ser Ile Ala Gly
                165                 170                 175

Leu Ile Tyr Ala Val Gly Gly Leu Asn Ser Ala Ala Asn Phe Tyr Ala
            180                 185                 190

Gly Asp Ser Leu Asn Val Val Glu Val Phe Asp Pro Ile Ala Asn Cys
        195                 200                 205

Trp Glu Arg Cys Arg Pro Met Thr Thr Ala Arg Ser Arg Val Gly Val
    210                 215                 220

Ala Val Val Asn Gly Leu Leu Tyr Ala Ile Gly Gly Tyr Asp Gly Gln
225                 230                 235                 240

Leu Arg Leu Ser Thr Val Glu Ala Tyr Asn Pro Glu Thr Asp Thr Trp
                245                 250                 255

Thr Arg Val Gly Ser Met Asn Ser Lys Arg Ser Ala Met Gly Thr Val
            260                 265                 270

Val Leu Asp Gly Gln Ile Tyr Val Cys Gly Gly Tyr Asp Gly Asn Ser
        275                 280                 285

Ser Leu Ser Ser Val Glu Thr Tyr Ser Pro Glu Thr Asp Lys Trp Thr
    290                 295                 300

Val Val Thr Ser Met Ser Ser Asn Arg Ser Ala Ala Gly Val Thr Val
305                 310                 315                 320

Phe Glu Gly Arg Ile Tyr Val Ser Gly Gly His Asp Gly Leu Gln Ile
                325                 330                 335

Phe Ser Ser Val Glu His Tyr Asn His His Thr Ala Thr Trp His Pro
            340                 345                 350

Ala Ala Gly Met Leu Asn Lys Arg Cys Arg His Gly Ala Ala Ser Leu
        355                 360                 365

Gly Ser Lys Met Phe Val Cys Gly Gly Tyr Asp Gly Ser Gly Phe Leu
    370                 375                 380

Ser Ile Ala Glu Met Tyr Ser Ser Val Ala Asp Gln Trp Cys Leu Ile
385                 390                 395                 400

Val Pro Met His Thr Arg Arg Ser Arg Val Ser Leu Val Ala Ser Cys
                405                 410                 415

Gly Arg Leu Tyr Ala Val Gly Gly Tyr Asp Gly Gln Ser Asn Leu Ser
            420                 425                 430

Ser Val Glu Met Tyr Asp Pro Glu Thr Asp Cys Trp Thr Phe Met Ala
        435                 440                 445
```

```
Pro Met Ala Cys His Glu Gly Gly Val Gly Val Gly Cys Ile Pro Leu
    450                 455                 460

Leu Thr Ile
465


<210> SEQ ID NO 28
<211> LENGTH: 4489
<212> TYPE: DNA
<213> ORGANISM: Homo sapiens

<400> SEQUENCE: 28

agttgcagcg gccggggaag atggtggagg acggcgcgga ggagctggag gatctggtgc      60

acttctccgt gtctgagttg cctagtcgcg gctacggcgt catggaggag atccggcggc     120

agggcaagct gtgcgacgtg accctcaagt gccctggagg ctctgatcaa ctttgcctac     180

aacggcaacc ttgccattga ccagcaaaat gtccagtcat tgctgatggg ggcgagcttc     240

ctgcagctgc agagcatcaa agacgcctgc tgcacattcc ttcgagaacg gcttcaccca     300

aaaaactgcc tgggtgtgcg ccagtttgct gagacaatga tgtgtgctgt gctgtacgac     360

gctgccaaca gcttcatcca ccagcacttt gtggaggtgt ccatgtcaga agagttcctg     420

gccctgccct tggaagacgt gcttgagctg gtgtctcggg atgagctgaa tgtcaaatct     480

gaggagcagg tctttgaagc tgcattggcc tgggtcagat acgaccggga gcagaggggt     540

ccctacctgc ctgagctgct gtccaatatc cgcctgcccc tctgtcggcc ccagttcctt     600

tcagacagag tacagcagga tgacctggtg cgttgctgcc acaaatgcag ggacctggta     660

gacgaagcaa aggactacca cctcatgcca gagcgccggc cccacctgcc agctttcaga     720

acccggccac gctgctgcac atccatcgct ggacttatct acgctgtagg gggcctcaac     780

tcagcaggtg attccctgaa tgtggtggaa gtgttcgacc ccattgccaa ttgctgggag     840

agatgccgtc ccatgacaac agcccgcagc cgcgttggcg tggctgtggt gaacgggctt     900

ctctatgcca tcggaggata tgacggccag ctacggctga gcactgtgga ggcctacaac     960

ccggagacag acacatggac cagagtgggg agcatgaata gcaagagaag tgccatgggg    1020

acagtcgtgc tggatgggca gatctacgtc tgtgggggct acgatggcaa ctcttccctc    1080

agctccgtgg agacctactc acctgagacg gacaaatgga cagtggtgac ctcgatgagc    1140

tcgaatcgca gtgctgctgg ggttacagtc tttgagggca ggatatatgt gtcaggcggc    1200

catgatggtt tgcagatctt cagcagtgtg gaacactaca accaccacac agccacctgg    1260

caccctgcag ctggcatgct caacaagcgc tgccggcacg gagccgcctc cctggggagc    1320

aagatgtttg tctgcggggg ctacgatggc tctggcttcc tcagcattgc cgagatgtac    1380

agctctgtgg cagaccagtg gtgcctgatt gtccccatgc acacgcgcag gagccgggtc    1440

tccctggtgg ccagctgtgg gcgcctctac gctgttgggg gctacgacgg acagtcaaac    1500

ctaagctcag tggagatgta tgacccagag acagactgct ggacattcat ggcccccatg    1560

gcgtgccatg agggaggggt cggtgtgggc tgcatccctc tcctcaccat ctaaggcaga    1620

ggatgggatg tggtggggca gggatctggt acagacatag gcgcttcctt ccaggaacag    1680

tccctcagga gaggcagtgg accagaagag atggcgaaac gtgagctcgc cggaggtaca    1740

gtttttccag gtgcttaagc cctcccccac tgtgccaccc ttgtgacctt caggcttggg    1800

tcatcaagat gcacagcatg gaacacaagc tcctctggat cctgcagctg gtgacatgga    1860

actgttttct ggtccacatg aacacaggct ccatccaggc ccagctccta cccaccgcct    1920
```

```
ctctgtgggc cagctgttca cagaaggcct tccatctgat gctccccatc gcctgcttgc   1980
tctccagccg agtctggcca atttgccatg gggaggctgc agtgtccaag cctgctggaa   2040
actgggatgt agctggggac gaaaggacag acccaagcgt tctccctgcc tgagatggtg   2100
tggccacagc agtggaaggc tgcacacagg cacattcctt cttccacagt ggggcaccaa   2160
ggattctgtc ctcattgctg ggtaagcagg gagaagagaa gttttcccca tgtctaattt   2220
tgggatttca gtgaggcctt ttgatctgtc caggagaaca gaagggaaaa aaagatactt   2280
gaaagaaact gaaggaaatt taaacaaaga aacacttgaa agaaactgga aagaaaaata   2340
attttttat gtgaacaaat tttgcaagaa gaaaaaagca taaaagacac taacggcaaa    2400
tctatgttta aatggaaaat cgtctaactg gagaagggcg gtatccaccc cacattcgga   2460
tcccagggtc ctgaggcctc gcattgagct gggggttccc tctgagcccc agtgtgtgtg   2520
gaatcagtgc actcttgact gggcctgtag taaggtgctc atggggtttg tcttctcacc   2580
caccatcaga ggacttttaa aatcataggc gtagagagtt aggctatctg ctgaattact   2640
gccactcttc ttggtggggg ctcctagctg tggctggggg ctccaggcgc ccctgtgatt   2700
acctcctact gccaccatgg cgctcattca gattccccac tctcactaac attgcttcct   2760
tttttgacca gcaggaaaca gcaggtctgg ccagattctc acttgcccat caatctcgtt   2820
cttggatgat ttccctcatt gtgatgcttc tggggcacgt tgaccatatg cacctctaga   2880
acctaaccag ggcttccttc taccagctgt gggcgggctt ggtctggtaa ccttgtctgc   2940
tctgccattc cactgctcct ccatccactc gccaatccca agagtctggc ctccctccag   3000
ccctgggcag actgaccagc aaggtggacc tttacattca agcacagctg gcttttatga   3060
cataaagaac taaaggccga aagaatctct tgctgctgca aagaacagat tttatatttc   3120
ttcctctaat cttggcaaat gacctttacc ttttggaaag atttcatatt gcttcctcct   3180
ccctggatag gacctaatgt agcacagcgg gactcaaaga ggaggacatt ttctcttgcc   3240
agtgcactgg gcagtggggc tgtccttcaa ctgctgctgc caaaattggt tttctaaaat   3300
tcttccagta gagactaaaa gaagattcaa ttcctgtaac ccaagactga gtcttagggc   3360
tccagtctcc acctgcttgg tttcctatcc tttgctgcct gcctggggtg gcctggaagc   3420
ctgttcagaa aggcacaatg tggagcctgg ggtgtctccc ccaccccagg accgtcaggt   3480
ttaccagtgt gtgcaatcgc catgtattca gagggaagta cctttgttac ctacaactta   3540
ggagctaggc ctctgctaca agcacttgaa aatgatattt ttatttttaa cgtctcaaca   3600
atctgatatc ggatgtcgtt taacctgggc tcgtggtagg gctccagcat ttctccctcc   3660
ttcctggttt gcctgtaggg gtagactcgg aaggtgggtg gggtgtgcat ttcctgttag   3720
gagtgtatca gtgcttgtct tattataagc ccctttcttt tgtgaatttg aagtagcacc   3780
aacaagcctg gattgtgaag gtattaagaa tcggtctgtg ggctactgag tgggtcctta   3840
ggatactggc ccagattttg ccactgggta tggcagatca ttttctacca tggcctgctg   3900
ctcttgtagt ggacttcctg agtccaatcc cacctcctgg tgtagaattt acactgctgc   3960
acctgaggtc gatgtttcaa agtaagatca agccagtgtt ttgatctggg ctctgagcac   4020
aagtcaggaa acaccaacat attcacactc tcccagtagg ttcctcagtc cgatggtgaa   4080
tggctattcg taaatggctg gtctggctct ttggtgttgg agcctttcca atagccccat   4140
gaaaagaagc atcacccaag gatattgtaa aaaggatgta acaaggagat agggtagaca   4200
ttgtactcag tgggccttgg ggcctagccc agctctgagc agaggactgt ggcattcact   4260
gtccttgagt gtttcacctt cttggataac acacgggcct tctcttctgg atttcatcag   4320
```

```
agattacagc cagatggggg ctgaagacca tcctcttgac cacagaggtg tgactgtggg   4380

aattcctccc aatttatggt ttcccagaaa atcttagttc cttttattta tagaatgcat   4440

gtcttttgtg ttaagaaacc aaagagaaat aaagagaaca ctcctaata              4489


<210> SEQ ID NO 29
<211> LENGTH: 1389
<212> TYPE: DNA
<213> ORGANISM: Homo sapiens

<400> SEQUENCE: 29

atgggggcga gcttcctgca gctgcagagc atcaaagacg cctgctgcac attccttcga     60

gaacggcttc acccaaaaaa ctgcctgggt gtgcgccagt ttgctgagac aatgatgtgt    120

gctgtgctgt acgacgctgc caacagcttc atccaccagc actttgtgga ggtgtccatg    180

tcagaagagt tcctggccct gcccttggaa gacgtgcttg agctggtgtc tcgggatgag    240

ctgaatgtca aatctgagga gcaggtcttt gaagctgcat tggcctgggt cagatacgac    300

cgggagcaga ggggtcccta cctgcctgag ctgctgtcca atatccgcct gcccctctgt    360

cggccccagt tcctttcaga cagagtacag caggatgacc tggtgcgttg ctgccacaaa    420

tgcagggacc tggtagacga agcaaaggac taccacctca tgccagagcg ccggccccac    480

ctgccagctt tcagaacccg gccacgctgc tgcacatcca tcgctggact tatctacgct    540

gtagggggcc tcaactcagc aggtgattcc ctgaatgtgg tggaagtgtt cgaccccatt    600

gccaattgct gggagagatg ccgtcccatg acaacagccc gcagccgcgt tggcgtggct    660

gtggtgaacg ggcttctcta tgccatcgga ggatatgacg gccagctacg gctgagcact    720

gtggaggcct acaacccgga gacagacaca tggaccagag tggggagcat gaatagcaag    780

agaagtgcca tggggacagt cgtgctggat gggcagatct acgtctgtgg gggctacgat    840

ggcaactctt ccctcagctc cgtggagacc tactcacctg agacggacaa atggacagtg    900

gtgacctcga tgagctcgaa tcgcagtgct gctggggtta cagtctttga gggcaggata    960

tatgtgtcag gcggccatga tggtttgcag atcttcagca gtgtggaaca ctacaaccac   1020

cacacagcca cctggcaccc tgcagctggc atgctcaaca agcgctgccg gcacggagcc   1080

gcctccctgg ggagcaagat gtttgtctgc gggggctacg atggctctgg cttcctcagc   1140

attgccgaga tgtacagctc tgtggcagac cagtggtgcc tgattgtccc catgcacacg   1200

cgcaggagcc gggtctccct ggtggccagc tgtgggcgcc tctacgctgt tgggggctac   1260

gacggacagt caaacctaag ctcagtggag atgtatgacc cagagacaga ctgctggaca   1320

ttcatggccc ccatggcgtg ccatgaggga ggggtcggtg tgggctgcat ccctctcctc   1380

accatctaa                                                          1389


<210> SEQ ID NO 30
<211> LENGTH: 462
<212> TYPE: PRT
<213> ORGANISM: Homo sapiens

<400> SEQUENCE: 30

Met Gly Ala Ser Phe Leu Gln Leu Gln Ser Ile Lys Asp Ala Cys Cys
1               5                   10                  15

Thr Phe Leu Arg Glu Arg Leu His Pro Lys Asn Cys Leu Gly Val Arg
            20                  25                  30

Gln Phe Ala Glu Thr Met Met Cys Ala Val Leu Tyr Asp Ala Ala Asn
        35                  40                  45
```

```
Ser Phe Ile His Gln His Phe Val Glu Val Ser Met Ser Glu Glu Phe
    50                  55                  60

Leu Ala Leu Pro Leu Glu Asp Val Leu Glu Leu Val Ser Arg Asp Glu
65                  70                  75                  80

Leu Asn Val Lys Ser Glu Glu Gln Val Phe Glu Ala Ala Leu Ala Trp
                85                  90                  95

Val Arg Tyr Asp Arg Glu Gln Arg Gly Pro Tyr Leu Pro Glu Leu Leu
            100                 105                 110

Ser Asn Ile Arg Leu Pro Leu Cys Arg Pro Gln Phe Leu Ser Asp Arg
        115                 120                 125

Val Gln Gln Asp Asp Leu Val Arg Cys Cys His Lys Cys Arg Asp Leu
    130                 135                 140

Val Asp Glu Ala Lys Asp Tyr His Leu Met Pro Glu Arg Arg Pro His
145                 150                 155                 160

Leu Pro Ala Phe Arg Thr Arg Pro Arg Cys Cys Thr Ser Ile Ala Gly
                165                 170                 175

Leu Ile Tyr Ala Val Gly Gly Leu Asn Ser Ala Gly Asp Ser Leu Asn
            180                 185                 190

Val Val Glu Val Phe Asp Pro Ile Ala Asn Cys Trp Glu Arg Cys Arg
        195                 200                 205

Pro Met Thr Thr Ala Arg Ser Arg Val Gly Val Ala Val Val Asn Gly
    210                 215                 220

Leu Leu Tyr Ala Ile Gly Gly Tyr Asp Gly Gln Leu Arg Leu Ser Thr
225                 230                 235                 240

Val Glu Ala Tyr Asn Pro Glu Thr Asp Thr Trp Thr Arg Val Gly Ser
                245                 250                 255

Met Asn Ser Lys Arg Ser Ala Met Gly Thr Val Val Leu Asp Gly Gln
            260                 265                 270

Ile Tyr Val Cys Gly Gly Tyr Asp Gly Asn Ser Ser Leu Ser Ser Val
        275                 280                 285

Glu Thr Tyr Ser Pro Glu Thr Asp Lys Trp Thr Val Val Thr Ser Met
    290                 295                 300

Ser Ser Asn Arg Ser Ala Ala Gly Val Thr Val Phe Glu Gly Arg Ile
305                 310                 315                 320

Tyr Val Ser Gly Gly His Asp Gly Leu Gln Ile Phe Ser Ser Val Glu
                325                 330                 335

His Tyr Asn His His Thr Ala Thr Trp His Pro Ala Ala Gly Met Leu
            340                 345                 350

Asn Lys Arg Cys Arg His Gly Ala Ala Ser Leu Gly Ser Lys Met Phe
        355                 360                 365

Val Cys Gly Gly Tyr Asp Gly Ser Gly Phe Leu Ser Ile Ala Glu Met
    370                 375                 380

Tyr Ser Ser Val Ala Asp Gln Trp Cys Leu Ile Val Pro Met His Thr
385                 390                 395                 400

Arg Arg Ser Arg Val Ser Leu Val Ala Ser Cys Gly Arg Leu Tyr Ala
                405                 410                 415

Val Gly Gly Tyr Asp Gly Gln Ser Asn Leu Ser Ser Val Glu Met Tyr
            420                 425                 430

Asp Pro Glu Thr Asp Cys Trp Thr Phe Met Ala Pro Met Ala Cys His
        435                 440                 445

Glu Gly Gly Val Gly Val Gly Cys Ile Pro Leu Leu Thr Ile
    450                 455                 460
```

<210> SEQ ID NO 31
<211> LENGTH: 4612
<212> TYPE: DNA
<213> ORGANISM: Homo sapiens

<400> SEQUENCE: 31

```
ccaactgaat tttcagatga gatgagaagg tcatgctttt ccacctttga gctcccactt     60
tgaccagctc tgccagtcct gagccagaag gtcaacagtt aaaaagaaga gattggggac    120
cacaaattca gtgcccaccg gattgtctta gcagcctcga tcccgtattt ccatgctatg    180
tttacaaatg acatgatgga gtgcaagcag gatgagattg taatgcaagg aatggaccca    240
agtgccctgg aggctctgat caactttgcc tacaacggca accttgccat tgaccagcaa    300
aatgtccagt cattgctgat gggggcgagc ttcctgcagc tgcagagcat caaagacgcc    360
tgctgcacat tccttcgaga acggcttcac ccaaaaaact gcctgggtgt gcgccagttt    420
gctgagacaa tgatgtgtgc tgtgctgtac gacgctgcca acagcttcat ccaccagcac    480
tttgtggagg tgtccatgtc agaagagttc ctggccctgc ccttggaaga cgtgcttgag    540
ctggtgtctc gggatgagct gaatgtcaaa tctgaggagc aggtctttga agctgcattg    600
gcctgggtca gatacgaccg ggagcagagg ggtccctacc tgcctgagct gctgtccaat    660
atccgcctgc ccctctgtcg gccccagttc ctttcagaca gagtacagca ggatgacctg    720
gtgcgttgct gccacaaatg cagggacctg gtagacgaag caaaggacta ccacctcatg    780
ccagagcgcc ggccccacct gccagctttc agaacccggc cacgctgctg cacatccatc    840
gctggactta tctacgctgt aggggggcctc aactcagcag caaattttta tgcaggtgat    900
tccctgaatg tggtggaagt gttcgacccc attgccaatt gctgggagag atgccgtccc    960
atgacaacag cccgcagccg cgttggcgtg gctgtggtga acgggcttct ctatgccatc   1020
ggaggatatg acggccagct acggctgagc actgtggagg cctacaaccc ggagacagac   1080
acatggacca gagtggggag catgaatagc aagagaagct ctgtctgttt cagtgccatg   1140
gggacagtcg tgctggatgg gcagatctac gtctgtgggg gctacgatgg caactcttcc   1200
ctcagctccg tggagaccta ctcacctgag acggacaaat ggacagtggt gacctcgatg   1260
agctcgaatc gcagtgctgc tggggttaca gtctttgagg gcaggatata tgtgtcaggc   1320
ggccatgatg gtttgcagat cttcagcagt gtggaacact acaaccacca cacagccacc   1380
tggcaccctg cagctggcat gctcaacaag cgctgccggc acggagccgc ctccctgggg   1440
agcaagatgt ttgtctgcgg gggctacgat ggctctggct tcctcagcat tgccgagatg   1500
tacagctctg tggcagacca gtggtgcctg attgtcccca tgcacacgcg caggagccgg   1560
gtctccctgg tggccagctg tgggcgcctc tacgctgttg gggggctacga cggacagtca   1620
aacctaagct cagtggagat gtatgaccca gagacagact gctggacatt catggccccc   1680
atggcgtgcc atgagggagg ggtcggtgtg ggctgcatcc ctctcctcac catctaaggc   1740
agaggatggg atgtggtggg gcagggatct ggtacagaca taggcgcttc cttccaggaa   1800
cagtccctca ggagaggcag tggaccagaa gagatggcga aacgtgagct cgccggaggt   1860
acagtttttc caggtgctta agccctcccc cactgtgcca cccttgtgac cttcaggctt   1920
gggtcatcaa gatgcacagc atggaacaca agctcctctg gatcctgcag ctggtgacat   1980
ggaactgttt tctggtccac atgaacacag gctccatcca ggcccagctc ctacccaccg   2040
cctctctgtg ggccagctgt tcacagaagg ccttccatct gatgctcccc atcgcctgct   2100
tgctctccag ccgagtctgg ccaatttgcc atggggaggc tgcagtgtcc aagcctgctg   2160
```

```
gaaactggga tgtagctggg gacgaaagga cagacccaag cgttctccct gcctgagatg   2220
gtgtggccac agcagtggaa ggctgcacac aggcacattc cttcttccac agtggggcac   2280
caaggattct gtcctcattg ctgggtaagc agggagaaga gaagttttcc ccatgtctaa   2340
ttttgggatt tcagtgaggc cttttgatct gtccaggaga acagaaggga aaaaaagata   2400
cttgaaagaa actgaaggaa atttaaacaa agaaacactt gaaagaaact ggaaagaaaa   2460
ataatttttt tatgtgaaca aattttgcaa gaagaaaaaa gcataaaaga cactaacggc   2520
aaatctatgt ttaaatggaa aatcgtctaa ctggagaagg gcggtatcca ccccacattc   2580
ggatcccagg gtcctgaggc ctcgcattga gctgggggtt ccctctgagc cccagtgtgt   2640
gtggaatcag tgcactcttg actgggcctg tagtaaggtg ctcatggggt ttgtcttctc   2700
acccaccatc agaggacttt taaaatcata ggcgtagaga gttaggctat ctgctgaatt   2760
actgccactc ttcttggtgg gggctcctag ctgtggctgg gggctccagg cgcccctgtg   2820
attacctcct actgccacca tggcgctcat tcagattccc cactctcact aacattgctt   2880
cctttttga ccagcaggaa acagcaggtc tggccagatt ctcacttgcc catcaatctc   2940
gttcttggat gatttccctc attgtgatgc ttctggggca cgttgaccat atgcacctct   3000
agaacctaac cagggcttcc ttctaccagc tgtgggcggg cttggtctgg taaccttgtc   3060
tgctctgcca ttccactgct cctccatcca ctcgccaatc ccaagagtct ggcctccctc   3120
cagccctggg cagactgacc agcaaggtgg acctttacat tcaagcacag ctggctttta   3180
tgacataaag aactaaaggc cgaaagaatc tcttgctgct gcaaagaaca gattttatat   3240
ttcttcctct aatcttggca aatgaccttt accttttgga aagatttcat attgcttcct   3300
cctccctgga taggacctaa tgtagcacag cgggactcaa agaggaggac attttctctt   3360
gccagtgcac tgggcagtgg ggctgtcctt caactgctgc tgccaaaatt ggttttctaa   3420
aattcttcca gtagagacta aaagaagatt caattcctgt aacccaagac tgagtcttag   3480
ggctccagtc tccacctgct tggtttccta tcctttgctg cctgcctggg gtggcctgga   3540
agcctgttca gaaaggcaca atgtggagcc tggggtgtct cccccacccc aggaccgtca   3600
ggtttaccag tgtgtgcaat cgccatgtat tcagagggaa gtacctttgt tacctacaac   3660
ttaggagcta ggcctctgct acaagcactt gaaaatgata tttttatttt taacgtctca   3720
acaatctgat atcggatgtc gtttaacctg ggctcgtggt agggctccag catttctccc   3780
tccttcctgg tttgcctgta ggggtagact cggaaggtgg gtggggtgtg catttcctgt   3840
taggagtgta tcagtgcttg tcttattata agcccctttc ttttgtgaat ttgaagtagc   3900
accaacaagc ctggattgtg aaggtattaa gaatcggtct gtgggctact gagtgggtcc   3960
ttaggatact ggcccagatt ttgccactgg gtatggcaga tcatttttcta ccatggcctg   4020
ctgctcttgt agtggacttc ctgagtccaa tcccacctcc tggtgtagaa tttacactgc   4080
tgcacctgag gtcgatgttt caaagtaaga tcaagccagt gttttgatct gggctctgag   4140
cacaagtcag gaaacaccaa catattcaca ctctcccagt aggttcctca gtccgatggt   4200
gaatggctat tcgtaaatgg ctggtctggc tctttggtgt tggagccttt ccaatagccc   4260
catgaaaaga agcatcaccc aaggatattg taaaaaggat gtaacaagga gatagggtag   4320
acattgtact cagtgggcct tggggcctag cccagctctg agcagaggac tgtggcattc   4380
actgtccttg agtgtttcac cttcttggat aacacacggg ccttctcttc tggatttcat   4440
cagagattac agccagatgg gggctgaaga ccatcctctt gaccacagag gtgtgactgt   4500
```

```
gggaattcct cccaatttat ggtttcccag aaaatcttag ttccttttat ttatagaatg   4560

catgtctttt gtgttaagaa accaaagaga aataaagaga acactcctaa ta           4612


<210> SEQ ID NO 32
<211> LENGTH: 1419
<212> TYPE: DNA
<213> ORGANISM: Homo sapiens

<400> SEQUENCE: 32

atgggggcga gcttcctgca gctgcagagc atcaaagacg cctgctgcac attccttcga     60

gaacggcttc acccaaaaaa ctgcctgggt gtgcgccagt ttgctgagac aatgatgtgt    120

gctgtgctgt acgacgctgc caacagcttc atccaccagc actttgtgga ggtgtccatg    180

tcagaagagt tcctggccct gcccttggaa gacgtgcttg agctggtgtc tcgggatgag    240

ctgaatgtca aatctgagga gcaggtcttt gaagctgcat tggcctgggt cagatacgac    300

cgggagcaga ggggtcccta cctgcctgag ctgctgtcca atatccgcct gcccctctgt    360

cggccccagt tcctttcaga cagagtacag caggatgacc tggtgcgttg ctgccacaaa    420

tgcagggacc tggtagacga agcaaaggac taccacctca tgccagagcg ccggccccac    480

ctgccagctt tcagaacccg gccacgctgc tgcacatcca tcgctggact tatctacgct    540

gtagggggcc tcaactcagc agcaaatttt tatgcaggtg attccctgaa tgtggtggaa    600

gtgttcgacc ccattgccaa ttgctgggag agatgccgtc ccatgacaac agcccgcagc    660

cgcgttggcg tggctgtggt gaacgggctt ctctatgcca tcggaggata tgacggccag    720

ctacggctga gcactgtgga ggcctacaac ccggagacag acacatggac cagagtgggg    780

agcatgaata gcaagagaag ctctgtctgt ttcagtgcca tggggacagt cgtgctggat    840

gggcagatct acgtctgtgg gggctacgat ggcaactctt ccctcagctc cgtggagacc    900

tactcacctg agacggacaa atggacagtg gtgacctcga tgagctcgaa tcgcagtgct    960

gctggggtta cagtctttga gggcaggata tatgtgtcag gcggccatga tggtttgcag   1020

atcttcagca gtgtggaaca ctacaaccac cacacagcca cctggcaccc tgcagctggc   1080

atgctcaaca agcgctgccg gcacggagcc gcctccctgg ggagcaagat gtttgtctgc   1140

gggggctacg atggctctgg cttcctcagc attgccgaga tgtacagctc tgtggcagac   1200

cagtggtgcc tgattgtccc catgcacacg cgcaggagcc gggtctccct ggtggccagc   1260

tgtgggcgcc tctacgctgt tgggggctac gacggacagt caaacctaag ctcagtggag   1320

atgtatgacc cagagacaga ctgctggaca ttcatggccc ccatggcgtg ccatgaggga   1380

ggggtcggtg tgggctgcat ccctctcctc accatctaa                          1419


<210> SEQ ID NO 33
<211> LENGTH: 519
<212> TYPE: PRT
<213> ORGANISM: Homo sapiens

<400> SEQUENCE: 33

Met Phe Thr Asn Asp Met Met Glu Cys Lys Gln Asp Glu Ile Val Met
1               5                   10                  15

Gln Gly Met Asp Pro Ser Ala Leu Glu Ala Leu Ile Asn Phe Ala Tyr
            20                  25                  30

Asn Gly Asn Leu Ala Ile Asp Gln Gln Asn Val Gln Ser Leu Leu Met
        35                  40                  45

Gly Ala Ser Phe Leu Gln Leu Gln Ser Ile Lys Asp Ala Cys Cys Thr
    50                  55                  60
```

```
Phe Leu Arg Glu Arg Leu His Pro Lys Asn Cys Leu Gly Val Arg Gln
65                  70                  75                  80

Phe Ala Glu Thr Met Met Cys Ala Val Leu Tyr Asp Ala Ala Asn Ser
                85                  90                  95

Phe Ile His Gln His Phe Val Glu Val Ser Met Ser Glu Glu Phe Leu
            100                 105                 110

Ala Leu Pro Leu Glu Asp Val Leu Glu Leu Val Ser Arg Asp Glu Leu
        115                 120                 125

Asn Val Lys Ser Glu Glu Gln Val Phe Glu Ala Ala Leu Ala Trp Val
    130                 135                 140

Arg Tyr Asp Arg Glu Gln Arg Gly Pro Tyr Leu Pro Glu Leu Leu Ser
145                 150                 155                 160

Asn Ile Arg Leu Pro Leu Cys Arg Pro Gln Phe Leu Ser Asp Arg Val
                165                 170                 175

Gln Gln Asp Asp Leu Val Arg Cys Cys His Lys Cys Arg Asp Leu Val
            180                 185                 190

Asp Glu Ala Lys Asp Tyr His Leu Met Pro Glu Arg Arg Pro His Leu
        195                 200                 205

Pro Ala Phe Arg Thr Arg Pro Arg Cys Cys Thr Ser Ile Ala Gly Leu
    210                 215                 220

Ile Tyr Ala Val Gly Gly Leu Asn Ser Ala Ala Asn Phe Tyr Ala Gly
225                 230                 235                 240

Asp Ser Leu Asn Val Val Glu Val Phe Asp Pro Ile Ala Asn Cys Trp
                245                 250                 255

Glu Arg Cys Arg Pro Met Thr Thr Ala Arg Ser Arg Val Gly Val Ala
            260                 265                 270

Val Val Asn Gly Leu Leu Tyr Ala Ile Gly Gly Tyr Asp Gly Gln Leu
        275                 280                 285

Arg Leu Ser Thr Val Glu Ala Tyr Asn Pro Glu Thr Asp Thr Trp Thr
    290                 295                 300

Arg Val Gly Ser Met Asn Ser Lys Arg Ser Ser Val Cys Phe Ser Ala
305                 310                 315                 320

Met Gly Thr Val Val Leu Asp Gly Gln Ile Tyr Val Cys Gly Gly Tyr
                325                 330                 335

Asp Gly Asn Ser Ser Leu Ser Ser Val Glu Thr Tyr Ser Pro Glu Thr
            340                 345                 350

Asp Lys Trp Thr Val Val Thr Ser Met Ser Ser Asn Arg Ser Ala Ala
        355                 360                 365

Gly Val Thr Val Phe Glu Gly Arg Ile Tyr Val Ser Gly Gly His Asp
    370                 375                 380

Gly Leu Gln Ile Phe Ser Ser Val Glu His Tyr Asn His His Thr Ala
385                 390                 395                 400

Thr Trp His Pro Ala Ala Gly Met Leu Asn Lys Arg Cys Arg His Gly
                405                 410                 415

Ala Ala Ser Leu Gly Ser Lys Met Phe Val Cys Gly Gly Tyr Asp Gly
            420                 425                 430

Ser Gly Phe Leu Ser Ile Ala Glu Met Tyr Ser Ser Val Ala Asp Gln
        435                 440                 445

Trp Cys Leu Ile Val Pro Met His Thr Arg Arg Ser Arg Val Ser Leu
    450                 455                 460

Val Ala Ser Cys Gly Arg Leu Tyr Ala Val Gly Gly Tyr Asp Gly Gln
465                 470                 475                 480
```

```
Ser Asn Leu Ser Ser Val Glu Met Tyr Asp Pro Glu Thr Asp Cys Trp
                485                 490                 495

Thr Phe Met Ala Pro Met Ala Cys His Glu Gly Gly Val Gly Val Gly
            500                 505                 510

Cys Ile Pro Leu Leu Thr Ile
        515


<210> SEQ ID NO 34
<211> LENGTH: 1398
<212> TYPE: DNA
<213> ORGANISM: Mus musculus

<400> SEQUENCE: 34

ttcccctggc tccagccggc gcaagcagcg gcggcggtgg cagcgggcga ggatctgcgg      60

ccccgcgagg ccatgaaggt gaagaaaggc ggcggcggga ccgggtcggg ggcggagccc     120

gttccagggg cctcgaaccg gagcgcggag cccacgcggg agcctggggc ggaagctgag     180

tccgggtccg agtcggagcc ggagccaggc ccggggccca ggctggggcc gctgcagggc     240

aagcagccca tcgggccgga ggatgtgctg ggctgcagc ggatcacggg tgactacctg     300

tgctcccctg aggaaaatat ctacaagatt gacttcgtca ggttcaagat ccgtgacatg     360

gactcaggga ctgtcctttt tgaaatcaag aagccccctg tttcggaacg gttgcccatc     420

aaccggcggg acctggaccc caatgcaggg cgctttgttc gctaccagtt cacacctgcc     480

ttcctccgcc taaggcaggt gggagccacg gtggagttca cagtgggaga caagccggtc     540

aacaacttcc gcatgatcga gaggcactac tttcgaaacc agctcctcaa aagcttcgac     600

ttccactttg gcttctgcat ccccagcagc aagaacacct gtgagcacat ctatgacttc     660

cctcctctct ccgaggagct aattctgaag tccctacagg gtctggctca gggtcctgac     720

ctttgccctg gatgggcctc tcttgcagtc agtgagatga ttcgtcaccc gtatgagacc     780

cagtctgaca gcttctactt cgtggatgac cggctggtga tgcataacaa agcagactat     840

tcctacagtg ggacaccctg accccctaatg ctgcccctga ggctctggcc tagaccctgt     900

gctgtaacct ctccgacatc atctccactt ggggatggat ccggtggctc tggaccctga     960

gtcagtctcg agaggaaagg tgtccagcat ccctaggcaa acctctggag ctagtgggag    1020

gggcagcagg gggaggctgg ctgtccccat gttcaggaag gcctcctgca agaggaggac    1080

tcctggatgc ctcgctaggt ccactgggcc tgagtttcag agtagtgccc ccttcttgac    1140

cgtgactaga tcaggttagg gaccatttcc tgtcccttgc ccaccacctc caggctattt    1200

atagttgtcg gttcacagac aaagatccac agtgggtacc ctgctctgag ccctggcctc    1260

ctccatcagg ggccaagaaa ctacccgagg tgtgagaggg gcgggtccag atcgcagcct    1320

gtaagacctg gacaaactgt atatagtttt caataaacct tttctgttct tgggtgcggc    1380

caaaaaaaaa aaaaaaaa                                                  1398


<210> SEQ ID NO 35
<211> LENGTH: 789
<212> TYPE: DNA
<213> ORGANISM: Mus musculus

<400> SEQUENCE: 35

atgaaggtga agaaaggcgg cggcgggacc gggtcggggg cggagcccgt tccaggggcc      60

tcgaaccgga gcgcggagcc cacgcgggag cctggggcgg aagctgagtc cgggtccgag     120

tcggagccgg agccaggccc ggggcccagg ctggggccgc tgcagggcaa gcagcccatc     180
```

-continued

```
gggccggagg atgtgctggg gctgcagcgg atcacgggtg actacctgtg ctcccctgag    240

gaaaatatct acaagattga cttcgtcagg ttcaagatcc gtgacatgga ctcagggact    300

gtcctttttg aaatcaagaa gccccctgtt tcggaacggt tgcccatcaa ccggcgggac    360

ctggacccca atgcagggcg ctttgttcgc taccagttca cacctgcctt cctccgccta    420

aggcaggtgg gagccacggt ggagttcaca gtgggagaca agccggtcaa caacttccgc    480

atgatcgaga ggcactactt tcgaaaccag ctcctcaaaa gcttcgactt ccactttggc    540

ttctgcatcc ccagcagcaa gaacacctgt gagcacatct atgacttccc tcctctctcc    600

gaggagctaa ttctgaagtc cctacagggt ctggctcagg gtcctgacct ttgccctgga    660

tgggcctctc ttgcagtcag tgagatgatt cgtcacccgt atgagaccca gtctgacagc    720

ttctacttcg tggatgaccg gctggtgatg cataacaaag cagactattc ctacagtggg    780

acaccctga                                                            789


<210> SEQ ID NO 36
<211> LENGTH: 262
<212> TYPE: PRT
<213> ORGANISM: Mus musculus

<400> SEQUENCE: 36

Met Lys Val Lys Lys Gly Gly Gly Gly Thr Gly Ser Gly Ala Glu Pro
1               5                   10                  15

Val Pro Gly Ala Ser Asn Arg Ser Ala Glu Pro Thr Arg Glu Pro Gly
            20                  25                  30

Ala Glu Ala Glu Ser Gly Ser Glu Ser Glu Pro Glu Pro Gly Pro Gly
        35                  40                  45

Pro Arg Leu Gly Pro Leu Gln Gly Lys Gln Pro Ile Gly Pro Glu Asp
    50                  55                  60

Val Leu Gly Leu Gln Arg Ile Thr Gly Asp Tyr Leu Cys Ser Pro Glu
65                  70                  75                  80

Glu Asn Ile Tyr Lys Ile Asp Phe Val Arg Phe Lys Ile Arg Asp Met
                85                  90                  95

Asp Ser Gly Thr Val Leu Phe Glu Ile Lys Lys Pro Pro Val Ser Glu
            100                 105                 110

Arg Leu Pro Ile Asn Arg Arg Asp Leu Asp Pro Asn Ala Gly Arg Phe
        115                 120                 125

Val Arg Tyr Gln Phe Thr Pro Ala Phe Leu Arg Leu Arg Gln Val Gly
    130                 135                 140

Ala Thr Val Glu Phe Thr Val Gly Asp Lys Pro Val Asn Asn Phe Arg
145                 150                 155                 160

Met Ile Glu Arg His Tyr Phe Arg Asn Gln Leu Leu Lys Ser Phe Asp
                165                 170                 175

Phe His Phe Gly Phe Cys Ile Pro Ser Ser Lys Asn Thr Cys Glu His
            180                 185                 190

Ile Tyr Asp Phe Pro Pro Leu Ser Glu Glu Leu Ile Leu Lys Ser Leu
        195                 200                 205

Gln Gly Leu Ala Gln Gly Pro Asp Leu Cys Pro Gly Trp Ala Ser Leu
    210                 215                 220

Ala Val Ser Glu Met Ile Arg His Pro Tyr Glu Thr Gln Ser Asp Ser
225                 230                 235                 240

Phe Tyr Phe Val Asp Asp Arg Leu Val Met His Asn Lys Ala Asp Tyr
                245                 250                 255

Ser Tyr Ser Gly Thr Pro
```

260

<210> SEQ ID NO 37
<211> LENGTH: 1156
<212> TYPE: DNA
<213> ORGANISM: Mus musculus

<400> SEQUENCE: 37

```
gtcctctcaa gaccagcctt gcctgatgaa tgtagatgtc atgccacagg actacctgtg     60
ctcccctgag gaaaatatct acaagattga cttcgtcagg ttcaagatcc gtgacatgga    120
ctcagggact gtcctttttg aaatcaagaa gccccctgtt tcggaacggt tgcccatcaa    180
ccggcgggac ctggacccca atgcagggcg ctttgttcgc taccagttca cacctgcctt    240
cctccgccta aggcaggtgg gagccacggt ggagttcaca gtgggagaca agccggtcaa    300
caacttccgc atgatcgaga ggcactactt tcgaaaccag ctcctcaaaa gcttcgactt    360
ccactttggc ttctgcatcc ccagcagcaa gaacacctgt gagcacatct atgacttccc    420
tcctctctcc gaggagctaa ttctgaagtc cctacagggt ctggctcagg gtcctgacct    480
ttgccctgga tgggcctctc ttgcagtcag tgagatgatt cgtcacccgt atgagaccca    540
gtctgacagc ttctacttcg tggatgaccg gctggtgatg cataacaaag cagactattc    600
ctacagtggg acaccctgac ccctaatgct gcccctgagg ctctggccta gaccctgtgc    660
tgtaacctct ccgacatcat ctccacttgg ggatggatcc ggtggctctg gaccctgagt    720
cagtctcgag aggaaaggtg tccagcatcc ctaggcaaac ctctggagct agtgggaggg    780
gcagcagggg gaggctggct gtccccatgt tcaggaaggc ctcctgcaag aggaggactc    840
ctggatgcct cgctaggtcc actgggcctg agtttcagag tagtgccccc ttcttgaccg    900
tgactagatc aggttaggga ccatttcctg tcccttgccc accacctcca ggctatttat    960
agttgtcggt tcacagacaa agatccacag tgggtaccct gctctgagcc ctggcctcct   1020
ccatcagggg ccaagaaact acccgaggtg tgagaggggc gggtccagat cgcagcctgt   1080
aagacctgga caaactgtat atagttttca ataaaccttt tctgttcttg ggtgcggcca   1140
aaaaaaaaaa aaaaaa                                                   1156
```

<210> SEQ ID NO 38
<211> LENGTH: 594
<212> TYPE: DNA
<213> ORGANISM: Mus musculus

<400> SEQUENCE: 38

```
atgaatgtag atgtcatgcc acaggactac ctgtgctccc ctgaggaaaa tatctacaag     60
attgacttcg tcaggttcaa gatccgtgac atggactcag ggactgtcct ttttgaaatc    120
aagaagcccc ctgtttcgga acggttgccc atcaaccggc gggacctgga ccccaatgca    180
gggcgctttg ttcgctacca gttcacacct gccttcctcc gcctaaggca ggtgggagcc    240
acggtggagt tcacagtggg agacaagccg gtcaacaact tccgcatgat cgagaggcac    300
tactttcgaa accagctcct caaaagcttc gacttccact ttggcttctg catccccagc    360
agcaagaaca cctgtgagca catctatgac ttccctcctc tctccgagga gctaattctg    420
aagtccctac agggtctggc tcagggtcct gacctttgcc ctggatgggc ctctcttgca    480
gtcagtgaga tgattcgtca cccgtatgag acccagtctg acagcttcta cttcgtggat    540
gaccggctgg tgatgcataa caaagcagac tattcctaca gtgggacacc ctga          594
```

<210> SEQ ID NO 39
<211> LENGTH: 197
<212> TYPE: PRT
<213> ORGANISM: Mus musculus

<400> SEQUENCE: 39

```
Met Asn Val Asp Val Met Pro Gln Asp Tyr Leu Cys Ser Pro Glu Glu
1               5                   10                  15

Asn Ile Tyr Lys Ile Asp Phe Val Arg Phe Lys Ile Arg Asp Met Asp
            20                  25                  30

Ser Gly Thr Val Leu Phe Glu Ile Lys Lys Pro Pro Val Ser Glu Arg
        35                  40                  45

Leu Pro Ile Asn Arg Arg Asp Leu Asp Pro Asn Ala Gly Arg Phe Val
    50                  55                  60

Arg Tyr Gln Phe Thr Pro Ala Phe Leu Arg Leu Arg Gln Val Gly Ala
65                  70                  75                  80

Thr Val Glu Phe Thr Val Gly Asp Lys Pro Val Asn Asn Phe Arg Met
                85                  90                  95

Ile Glu Arg His Tyr Phe Arg Asn Gln Leu Leu Lys Ser Phe Asp Phe
            100                 105                 110

His Phe Gly Phe Cys Ile Pro Ser Ser Lys Asn Thr Cys Glu His Ile
        115                 120                 125

Tyr Asp Phe Pro Pro Leu Ser Glu Glu Leu Ile Leu Lys Ser Leu Gln
    130                 135                 140

Gly Leu Ala Gln Gly Pro Asp Leu Cys Pro Gly Trp Ala Ser Leu Ala
145                 150                 155                 160

Val Ser Glu Met Ile Arg His Pro Tyr Glu Thr Gln Ser Asp Ser Phe
                165                 170                 175

Tyr Phe Val Asp Asp Arg Leu Val Met His Asn Lys Ala Asp Tyr Ser
            180                 185                 190

Tyr Ser Gly Thr Pro
        195
```

<210> SEQ ID NO 40
<211> LENGTH: 1090
<212> TYPE: DNA
<213> ORGANISM: Mus musculus

<400> SEQUENCE: 40

```
gtcctctcaa gaccagcctt gcctgatgaa tgtagatgtc atgccacagg actacctgtg     60

ctcccctgag gaaaatatct acaagattga cttcgtcagg ttcaagatcc gtgacatgga    120

ctcagggact gtcctttttg aaatcaagaa gccccctgtt tcggaacggt tgcccatcaa    180

ccggcgggac ctggacccca atgcagggcg ctttgttcgc taccagttca cacctgcctt    240

cctccgccta aggcaggtgg gagccacggt ggagttcaca gtgggagaca agccggtcaa    300

caacttccgc atgatcgaga ggcactactt tcgaaaccag ctcctcaaaa gcttcgactt    360

ccactttggc ttctgcatcc ccagcagcaa gaacacctgt gagcacatct atgacttccc    420

tcctctctcc gaggagctaa tcagtgagat gattcgtcac ccgtatgaga cccagtctga    480

cagcttctac ttcgtggatg accggctggt gatgcataac aaagcagact attcctacag    540

tgggacaccc tgaccctaa tgctgcccct gaggctctgg cctagaccct gtgctgtaac    600

ctctccgaca tcatctccac ttggggatgg atccggtggc tctggaccct gagtcagtct    660

cgagaggaaa ggtgtccagc atccctaggc aaacctctgg agctagtggg aggggcagca    720

gggggaggct ggctgtcccc atgttcagga aggcctcctg caagaggagg actcctggat    780
```

```
gcctcgctag gtccactggg cctgagtttc agagtagtgc ccccttcttg accgtgacta    840

gatcaggtta gggaccattt cctgtccctt gcccaccacc tccaggctat ttatagttgt    900

cggttcacag acaaagatcc acagtgggta ccctgctctg agccctggcc tcctccatca    960

ggggccaaga aactacccga ggtgtgagag gggcgggtcc agatcgcagc ctgtaagacc   1020

tggacaaact gtatatagtt ttcaataaac cttttctgtt cttgggtgcg gccaaaaaaa   1080

aaaaaaaaaa                                                          1090


<210> SEQ ID NO 41
<211> LENGTH: 528
<212> TYPE: DNA
<213> ORGANISM: Mus musculus

<400> SEQUENCE: 41

atgaatgtag atgtcatgcc acaggactac ctgtgctccc ctgaggaaaa tatctacaag     60

attgacttcg tcaggttcaa gatccgtgac atggactcag ggactgtcct tttgaaatc    120

aagaagcccc ctgtttcgga acggttgccc atcaaccggc gggacctgga ccccaatgca    180

gggcgctttg ttcgctacca gttcacacct gccttcctcc gcctaaggca ggtgggagcc    240

acggtggagt tcacagtggg agacaagccg gtcaacaact tccgcatgat cgagaggcac    300

tactttcgaa accagctcct caaaagcttc gacttccact ttggcttctg catccccagc    360

agcaagaaca cctgtgagca catctatgac ttccctcctc tctccgagga gctaatcagt    420

gagatgattc gtcacccgta tgagacccag tctgacagct tctacttcgt ggatgaccgg    480

ctggtgatgc ataacaaagc agactattcc tacagtggga caccctga                528


<210> SEQ ID NO 42
<211> LENGTH: 175
<212> TYPE: PRT
<213> ORGANISM: Mus musculus

<400> SEQUENCE: 42

Met Asn Val Asp Val Met Pro Gln Asp Tyr Leu Cys Ser Pro Glu Glu
1               5                   10                  15

Asn Ile Tyr Lys Ile Asp Phe Val Arg Phe Lys Ile Arg Asp Met Asp
            20                  25                  30

Ser Gly Thr Val Leu Phe Glu Ile Lys Lys Pro Pro Val Ser Glu Arg
        35                  40                  45

Leu Pro Ile Asn Arg Arg Asp Leu Asp Pro Asn Ala Gly Arg Phe Val
    50                  55                  60

Arg Tyr Gln Phe Thr Pro Ala Phe Leu Arg Leu Arg Gln Val Gly Ala
65                  70                  75                  80

Thr Val Glu Phe Thr Val Gly Asp Lys Pro Val Asn Asn Phe Arg Met
                85                  90                  95

Ile Glu Arg His Tyr Phe Arg Asn Gln Leu Leu Lys Ser Phe Asp Phe
            100                 105                 110

His Phe Gly Phe Cys Ile Pro Ser Ser Lys Asn Thr Cys Glu His Ile
        115                 120                 125

Tyr Asp Phe Pro Pro Leu Ser Glu Glu Leu Ile Ser Glu Met Ile Arg
    130                 135                 140

His Pro Tyr Glu Thr Gln Ser Asp Ser Phe Tyr Phe Val Asp Asp Arg
145                 150                 155                 160

Leu Val Met His Asn Lys Ala Asp Tyr Ser Tyr Ser Gly Thr Pro
                165                 170                 175
```

<210> SEQ ID NO 43
<211> LENGTH: 1139
<212> TYPE: DNA
<213> ORGANISM: Mus musculus

<400> SEQUENCE: 43

```
ctttttcttg gctgaggaga ggaagtggct gccttcctag gcagcccctg atcctcgctc     60
cttgtaaggg cagagaggcc cacaagttga gtttgcagta ctacctgtgc tcccctgagg    120
aaaatatcta caagattgac ttcgtcaggt tcaagatccg tgacatggac tcagggactg    180
tcctttttga aatcaagaag cccctgtttt cggaacggtt gcccatcaac cggcgggacc    240
tggaccccaa tgcagggcgc tttgttcgct accagttcac acctgccttc ctccgcctaa    300
ggcaggtggg agccacggtg gagttcacag tgggagacaa gccggtcaac aacttccgca    360
tgatcgagag gcactacttt cgaaaccagc tcctcaaaag cttcgacttc cactttggct    420
tctgcatccc cagcagcaag aacacctgtg agcacatcta tgacttccct cctctctccg    480
aggagctaat cagtgagatg attcgtcacc cgtatgagac ccagtctgac agcttctact    540
tcgtggatga ccggctggtg atgcataaca aagcagacta ttcctacagt gggacaccct    600
gacccctaat gctgcccctg aggctctggc ctagaccctg tgctgtaacc tctccgacat    660
catctccact tggggatgga tccggtggct ctggaccctg agtcagtctc gagaggaaag    720
gtgtccagca tccctaggca aacctctgga gctagtggga ggggcagcag gggggaggctg   780
gctgtcccca tgttcaggaa ggcctcctgc aagaggagga ctcctggatg cctcgctagg    840
tccactgggc ctgagtttca gagtagtgcc cccttcttga ccgtgactag atcaggttag    900
ggaccatttc ctgtcccttg cccaccacct ccaggctatt tatagttgtc ggttcacaga    960
caaagatcca cagtgggtac cctgctctga gccctggcct cctccatcag gggccaagaa   1020
actacccgag gtgtgagagg ggcgggtcca gatcgcagcc tgtaagacct ggacaaactg   1080
tatatagttt tcaataaacc ttttctgttc ttgggtgcgg ccaaaaaaaa aaaaaaaaa    1139
```

<210> SEQ ID NO 44
<211> LENGTH: 438
<212> TYPE: DNA
<213> ORGANISM: Mus musculus

<400> SEQUENCE: 44

```
atggactcag ggactgtcct ttttgaaatc aagaagcccc ctgtttcgga acggttgccc     60
atcaaccggc gggacctgga ccccaatgca gggcgctttg ttcgctacca gttcacacct    120
gccttcctcc gcctaaggca ggtgggagcc acggtggagt tcacagtggg agacaagccg    180
gtcaacaact tccgcatgat cgagaggcac tactttcgaa accagctcct caaaagcttc    240
gacttccact ttggcttctg catccccagc agcaagaaca cctgtgagca catctatgac    300
ttccctcctc tctccgagga gctaatcagt gagatgattc gtcacccgta tgagacccag    360
tctgacagct tctacttcgt ggatgaccgg ctggtgatgc ataacaaagc agactattcc    420
tacagtggga caccctga                                                  438
```

<210> SEQ ID NO 45
<211> LENGTH: 145
<212> TYPE: PRT
<213> ORGANISM: Mus musculus

<400> SEQUENCE: 45

```
Met Asp Ser Gly Thr Val Leu Phe Glu Ile Lys Lys Pro Pro Val Ser
1               5                   10                  15

Glu Arg Leu Pro Ile Asn Arg Arg Asp Leu Asp Pro Asn Ala Gly Arg
            20                  25                  30

Phe Val Arg Tyr Gln Phe Thr Pro Ala Phe Leu Arg Leu Arg Gln Val
        35                  40                  45

Gly Ala Thr Val Glu Phe Thr Val Gly Asp Lys Pro Val Asn Asn Phe
    50                  55                  60

Arg Met Ile Glu Arg His Tyr Phe Arg Asn Gln Leu Leu Lys Ser Phe
65                  70                  75                  80

Asp Phe His Phe Gly Phe Cys Ile Pro Ser Ser Lys Asn Thr Cys Glu
                85                  90                  95

His Ile Tyr Asp Phe Pro Pro Leu Ser Glu Glu Leu Ile Ser Glu Met
            100                 105                 110

Ile Arg His Pro Tyr Glu Thr Gln Ser Asp Ser Phe Tyr Phe Val Asp
        115                 120                 125

Asp Arg Leu Val Met His Asn Lys Ala Asp Tyr Ser Tyr Ser Gly Thr
    130                 135                 140

Pro
145
```

<210> SEQ ID NO 46
<211> LENGTH: 1332
<212> TYPE: DNA
<213> ORGANISM: Mus musculus

<400> SEQUENCE: 46

```
ttcccctggc tccagccggc gcaagcagcg gcggcggtgg cagcgggcga ggatctgcgg      60

ccccgcgagg ccatgaaggt gaagaaaggc ggcggcggga ccgggtcggg ggcggagccc     120

gttccagggg cctcgaaccg gagcgcggag cccacgcggg agcctggggc ggaagctgag     180

tccgggtccg agtcggagcc ggagccaggc ccggggccca ggctggggcc gctgcagggc     240

aagcagccca tcgggccgga ggatgtgctg ggctgcagc ggatcacggg tgactacctg     300

tgctcccctg aggaaaatat ctacaagatt gacttcgtca ggttcaagat ccgtgacatg     360

gactcaggga ctgtcctttt tgaaatcaag aagccccctg tttcggaacg gttgcccatc     420

aaccggcggg acctggaccc caatgcaggg cgctttgttc gctaccagtt cacacctgcc     480

ttcctccgcc taaggcaggt gggagccacg gtggagttca cagtgggaga caagccggtc     540

aacaacttcc gcatgatcga gaggcactac tttcgaaacc agctcctcaa aagcttcgac     600

ttccactttg gcttctgcat ccccagcagc aagaacacct gtgagcacat ctatgacttc     660

cctcctctct ccgaggagct aatcagtgag atgattcgtc acccgtatga gacccagtct     720

gacagcttct acttcgtgga tgaccggctg gtgatgcata acaaagcaga ctattcctac     780

agtgggacac cctgacccct aatgctgccc ctgaggctct ggcctagacc ctgtgctgta     840

acctctccga catcatctcc acttggggat ggatccggtg gctctggacc ctgagtcagt     900

ctcgagagga aaggtgtcca gcatccctag gcaaacctct ggagctagtg ggaggggcag     960

caggggggagg ctggctgtcc ccatgttcag gaaggcctcc tgcaagagga ggactcctgg    1020

atgcctcgct aggtccactg ggcctgagtt tcagagtagt gccccccttct tgaccgtgac    1080

tagatcaggt tagggaccat ttcctgtccc ttgcccacca cctccaggct atttatagtt    1140

gtcggttcac agacaaagat ccacagtggg taccctgctc tgagccctgg cctcctccat    1200

caggggccaa gaaactaccc gaggtgtgag aggggcgggt ccagatcgca gcctgtaaga    1260
```

```
cctggacaaa ctgtatatag ttttcaataa accttttctg ttcttgggtg cggccaaaaa   1320

aaaaaaaaaa aa                                                        1332


<210> SEQ ID NO 47
<211> LENGTH: 723
<212> TYPE: DNA
<213> ORGANISM: Mus musculus

<400> SEQUENCE: 47

atgaaggtga agaaaggcgg cggcgggacc gggtcggggg cggagcccgt tccaggggcc     60

tcgaaccgga gcgcggagcc cacgcgggag cctggggcgg aagctgagtc cgggtccgag    120

tcggagccgg agccaggccc ggggcccagg ctggggccgc tgcagggcaa gcagcccatc    180

gggccggagg atgtgctggg gctgcagcgg atcacgggtg actacctgtg ctcccctgag    240

gaaaatatct acaagattga cttcgtcagg ttcaagatcc gtgacatgga ctcagggact    300

gtcctttttg aaatcaagaa gccccctgtt tcggaacggt tgcccatcaa ccggcgggac    360

ctggacccca atgcagggcg ctttgttcgc taccagttca cacctgcctt cctccgccta    420

aggcaggtgg gagccacggt ggagttcaca gtgggagaca agccggtcaa caacttccgc    480

atgatcgaga ggcactactt tcgaaaccag ctcctcaaaa gcttcgactt ccactttggc    540

ttctgcatcc ccagcagcaa gaacacctgt gagcacatct atgacttccc tcctctctcc    600

gaggagctaa tcagtgagat gattcgtcac ccgtatgaga cccagtctga cagcttctac    660

ttcgtggatg accggctggt gatgcataac aaagcagact attcctacag tgggacaccc    720

tga                                                                  723


<210> SEQ ID NO 48
<211> LENGTH: 240
<212> TYPE: PRT
<213> ORGANISM: Mus musculus

<400> SEQUENCE: 48

Met Lys Val Lys Lys Gly Gly Gly Gly Thr Gly Ser Gly Ala Glu Pro
1               5                   10                  15

Val Pro Gly Ala Ser Asn Arg Ser Ala Glu Pro Thr Arg Glu Pro Gly
            20                  25                  30

Ala Glu Ala Glu Ser Gly Ser Glu Ser Glu Pro Glu Pro Gly Pro Gly
        35                  40                  45

Pro Arg Leu Gly Pro Leu Gln Gly Lys Gln Pro Ile Gly Pro Glu Asp
    50                  55                  60

Val Leu Gly Leu Gln Arg Ile Thr Gly Asp Tyr Leu Cys Ser Pro Glu
65                  70                  75                  80

Glu Asn Ile Tyr Lys Ile Asp Phe Val Arg Phe Lys Ile Arg Asp Met
                85                  90                  95

Asp Ser Gly Thr Val Leu Phe Glu Ile Lys Lys Pro Pro Val Ser Glu
            100                 105                 110

Arg Leu Pro Ile Asn Arg Arg Asp Leu Asp Pro Asn Ala Gly Arg Phe
        115                 120                 125

Val Arg Tyr Gln Phe Thr Pro Ala Phe Leu Arg Leu Arg Gln Val Gly
    130                 135                 140

Ala Thr Val Glu Phe Thr Val Gly Asp Lys Pro Val Asn Asn Phe Arg
145                 150                 155                 160

Met Ile Glu Arg His Tyr Phe Arg Asn Gln Leu Leu Lys Ser Phe Asp
                165                 170                 175
```

```
Phe His Phe Gly Phe Cys Ile Pro Ser Ser Lys Asn Thr Cys Glu His
            180                 185                 190

Ile Tyr Asp Phe Pro Pro Leu Ser Glu Glu Leu Ile Ser Glu Met Ile
        195                 200                 205

Arg His Pro Tyr Glu Thr Gln Ser Asp Ser Phe Tyr Phe Val Asp Asp
    210                 215                 220

Arg Leu Val Met His Asn Lys Ala Asp Tyr Ser Tyr Ser Gly Thr Pro
225                 230                 235                 240


<210> SEQ ID NO 49
<211> LENGTH: 1398
<212> TYPE: DNA
<213> ORGANISM: Homo sapiens

<400> SEQUENCE: 49

cccacttccc ccggctccag ccggcgcagg cagcggcggc agcagcaggc gagcctcggc     60

cccgcaaggc catgaaggtg aagaagggcg gcggtggggc cgggacggcg acggagtccg    120

ctccggggcc ctcgggccag agcgtggccc ccataccaca gccgcctgcg gaatccgaat    180

ctgggtccga gtcggagccg gacgcaggcc cagggcccag gccggggccg ctgcagagga    240

agcagccgat cgggccggag gacgtgctgg ggctgcagcg gatcaccggt gactacctct    300

gctcccctga ggagaatatc tacaagatcg actttgtcag gtttaagatt cgggacatgg    360

actcaggcac tgtcctcttt gaaatcaaga agcccccagt ctcagaacgg ttgcccatca    420

accggcggga cctggacccc aatgctgggc gctttgtccg ctaccagttc acgcctgcct    480

tcctccgcct gaggcaggtg ggagccacgg tggagttcac agtgggagac aagcctgtca    540

acaacttccg catgatcgag aggcactact tccgcaacca gctactcaaa agcttcgact    600

tccactttgg cttctgcatc cccagcagca agaacacctg cgagcacatt tacgacttcc    660

cccctctctc cgaggagctg atcagcgaga tgatccgcca cccgtatgag acccagtctg    720

acagcttcta cttcgtggat gaccggctgg tgatgcacaa taaagcagac tattcctaca    780

gcgggacacc ctgaccccac ggctgccctg accccaggag gctccagttc tgggctggga    840

gctgtgacct ccccaacgct cacccctcaa ccccaagtcc tctgcttggg gagttctcca    900

ggagctccgg accctgagtc aatgttggga ggaagggtac ctggtgtccc cagtcaagcc    960

catgaagccc atgcggcctg ctacatgggg tggggtcgta gggaggctgt ttgcctccac   1020

gtctaggaag gcctgtgaga ggagcagtca ggacttccgg acaacttagc tgggccctac   1080

ttgggcccaa gtttcagaat agtgttcccc tatcaaggct gtgactagat caggcaggga   1140

tccattccct gtcccctgcc cactaccttc aggccattta gagttgtaaa tttacaaaga   1200

tccacggtgg gctccagctg ccaagccacc caagggagtc tgggccctag gcctagcccc   1260

atccctcccc atgaggggcc aagacactgc ctaaggtgtg ggagggactg gctgagattg   1320

cagcccatgg taggagctgg accaactgta tatagttttc aataaacttt ttccttttct   1380

gttcaaaaaa aaaaaaaa                                                 1398


<210> SEQ ID NO 50
<211> LENGTH: 723
<212> TYPE: DNA
<213> ORGANISM: Homo sapiens

<400> SEQUENCE: 50

atgaaggtga agaagggcgg cggtggggcc gggacggcga cggagtccgc tccggggccc     60
```

```
tcgggccaga gcgtggcccc cataccacag ccgcctgcgg aatccgaatc tgggtccgag    120

tcggagccgg acgcaggccc agggcccagg ccggggccgc tgcagaggaa gcagccgatc    180

gggccggagg acgtgctggg gctgcagcgg atcaccggtg actacctctg ctcccctgag    240

gagaatatct acaagatcga ctttgtcagg tttaagattc gggacatgga ctcaggcact    300

gtcctctttg aaatcaagaa gcccccagtc tcagaacggt tgcccatcaa ccggcgggac    360

ctggacccca atgctgggcg ctttgtccgc taccagttca cgcctgcctt cctccgcctg    420

aggcaggtgg gagccacggt ggagttcaca gtgggagaca agcctgtcaa caacttccgc    480

atgatcgaga ggcactactt ccgcaaccag ctactcaaaa gcttcgactt ccactttggc    540

ttctgcatcc ccagcagcaa gaacacctgc gagcacattt acgacttccc ccctctctcc    600

gaggagctga tcagcgagat gatccgccac ccgtatgaga cccagtctga cagcttctac    660

ttcgtggatg accggctggt gatgcacaat aaagcagact attcctacag cgggacaccc    720

tga                                                                  723
```

<210> SEQ ID NO 51
<211> LENGTH: 240
<212> TYPE: PRT
<213> ORGANISM: Homo sapiens

<400> SEQUENCE: 51

```
Met Lys Val Lys Lys Gly Gly Gly Gly Ala Gly Thr Ala Thr Glu Ser
1               5                   10                  15

Ala Pro Gly Pro Ser Gly Gln Ser Val Ala Pro Ile Pro Gln Pro Pro
            20                  25                  30

Ala Glu Ser Glu Ser Gly Ser Glu Ser Glu Pro Asp Ala Gly Pro Gly
        35                  40                  45

Pro Arg Pro Gly Pro Leu Gln Arg Lys Gln Pro Ile Gly Pro Glu Asp
    50                  55                  60

Val Leu Gly Leu Gln Arg Ile Thr Gly Asp Tyr Leu Cys Ser Pro Glu
65                  70                  75                  80

Glu Asn Ile Tyr Lys Ile Asp Phe Val Arg Phe Lys Ile Arg Asp Met
                85                  90                  95

Asp Ser Gly Thr Val Leu Phe Glu Ile Lys Lys Pro Pro Val Ser Glu
            100                 105                 110

Arg Leu Pro Ile Asn Arg Arg Asp Leu Asp Pro Asn Ala Gly Arg Phe
        115                 120                 125

Val Arg Tyr Gln Phe Thr Pro Ala Phe Leu Arg Leu Arg Gln Val Gly
    130                 135                 140

Ala Thr Val Glu Phe Thr Val Gly Asp Lys Pro Val Asn Asn Phe Arg
145                 150                 155                 160

Met Ile Glu Arg His Tyr Phe Arg Asn Gln Leu Leu Lys Ser Phe Asp
                165                 170                 175

Phe His Phe Gly Phe Cys Ile Pro Ser Ser Lys Asn Thr Cys Glu His
            180                 185                 190

Ile Tyr Asp Phe Pro Pro Leu Ser Glu Glu Leu Ile Ser Glu Met Ile
        195                 200                 205

Arg His Pro Tyr Glu Thr Gln Ser Asp Ser Phe Tyr Phe Val Asp Asp
    210                 215                 220

Arg Leu Val Met His Asn Lys Ala Asp Tyr Ser Tyr Ser Gly Thr Pro
225                 230                 235                 240
```

<210> SEQ ID NO 52

<211> LENGTH: 1665
<212> TYPE: DNA
<213> ORGANISM: Homo sapiens

<400> SEQUENCE: 52

```
cccacttccc ccggctccag ccggcgcagg cagcggcggc agcagcaggc gagcctcggc     60
cccgcaaggc catgaaggtg aagaagggcg gcggtggggc cgggacggcg acggagtccg    120
ctccggggcc ctcgggccag agcgtggccc ccataccaca gccgcctgcg gaatccgaat    180
ctgggtccga gtcggagccg gacgcaggcc cagggcccag gccggggccg ctgcagagga    240
agcagccgat cgggccggag gacgtgctgg ggctgcagcg gatcaccggt gactacctct    300
gctcccctga ggagaatatc tacaagatcg actttgtcag gtttaagatt cgggacatgg    360
actcaggcac tgtcctcttt gaaatcaaga agcccccagt ctcagaacgg ttgcccatca    420
accggcggga cctggacccc aatgctgggc gctttgtccg ctaccagttc acgcctgcct    480
tcctccgcct gaggcaggtg ggagccacgg tggagttcac agtgggagac aagcctgtca    540
acaacttccg catgatcgag aggcactact tccgcaacca gctactcaaa agcttcgact    600
tccactttgg cttctgcatc cccagcagca agaacacctg cgagcacatt tacgacttcc    660
cccctctctc cgaggagctg agtgcgcggg cagggtcttc tgggagtggg gaagtggggg    720
cgtctagaga ctgagctgcg ggagggagag ggacttgtgg gtctgatccc atttctcccc    780
accctggggc tcttctgtgt ctgccaccat tcccatatca tccgtagaga aagaggctgg    840
ggatatttca ggctgtttgg ctgtccctgt accccagtcc tgaagcccct gcagtggcgg    900
gactcaagct cctgaccttt gcccggcctg gctgggcctc tcttgcagtc agcgagatga    960
tccgccaccc gtatgagacc cagtctgaca gcttctactt cgtggatgac cggctggtga   1020
tgcacaataa agcagactat tcctacagcg ggacaccctg accccacggc tgccctgacc   1080
ccaggaggct ccagttctgg gctgggagct gtgacctccc caacgctcac ccctcaaccc   1140
caagtcctct gcttggggag ttctccagga gctccggacc ctgagtcaat gttgggagga   1200
agggtacctg gtgtccccag tcaagcccat gaagcccatg cggcctgcta catggggtgg   1260
ggtcgtaggg aggctgtttg cctccacgtc taggaaggcc tgtgagagga gcagtcagga   1320
cttccggaca acttagctgg gccctacttg ggcccaagtt tcagaatagt gttcccctat   1380
caaggctgtg actagatcag gcagggatcc attccctgtc ccctgcccac taccttcagg   1440
ccatttagag ttgtaaattt acaaagatcc acggtgggct ccagctgcca agccacccaa   1500
gggagtctgg gccctaggcc tagccccatc cctccccatg aggggccaag acactgccta   1560
aggtgtggga gggactggct gagattgcag cccatggtag gagctggacc aactgtatat   1620
agttttcaat aaactttttc cttttctgtt caaaaaaaaa aaaaa                   1665
```

<210> SEQ ID NO 53
<211> LENGTH: 663
<212> TYPE: DNA
<213> ORGANISM: Homo sapiens

<400> SEQUENCE: 53

```
atgaaggtga agaagggcgg cggtggggcc gggacggcga cggagtccgc tccggggccc     60
tcgggccaga gcgtggcccc cataccacag ccgcctgcgg aatccgaatc tgggtccgag    120
tcggagccgg acgcaggccc agggcccagg ccggggccgc tgcagaggaa gcagccgatc    180
gggccggagg acgtgctggg gctgcagcgg atcaccggtg actacctctg ctcccctgag    240
gagaatatct acaagatcga ctttgtcagg tttaagattc gggacatgga ctcaggcact    300
```

```
gtcctctttg aaatcaagaa gcccccagtc tcagaacggt tgcccatcaa ccggcgggac    360

ctggacccca atgctgggcg ctttgtccgc taccagttca cgcctgcctt cctccgcctg    420

aggcaggtgg gagccacggt ggagttcaca gtgggagaca agcctgtcaa caacttccgc    480

atgatcgaga ggcactactt ccgcaaccag ctactcaaaa gcttcgactt ccactttggc    540

ttctgcatcc ccagcagcaa gaacacctgc gagcacattt acgacttccc ccctctctcc    600

gaggagctga gtgcgcgggc agggtcttct gggagtgggg aagtgggggc gtctagagac    660

tga                                                                  663


<210> SEQ ID NO 54
<211> LENGTH: 220
<212> TYPE: PRT
<213> ORGANISM: Homo sapiens

<400> SEQUENCE: 54

Met Lys Val Lys Lys Gly Gly Gly Gly Ala Gly Thr Ala Thr Glu Ser
1               5                   10                  15

Ala Pro Gly Pro Ser Gly Gln Ser Val Ala Pro Ile Pro Gln Pro Pro
            20                  25                  30

Ala Glu Ser Glu Ser Gly Ser Glu Ser Glu Pro Asp Ala Gly Pro Gly
        35                  40                  45

Pro Arg Pro Gly Pro Leu Gln Arg Lys Gln Pro Ile Gly Pro Glu Asp
    50                  55                  60

Val Leu Gly Leu Gln Arg Ile Thr Gly Asp Tyr Leu Cys Ser Pro Glu
65                  70                  75                  80

Glu Asn Ile Tyr Lys Ile Asp Phe Val Arg Phe Lys Ile Arg Asp Met
                85                  90                  95

Asp Ser Gly Thr Val Leu Phe Glu Ile Lys Lys Pro Pro Val Ser Glu
            100                 105                 110

Arg Leu Pro Ile Asn Arg Arg Asp Leu Asp Pro Asn Ala Gly Arg Phe
        115                 120                 125

Val Arg Tyr Gln Phe Thr Pro Ala Phe Leu Arg Leu Arg Gln Val Gly
    130                 135                 140

Ala Thr Val Glu Phe Thr Val Gly Asp Lys Pro Val Asn Asn Phe Arg
145                 150                 155                 160

Met Ile Glu Arg His Tyr Phe Arg Asn Gln Leu Leu Lys Ser Phe Asp
                165                 170                 175

Phe His Phe Gly Phe Cys Ile Pro Ser Ser Lys Asn Thr Cys Glu His
            180                 185                 190

Ile Tyr Asp Phe Pro Pro Leu Ser Glu Glu Leu Ser Ala Arg Ala Gly
        195                 200                 205

Ser Ser Gly Ser Gly Glu Val Gly Ala Ser Arg Asp
    210                 215                 220


<210> SEQ ID NO 55
<211> LENGTH: 1461
<212> TYPE: DNA
<213> ORGANISM: Homo sapiens

<400> SEQUENCE: 55

ctggggcccc ggccgggggc ggggctgcgg atgctcccac ttcccccggc tccagccggc     60

gcaggcagcg gcggcagcag caggcgagcc tcggccccgc aaggccatga aggtgaagaa    120

gggcggcggt ggggccggga cggcgacgga gtccgctccg gggccctcgg gccagagcgt    180
```

```
ggcccccata ccacagccgc ctgcggaatc cgaatctggg tccgagtcgg agccggacgc    240

aggcccaggg cccaggccgg ggccgctgca gaggaagcag ccgatcgggc cggaggacgt    300

gctggggctg cagcggatca ccggtggggc ccgtcccctt ttcccagcgt ggagactacc    360

tctgctcccc tgaggagaat atctacaaga tcgactttgt caggtttaag attcgggaca    420

tggactcagg cactgtcctc tttgaaatca agaagccccc agtctcagaa cggttgccca    480

tcaaccggcg ggacctggac cccaatgctg ggcgctttgt ccgctaccag ttcacgcctg    540

ccttcctccg cctgaggcag gtgggagcca cggtggagtt cacagtggga gacaagcctg    600

tcaacaactt ccgcatgatc gagaggcact acttccgcaa ccagctactc aaaagcttcg    660

acttccactt tggcttctgc atccccagca gcaagaacac ctgcgagcac atttacgact    720

tcccccctct ctccgaggag ctgatcagcg agatgatccg ccacccgtat gagacccagt    780

ctgacagctt ctacttcgtg gatgaccggc tggtgatgca caataaagca gactattcct    840

acagcgggac accctgaccc cacggctgcc ctgaccccag gaggctccag ttctgggctg    900

ggagctgtga cctccccaac gctcacccct caaccccaag tcctctgctt ggggagttct    960

ccaggagctc cggaccctga gtcaatgttg ggaggaaggg tacctggtgt ccccagtcaa   1020

gcccatgaag cccatgcggc ctgctacatg ggtggggtc gtagggaggc tgtttgcctc   1080

cacgtctagg aaggcctgtg agaggagcag tcaggacttc cggacaactt agctgggccc   1140

tacttgggcc caagtttcag aatagtgttc ccctatcaag gctgtgacta gatcaggcag   1200

ggatccattc cctgtcccct gcccactacc ttcaggccat ttagagttgt aaatttacaa   1260

agatccacgg tgggctccag ctgccaagcc acccaaggga gtctgggccc taggcctagc   1320

cccatccctc cccatgaggg gccaagacac tgcctaaggt gtgggaggga ctggctgaga   1380

ttgcagccca tggtaggagc tggaccaact gtatatagtt ttcaataaac tttttccttt   1440

tctgttcaaa aaaaaaaaaa a                                             1461
```

<210> SEQ ID NO 56
<211> LENGTH: 438
<212> TYPE: DNA
<213> ORGANISM: Homo sapiens

<400> SEQUENCE: 56

```
atggactcag gcactgtcct ctttgaaatc aagaagcccc cagtctcaga acggttgccc     60

atcaaccggc gggacctgga ccccaatgct gggcgctttg tccgctacca gttcacgcct    120

gccttcctcc gcctgaggca ggtgggagcc acggtggagt tcacagtggg agacaagcct    180

gtcaacaact tccgcatgat cgagaggcac tacttccgca accagctact caaaagcttc    240

gacttccact ttggcttctg catccccagc agcaagaaca cctgcgagca catttacgac    300

ttcccccctc tctccgagga gctgatcagc gagatgatcc gccacccgta tgagacccag    360

tctgacagct tctacttcgt ggatgaccgg ctggtgatgc acaataaagc agactattcc    420

tacagcggga caccctga                                                  438
```

<210> SEQ ID NO 57
<211> LENGTH: 145
<212> TYPE: PRT
<213> ORGANISM: Homo sapiens

<400> SEQUENCE: 57

```
Met Asp Ser Gly Thr Val Leu Phe Glu Ile Lys Lys Pro Pro Val Ser
1               5                   10                  15
```

```
Glu Arg Leu Pro Ile Asn Arg Arg Asp Leu Asp Pro Asn Ala Gly Arg
            20                  25                  30

Phe Val Arg Tyr Gln Phe Thr Pro Ala Phe Leu Arg Leu Arg Gln Val
        35                  40                  45

Gly Ala Thr Val Glu Phe Thr Val Gly Asp Lys Pro Val Asn Asn Phe
    50                  55                  60

Arg Met Ile Glu Arg His Tyr Phe Arg Asn Gln Leu Leu Lys Ser Phe
65                  70                  75                  80

Asp Phe His Phe Gly Phe Cys Ile Pro Ser Ser Lys Asn Thr Cys Glu
                85                  90                  95

His Ile Tyr Asp Phe Pro Pro Leu Ser Glu Glu Leu Ile Ser Glu Met
            100                 105                 110

Ile Arg His Pro Tyr Glu Thr Gln Ser Asp Ser Phe Tyr Phe Val Asp
        115                 120                 125

Asp Arg Leu Val Met His Asn Lys Ala Asp Tyr Ser Tyr Ser Gly Thr
    130                 135                 140

Pro
145
```

<210> SEQ ID NO 58
<211> LENGTH: 24
<212> TYPE: DNA
<213> ORGANISM: Artificial
<220> FEATURE:
<223> OTHER INFORMATION: Primer

<400> SEQUENCE: 58
aggactatca tctgatgcca gagc 24

<210> SEQ ID NO 59
<211> LENGTH: 23
<212> TYPE: DNA
<213> ORGANISM: Artificial
<220> FEATURE:
<223> OTHER INFORMATION: Primer

<400> SEQUENCE: 59
tctgccacaa gctgtacatc tca 23

<210> SEQ ID NO 60
<211> LENGTH: 27
<212> TYPE: DNA
<213> ORGANISM: Artificial
<220> FEATURE:
<223> OTHER INFORMATION: Primer

<400> SEQUENCE: 60
agggagtttc taacaatgct gggaaca 27

<210> SEQ ID NO 61
<211> LENGTH: 27
<212> TYPE: DNA
<213> ORGANISM: Artificial
<220> FEATURE:
<223> OTHER INFORMATION: Primer

<400> SEQUENCE: 61
ctgctcctct gacttcacat tcagctc 27

<210> SEQ ID NO 62
<211> LENGTH: 27
<212> TYPE: DNA

<213> ORGANISM: Artificial
<220> FEATURE:
<223> OTHER INFORMATION: Primer

<400> SEQUENCE: 62
aggctcagga gttcgaggtg acatgaa 27

<210> SEQ ID NO 63
<211> LENGTH: 27
<212> TYPE: DNA
<213> ORGANISM: Artificial
<220> FEATURE:
<223> OTHER INFORMATION: Primer

<400> SEQUENCE: 63
ggaggaccag cctcctttct acttgat 27

<210> SEQ ID NO 64
<211> LENGTH: 21
<212> TYPE: DNA
<213> ORGANISM: Artificial
<220> FEATURE:
<223> OTHER INFORMATION: Primer

<400> SEQUENCE: 64
cgtgcgtgac atcaaagaga a 21

<210> SEQ ID NO 65
<211> LENGTH: 20
<212> TYPE: DNA
<213> ORGANISM: Artificial
<220> FEATURE:
<223> OTHER INFORMATION: Primer

<400> SEQUENCE: 65
tggatgccac aggattccat 20

<210> SEQ ID NO 66
<211> LENGTH: 35
<212> TYPE: DNA
<213> ORGANISM: Artificial
<220> FEATURE:
<223> OTHER INFORMATION: Primer

<400> SEQUENCE: 66
aaaatcgata tggtggagga cggcgcggag gagct 35

<210> SEQ ID NO 67
<211> LENGTH: 35
<212> TYPE: DNA
<213> ORGANISM: Artificial
<220> FEATURE:
<223> OTHER INFORMATION: Primer

<400> SEQUENCE: 67
aaagcggccg cgaagcgcct atgcttgtac cagat 35

<210> SEQ ID NO 68
<211> LENGTH: 28
<212> TYPE: DNA
<213> ORGANISM: Artificial
<220> FEATURE:
<223> OTHER INFORMATION: Primer

<400> SEQUENCE: 68
tcccgggatg agctgaatgt gaagtcag 28

<210> SEQ ID NO 69
<211> LENGTH: 31
<212> TYPE: DNA
<213> ORGANISM: Artificial
<220> FEATURE:
<223> OTHER INFORMATION: Primer

<400> SEQUENCE: 69
tgtcgactta gatggtgaga agagggatgc a 31

<210> SEQ ID NO 70
<211> LENGTH: 38
<212> TYPE: DNA
<213> ORGANISM: Artificial
<220> FEATURE:
<223> OTHER INFORMATION: Primer

<400> SEQUENCE: 70
gggctcgaga tgaaggtgaa gaaaggcggc ggcgggac 38

<210> SEQ ID NO 71
<211> LENGTH: 38
<212> TYPE: DNA
<213> ORGANISM: Artificial
<220> FEATURE:
<223> OTHER INFORMATION: Primer

<400> SEQUENCE: 71
ggggcggccg ctcagggtgt cccactgtag gaatagtc 38

<210> SEQ ID NO 72
<211> LENGTH: 36
<212> TYPE: DNA
<213> ORGANISM: Artificial
<220> FEATURE:
<223> OTHER INFORMATION: Primer

<400> SEQUENCE: 72
gggctcgaga tgcagatctt cgtgaagacc ctgacc 36

<210> SEQ ID NO 73
<211> LENGTH: 41
<212> TYPE: DNA
<213> ORGANISM: Artificial
<220> FEATURE:
<223> OTHER INFORMATION: Primer

<400> SEQUENCE: 73
ggggcggccg cttagccacc tctcaggcga aggaccaggt g 41

<210> SEQ ID NO 74
<211> LENGTH: 38
<212> TYPE: DNA
<213> ORGANISM: Artificial
<220> FEATURE:
<223> OTHER INFORMATION: Primer

<400> SEQUENCE: 74
gggctcgaga tcccgggatg agctgaatgt gaagtcag 38

<210> SEQ ID NO 75
<211> LENGTH: 33
<212> TYPE: DNA
<213> ORGANISM: Artificial
<220> FEATURE:

<223> OTHER INFORMATION: Primer

<400> SEQUENCE: 75
tgtcgactta gatggtgaga agagggatgc agc 33

<210> SEQ ID NO 76
<211> LENGTH: 37
<212> TYPE: DNA
<213> ORGANISM: Artificial
<220> FEATURE:
<223> OTHER INFORMATION: Primer

<400> SEQUENCE: 76
gaattcgcca ccatggtgga ggacggcgcg gaggagc 37

<210> SEQ ID NO 77
<211> LENGTH: 22
<212> TYPE: DNA
<213> ORGANISM: Artificial
<220> FEATURE:
<223> OTHER INFORMATION: Primer

<400> SEQUENCE: 77
ctttgatgct ctgcagctgc ag 22

<210> SEQ ID NO 78
<211> LENGTH: 35
<212> TYPE: DNA
<213> ORGANISM: Artificial
<220> FEATURE:
<223> OTHER INFORMATION: Primer

<400> SEQUENCE: 78
gggaattcat ggtggaggac ggcgcggagg agctg 35

<210> SEQ ID NO 79
<211> LENGTH: 34
<212> TYPE: DNA
<213> ORGANISM: Artificial
<220> FEATURE:
<223> OTHER INFORMATION: Primer

<400> SEQUENCE: 79
ggctcgagga aagctggcag gtggggccgg cgct 34

<210> SEQ ID NO 80
<211> LENGTH: 35
<212> TYPE: DNA
<213> ORGANISM: Artificial
<220> FEATURE:
<223> OTHER INFORMATION: Primer

<400> SEQUENCE: 80
tgaattcatg aaggtgaaga aaggcggcgg cggga 35

<210> SEQ ID NO 81
<211> LENGTH: 34
<212> TYPE: DNA
<213> ORGANISM: Artificial
<220> FEATURE:
<223> OTHER INFORMATION: Primer

<400> SEQUENCE: 81
tgtcgactca gggtgtccca ctgtaggaat agtc 34

-continued

```
<210> SEQ ID NO 82
<211> LENGTH: 25
<212> TYPE: DNA
<213> ORGANISM: Artificial
<220> FEATURE:
<223> OTHER INFORMATION: Primer

<400> SEQUENCE: 82

caccgagttt cttgtagcca ccagc                                            25


<210> SEQ ID NO 83
<211> LENGTH: 25
<212> TYPE: DNA
<213> ORGANISM: Artificial
<220> FEATURE:
<223> OTHER INFORMATION: Primer

<400> SEQUENCE: 83

aaacgctggt ggctacaaga aactc                                            25


<210> SEQ ID NO 84
<211> LENGTH: 25
<212> TYPE: DNA
<213> ORGANISM: Artificial
<220> FEATURE:
<223> OTHER INFORMATION: Primer

<400> SEQUENCE: 84

caccgactgg cagtctcctc cgatg                                            25


<210> SEQ ID NO 85
<211> LENGTH: 25
<212> TYPE: DNA
<213> ORGANISM: Artificial
<220> FEATURE:
<223> OTHER INFORMATION: Primer

<400> SEQUENCE: 85

aaaccatcgg aggagactgc cagtc                                            25
```

AGENT FOR INHIBITING OR REDUCING LIGHT SENSITIVITY

CROSS REFERENCE TO RELATED APPLICATIONS

This application is a U.S. National Phase Application of PCT International Application Number PCT/JP2018/010660, filed on Mar. 16, 2018, designating the United States of America and published in the Japanese language, which is an International Application of and claims the benefit of priority to Japanese Patent Application No. 2017-053811, filed on Mar. 17, 2017, and Japanese Patent Application No. 2017-248490, filed on Dec. 25, 2017. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is SeqList-IWAT007-007APC.txt, the date of creation of the ASCII text file is Aug. 22, 2019, and the size of the ASCII text file is 174 KB.

TECHNICAL FIELD

The present invention relates to an agent for inhibiting or reducing light sensitivity, the agent comprising a substance that inhibits or reduces ubiquitination.

BACKGROUND ART

We obtain about 90% of information from the external world using the visual sense. Visual impairment will significantly deteriorates the quality of life (QOL), substantially restricts social activities such as daily life, mobility, communication, etc., which shortens healthy life expectancy of the visually impaired and also imposes a heavy burden on the caregivers. Visual impairment in the elderly may increase the risk of dementia, depression and other diseases. In these circumstances, there is an urgent need to provide method for treating or preventing retinal diseases that may lead to blindness, and to develop therapy for prevention and cure of visual impairment related to aging.

Our vision begins with light reception and conversion to electrical signals by photoreceptor cells. The signals are finally transmitted to the brain to be translated into visual information. Paradoxically, long-term light exposure gradually aggravates the accumulation of metabolic waste and cell stress, and induces the aging and cell death of photoreceptor cells and the retinal pigment epithelium, which may lead to visual disorders including age-related macular degeneration and retinitis pigmentosa.

Age-related macular degeneration is an ocular disease associated with symptoms such as blurred or distorted vision in the center of the vision field. In advanced countries, this disease is the most common causes of blindness in the elderly. Retinitis pigmentosa is a progressive disease that causes partial or total loss of vision and/or night blindness due to degeneration and/or loss of photoreceptor cells, which eventually lead to blindness.

These diseases are currently treated with gene therapy, neuroprotective therapy and regenerative therapy, but there is no truly effective therapy and prevention.

Ubiquitin is a protein of 76 amino acids found in eukaryotes, and whose sequence is evolutionally conserved.

Ubiquitin is covalently attached to a target protein followed by chain elongation by a ubiquitinating enzyme to act as degradation signals. The ubiquitinated target protein is then degraded by a proteasome that recognizes ubiquitin.

SUMMARY OF INVENTION

Technical Problem

An object of the present invention is to provide an agent for inhibiting or reducing light sensitivity.

Another object of the present invention is to provide an agent for enhancing or maintaining light sensitivity.

Solution to Problem

Ubiquitinating enzymes as described above have been identified in the retina, but their functions are not clear.

Under these circumstances, the inventors have surprisingly found that ubiquitination in the retina is related to the light sensitivity of the retina. Based on this finding, the inventor conducted further investigations, and found that deletion of the gene encoding the ubiquitinating enzyme Klhl18 expressed in the retina or inhibition of its function leads to the attenuation of rod photoreceptor response to light and the reduction in the light sensitivity of the retina. The inventors conducted further studies, revealed various findings and completed the present invention.

That is, the present invention relates to the following.

(1) An agent for inhibiting or reducing light sensitivity, the agent comprising a substance that inhibits or reduces ubiquitination.

(2) The agent according to the above (1), which protects a retina, inhibits retinal degeneration, reduces aging of a retina and/or reduces hyperesthesia.

(3) The agent according to the above (1) or (2), which ameliorates or prevents a symptom associated with light reception.

(4) The agent according to the above (3), wherein the symptom associated with light reception is at least one selected from the group consisting of age-related macular degeneration, retinitis pigmentosa, Leber congenital amaurosis, Stargardt disease, cone-rod dystrophy, diabetic retinopathy, macular edema, retinal ischemia, photosensitive seizure, photosensitive epilepsy, psychiatric disorders, photic maculopathy, asthenopia, retinal dysfunction, sleep disorders, migraine and light-induced damage.

(5) The agent according to any one of the above (1) to (4), wherein the substance that inhibits or reduces ubiquitination comprises a substance that inhibits or reduces a ubiquitinating enzyme and/or a substance that inhibits or reduces ubiquitination.

(6) The agent according to the above (5), wherein the ubiquitinating enzyme has an ability to modulate or regulate light sensitivity.

(7) The agent according to the above (5) or (6), wherein the ubiquitinating enzyme is a protein selected from the following (A) and (B):

(A) a protein consisting of the amino acid sequence of any of SEQ ID NOs: 3, 6, 9, 12, 15, 18, 21, 24, 27, 30 and 33; and (B) a protein consisting of the amino acid sequence of any of SEQ ID NOs: 3, 6, 9, 12, 15, 18, 21, 24, 27, 30 and 33 that have substitution, deletion, insertion and/or addition of one or more amino acids.

(8) The agent according to any one of the above (5) to (7), wherein the substance that inhibits or reduces a ubiquitinating enzyme is at least one selected from an inhibitor of binding of a ubiquitinating enzyme, part of a ubiquitinating enzyme protein, a proteasome inhibitor, an antibody, a siRNA, a shRNA, a dsRNA, a microRNA, an antisense polynucleotide, an aptamer, a gene-targeting substance, and a substance that inhibits an activity of a ubiquitination complex protein.

(9) The agent according to any one of the above (5) to (8), wherein the substance that inhibits or reduces ubiquitination is at least one selected from a full-length or part of a target protein of a ubiquitinating enzyme or a substance that induces or promotes the expression of a gene encoding a target protein of a ubiquitinating enzyme.

(10) A composition for inhibiting or reducing light sensitivity (or for ameliorating or preventing a symptom associated with light reception), the composition comprising the agent according to any one of the above (1) to (9).

(11) The composition according to the above (10), which is a composition for injection or administration as an eye drop.

(12) The composition according to the above (10), which is a food composition.

(13) A substance that inhibits or reduces ubiquitination.

(14) The substance according to the above (13), which is at least one selected from an inhibitor of binding of a ubiquitinating enzyme, part of a ubiquitinating enzyme protein, an antibody, a siRNA, a shRNA, a dsRNA, a microRNA, an antisense polynucleotide, an aptamer, a gene-targeting substance, a substance that inhibits an activity of a ubiquitination complex protein, a full-length or part of a target protein of a ubiquitinating enzyme, and a substance that induces or promotes the expression of a gene encoding a target protein of a ubiquitinating enzyme.

(15) A substance that inhibits or reduces ubiquitination for use in production of the agent or the composition according to any one of the above (1) to (12).

(16) A method for inhibiting or reducing ubiquitination in an animal and thereby inhibiting or reducing light sensitivity (or ameliorating or preventing a symptom associated with light reception).

(17) The method according to the above (16), which comprises administering the agent or the composition according to any one of the above (1) to (12) to the animal.

(18) An agent for enhancing or maintaining light sensitivity, the agent comprising at least one selected from a ubiquitinating enzyme, a gene encoding a ubiquitinating enzyme, and a substance having an ability to induce or promote the expression of a ubiquitinating enzyme.

(19) A method for screening for an agent for ameliorating or preventing a symptom associated with light reception, the method comprising:

adding a test substance to cells into which a gene encoding a ubiquitinating enzyme and a gene encoding a target protein have been introduced, and determining that the test substance has an effect of ameliorating or preventing a symptom associated with light reception when the amount of ubiquitin conjugated to the target protein in the cells is reduced as compared with that in cells with no addition of the test substance.

(20) A method for screening for an agent for ameliorating or preventing a symptom associated with light reception, the method comprising:

adding a test substance to cells into which a gene encoding a ubiquitinating enzyme has been introduced, and determining that the test substance has an effect of ameliorating or preventing a symptom associated with light reception when the expression level of a target protein in the cells is increased as compared with that in cells with no addition of the test substance.

(21) A method for screening for an agent for ameliorating or preventing a symptom associated with light reception, the method comprising:

adding a test substance to measure an interaction between a ubiquitinating enzyme and a target protein or an interaction between a ubiquitinating enzyme and a protein component of a ubiquitin ligase complex, and determining that the test substance has an effect of ameliorating or preventing a symptom associated with light reception when the interaction between the ubiquitinating enzyme and the target protein or the interaction between the ubiquitinating enzyme and the protein component of a ubiquitin ligase complex is reduced as compared with that with no addition of the test substance.

Advantageous Effects of Invention

The present invention provides an agent for inhibiting or reducing light sensitivity.

The present invention also provides an agent for enhancing or maintaining light sensitivity.

BRIEF DESCRIPTION OF DRAWINGS

FIG. 14 shows the immunoprecipitation analysis of the interaction between HA-Unc119 protein and full-length Flag-Klhl18 protein or the N-terminal domain of Flag-Klhl18 protein or the C-terminal domain of Flag-Klhl18 protein.

FIG. 15 shows the Western blot analysis of the inhibitory effect of MLN4924 (an inhibitor of Nedd8-activating enzyme) on Klhl18 protein.

FIG. 16 is a schematic view of an inserted gene in the pCAGIG plasmid and the pCAGIG-N-3× FLAG-Unc119 plasmid.

DESCRIPTION OF EMBODIMENTS

Agent

Figure 1:
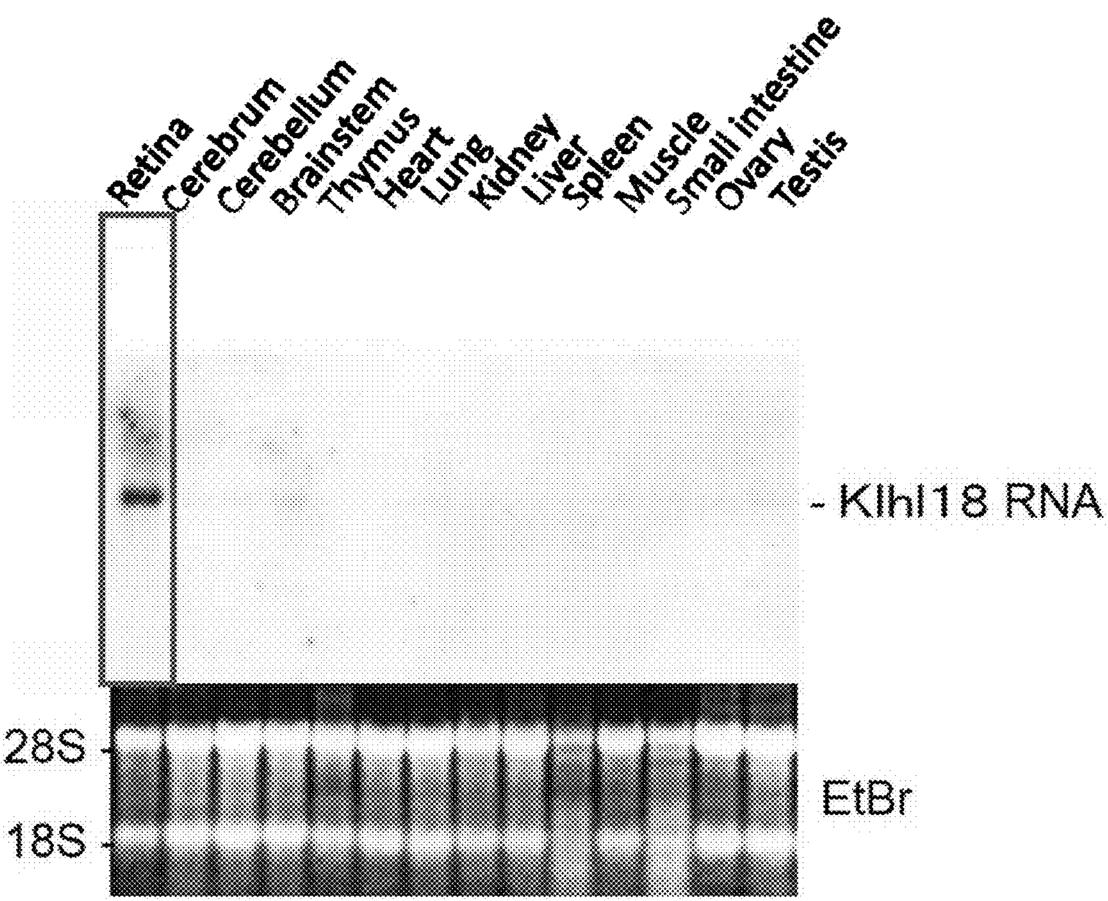
FIG. 1 shows the Northern blot analysis of the retinal region with expression of the retinal ubiquitinating enzyme Klhl18 in mice. EtBr: ethidium bromide, 28S: 28S ribosomal RNA, 18S: 18S ribosomal RNA.

The agent of the present invention can be used to inhibit or reduce light sensitivity. The agent of the present invention comprises a substance that inhibits or reduces ubiquitination (ubiquitination in the retina) (this substance may be called the substance (A) etc. below). That is, ubiquitination in the retina is related to light sensitivity, and thus inhibition or reduction of ubiquitination leads to inhibition or reduction of light sensitivity, thereby ameliorating or preventing a symptom associated with light reception.

The term “symptom” as used herein includes diseases and the like.

The term “amelioration” as used herein includes treatment and the like. The degree of amelioration is not limited to a particular one, and the amelioration also includes remission of a symptom, complete cure of a symptom, and the like. The degree of the “prevention” is also not limited, and the prevention includes the prevention of the onset or progression of a symptom and/or a disease.

The substance (A) may be any substance that inhibits or reduces ubiquitination, and its mechanism of inhibition or reduction of ubiquitination is not limited to a particular one. For example, the substance (A) may be a substance that inhibits or reduces ubiquitination, or a substance that inhibits or reduces an enzyme involved in ubiquitination (a ubiquitinating enzyme), or a substance that inhibits or reduces the interaction of enzymes involved in ubiquitination, or a substance that has any of the above functions.

The substance (A) may be a single type or a combination of two or more types.

The substance (A) is typically a substance that inhibits or reduces a ubiquitinating enzyme or a substance that inhibits or reduces ubiquitination. Therefore, the substance (A) may include at least either of a substance that inhibits or reduces a ubiquitinating enzyme or a substance that inhibits or reduces ubiquitination.

The present invention including ubiquitinating enzymes will be described in detail below.

Ubiquitinating Enzyme

The ubiquitinating enzyme in the present invention may be, for example, a ubiquitinating enzyme that functions in the retina and mediates the binding of ubiquitin to a target. Preferred is a ubiquitinating enzyme expressed in the retina. The ubiquitinating enzyme preferably has the ability to modulate or regulate light sensitivity of the retina, and is preferably capable of ubiquitinating proteins involved in retinal light sensitivity. More preferably, the ubiquitinating enzyme is an enzyme capable of ubiquitinating proteins involved in the modulation or regulation of light sensitivity of the retina.

The ubiquitinating enzyme protein may be a ubiquitinating enzyme protein of SEQ ID NO: 3 or 12, or an isoform thereof. The isoform of the ubiquitinating enzyme protein include those of SEQ ID NOs: 6, 9, 15, 18, 21, 24, 27, 30 and 33.

The ubiquitinating enzyme protein also includes those containing substitution, deletion, insertion and/or addition of amino acids and having ubiquitination activity. The number of amino acids substituted, deleted, inserted and/or added is not limited, and may be one or more, for example, 20 or less, 15 or less, 10 or less, 7 or less, 5 or less, 3 or less, 1 or 2, 1, etc.

The ubiquitinating enzyme in the present invention may be from any organism, but is preferably from, for example, primates, pets, or rodents, is more preferably from primates or pets, and is further preferably from humans.

A target of ubiquitination may be, for example, a protein of SEQ ID NO: 36 or 51 or an isoform thereof. The isoform may be a protein consisting of the amino acid sequence of SEQ ID NO: 39, 42, 45, 48, 54, 57, or the like, or a protein encoded by the nucleotide sequence of SEQ ID NO: 34, 35, 37, 38, 40, 41, 43, 44, 46, 47, 49, 50, 52, 53, 55, 56, or the like.

The nucleotide sequences of SEQ ID NOs: 35, 38, 41, 44, 47, 50, 53 and 56 corresponds to positions 73 to 861, positions 26 to 619, positions 26 to 553, positions 165 to 602, positions 73 to 795, positions 72 to 794, positions 72 to 734, or positions 420 to 857 of the nucleotide sequence encoding the Unc119 gene, respectively (the Unc119 gene is encoded by SEQ ID NO: 34, 37, 40, 43, 46, 49, 52 or 55).

Specific examples of the ubiquitinating enzyme include Klhl18 etc. Klhl18 is reported to be involved in ubiquitination of a target protein by *Drosophila* Cullin 3-based E3 ubiquitin ligase (Sally Fujiyama-Nakamura et al., Genes to Cells, 2009, 14, 965-973). Klhl18 is also reported to form a complex with Cullin 3 protein and promote the ubiquitination of Aurora-A protein, and Klhl18 is involved in mitotic entry (Saili Moghe et al., Biol. Open., 2012, 1(2), 82-91).

Klhl18 (Kelch-like 18) is composed of one BTB domain, one BACK domain and six Kelch domains. These domains are involved in protein-protein interaction. The BTB domain interacts with a Cullin family protein. The BACK domain mediates the interaction between the BTB domain and a Cullin family protein. The Kelch domain interacts with a target protein.

A specific target of ubiquitination may be, for example, Unc119 etc. Unc119 binds to the a subunit of transducin, and is involved in translocation of the transducin α subunit from cell bodies to the outer segment. As previously described, the translocation of the transducin α subunit from cell bodies to the outer segment is inhibited by dark adaptation in Unc119 gene-deficient mice (Nat Neurosci. 2011 Jun. 5; 14(7): 874-80.). A mutation was found in the Unc119 gene in an autosomal dominant cone-rod dystrophy within one family (Invest Ophthalmol Vis Sci. 2000 October; 41(11): 3268-77.).

The ubiquitinating enzyme may exert its function in any types of cells in the retina, including, for example, photoreceptor cells, bipolar cells, ganglion cells, horizontal cells, amacrine cells, Muller cells, etc. Preferred are photoreceptor cells. The ubiquitinating enzyme may exert its function in rod photoreceptor cells or cone photoreceptor cells, but preferably exerts its function in rod photoreceptor cells.

Substance that Inhibits or Reduces Ubiquitination

The substance (A) includes a substances that inhibits or reduces the expression and/or activity of a ubiquitinating enzyme. Such a substance may be, for example, a substance that inhibits or reduces a ubiquitinating enzyme, a substance that inhibits or reduces the expression of a gene encoding a ubiquitinating enzyme, a substance that functions as a dominant negative protein that inhibits the interaction between a ubiquitinating enzyme and a target protein, a substance that inhibits or reduces the activity of a ubiquitination complex protein, or a substance that have any of these functions.

In another embodiment, the substance (A) may be, for example, a substance that inhibits or reduces ubiquitination, a substance that directly inhibits or reduces ubiquitination, etc. Such a substance may, for example, induce overexpression of a target protein of a ubiquitinating enzyme, thereby inhibiting or reducing ubiquitination by the ubiquitinating enzyme.

The ubiquitinating enzyme in the present invention may be encoded by the polynucleotide of SEQ ID NO: 1, 2, 10 or 11. The ubiquitinating enzyme in the present invention may be encoded by a polynucleotide encoding an isoform having the same or similar function as that of the ubiquitinating enzyme (i.e., the polynucleotide of SEQ ID NO: 4, 5, 7, 8, 13, 14, 16, 17, 19, 20, 22, 23, 25, 26, 28, 29, 31 or 32). The ubiquitinating enzyme in the present invention may be encoded by a nucleotide sequence that hybridizes with a DNA of a nucleotide sequence complementary to SEQ ID NO: 1, 2, 4, 5, 7, 8, 10, 11, 13, 14, 16, 17, 19, 20, 22, 23, 25, 26, 28, 29, 31 or 32 under stringent conditions and encodes Klhl18.

The nucleotide sequences of SEQ ID NOs: 2, 5, 8, 11, 14, 17, 20, 23, 26, 29 and 32 corresponds to positions 101 to 1825, positions 96 to 1835, positions 99 to 1430, positions 127 to 1851, positions 27 to 1781, positions 27 to 1766, positions 27 to 1766, positions 226 to 1644, positions 226 to 1629, positions 226 to 1614, and positions 319 to 1737 of the nucleotide sequence encoding the Klhl18 gene, respectively (The Klhl18 gene is encoded by SEQ ID NO: 1, 4, 7, 10, 13, 16, 19, 22, 25, 28 or 31).

The DNA that hybridizes with a DNA of a nucleotide sequence complementary to SEQ ID NO: 1, 2, 4, 5, 7, 8, 10, 11, 13, 14, 16, 17, 19, 20, 22, 23, 25, 26, 28, 29, 31 or 32 is, for example, a DNA containing a nucleotide sequence having a homology of about 70% or more, preferably about 80% or more, more preferably about 90% or more, most preferably about 95% or more to the nucleotide sequence of SEQ ID NO: 1, 2, 4, 5, 7, 8, 10, 11, 13, 14, 16, 17, 19, 20, 22, 23, 25, 26, 28, 29, 31 or 32.

The term "gene" herein is used interchangeably with "polynucleotide", "nucleic acid" or "nucleic acid molecule". The gene according to the present invention may exist as a RNA (e.g., a mRNA) or a DNA (e.g., a cDNA or a genomic DNA).

The DNA may be a double-stranded or single-stranded DNA. The single-stranded DNA or RNA may be a coding strand (a sense strand) or a non-coding strand (antisense strand). The 5' or 3' end of the polynucleotide in the present invention may be fused to a polynucleotide encoding a tag marker (a tag sequence or a marker sequence).

Hybridization can be performed by a known method or a modified method thereof, for example, in accordance with the method described in Molecular Cloning, 2nd, J. Sambrook et al., Cold Spring Harbor Lab. Press, 1989.

The term "stringent conditions" as used herein means the standard conditions, for example, the conditions described in Molecular Cloning, A Laboratory Manual, Second edition, 1989, Vol. 2, p. 11.45. In particular, the stringent conditions means that hybridization occurs at a temperature to 10° C. lower than the melting temperature (Tm) of a complete hybrid.

Specific examples of the substance (A) include, for example, an inhibitor of binding of a ubiquitinating enzyme; part of a ubiquitinating enzyme protein; a proteasome inhibitor; an antibody against a ubiquitinating enzyme; a siRNA, a shRNA, a dsRNA, a microRNA, an antisense polynucleotide, each against a ubiquitinating enzyme; a gene-targeting substance; a substance that inhibits the activity of a ubiquitination complex protein; a substance that inhibits or reduces ubiquitination by a ubiquitinating enzyme; etc. These substances may be used alone or as a mixture thereof. The source of these substances is not limited to a particular one, and the substances may be artificial substances, substances derived from animals or plants, or substances purified from a mixture (for example, an extract).

Inhibitor of Binding of Ubiquitinating Enzyme

The inhibitor of binding of a ubiquitinating enzyme may be any substance that inhibits the binding of a ubiquitinating enzyme to a protein. The protein to which a ubiquitinating enzyme binds may be, for example, a protein component of a ubiquitination complex, or a target protein of a ubiquitinating enzyme. The inhibitor of binding of a ubiquitinating enzyme may be, for example, a substance that denatures or alters a ubiquitinating enzyme. The substance that denatures or alters a ubiquitinating enzyme may be, for example, a substance that alters the three-dimensional structure of a ubiquitinating enzyme, a substance that blocks a site involved in the binding of a ubiquitinating enzyme, or other substances. The substance that alters the three-dimensional structure of a ubiquitinating enzyme may be, for example, a substance that alters the whole ubiquitinating enzyme or part of the three-dimensional structure thereof, a substance that degrades a ubiquitinating enzyme, or other substances. When part of the three-dimensional structure of a ubiquitinating enzyme is altered by such a substance, the three-dimensional structure may include, for example, at least the binding site of a ubiquitinating enzyme. The site involved in the binding of a ubiquitinating enzyme may be, for example, the binding site (binding domain) of a ubiquitinating enzyme, etc. The substance that blocks the binding site (binding domain) of a ubiquitinating enzyme may be, for example, a substance that binds to the binding site of a ubiquitinating enzyme to inhibit binding to a target protein, a substance that hides the recognition site for a target protein that is to be recognized by a ubiquitinating enzyme, or other substances.

The substance that inhibits the binding of a ubiquitinating enzyme may be, for example, a substance that pass through the blood-retinal barrier or the blood-brain barrier, a substance that promotes penetration through the blood-retinal barrier or the blood-brain barrier, or other substances.

The inhibitor of binding of a ubiquitinating enzyme may be a known substance, or can be identified, designed or searched using a known method.

For example, the inhibitor of binding of a ubiquitinating enzyme may be designed based on the information (for example, the shape, structure, chemical properties, etc.) of an identified site that is involved in the binding (e.g., the binding site etc.) of a ubiquitinating enzyme.

In such a procedure, the site involved in the binding of a ubiquitinating enzyme may be identified by any method, and the conventional method can be used. For example, the binding site on a ubiquitinating enzyme or the biding site on a target protein may be identified, using a known software (for example, molecular simulation software), by estimating the three-dimensional structure of the ubiquitinating enzyme or the target protein based on the amino acid sequence of the ubiquitinating enzyme (for example, SEQ ID NO: 3, 6, 9, 12, 15, 18, 21, 24, 27, 30 or 33) or the amino acid sequence of the target protein of the ubiquitinating enzyme (for example, SEQ ID NO: 36, 39, 42, 45, 48, 51, 54 or 57). Examples of the molecular simulation software include SWISS-model (http://swissmodel.expasy.org), myPresto (Medicinally Yielding PRotein Engineering SimulaTOr), PALLAS, and MUSES. PALLAS can select two or three sets of protein structures suitable for docking from protein structure assemblies obtained by X-ray diffraction, NMR, molecular dynamics simulation, etc. MUSES is a high-precision discrimination system for activity and can distinguish active compounds from inactive compounds in the compounds selected by PALLAS.

The substance that alters the three-dimensional structure of a ubiquitinating enzyme is not limited to a particular one, and may be identified by, for example, molecular dynamics simulation. Molecular dynamics simulation can be used to, for example, estimate the changes in the three-dimensional structure of a ubiquitinating enzyme before and after the binding or interaction with a substance, thereby identifying the substance that alters the three-dimensional structure of a ubiquitinating enzyme. Examples of the molecular dynamics simulation include myPresto etc.

Part of Ubiquitinating Enzyme Protein

Part of a ubiquitinating enzyme protein may serve as, for example, a dominant negative protein that inhibits the interaction between a ubiquitinating enzyme and a target protein. Examples of part of a ubiquitinating enzyme protein include Klhl18 protein lacking the region involved in ubiquitination activity, and Klhl18 protein that contains part of Klhl18 protein serving as a binding region for a target protein and lacks the region involved in ubiquitination activity. Further examples of part of a ubiquitinating enzyme include a non-full-length protein containing the C-terminal 298 residues of Klhl18 protein, the C-terminal 298 residues of Klhl18 protein, and a region that is present in the C-terminal 298 residues of Klhl18 protein and has the ability to inhibit or reduce a ubiquitinating enzyme.

Proteasome Inhibitor

Examples of proteasome inhibitors include MG-132, bortezomib, disulfiram, epigallocatechin gallate (EGCG), salinosporamide A, carfilzomib, lactacystin, TMC-95, peptide aldehyde, peptide ketoamide, ketoaldehyde, peptide epoxyketone, peptide boric acid and a pharmaceutically acceptable salt thereof.

Antibody

The antibody may be any antibody that recognizes a ubiquitinating enzyme. Examples of the antibody include antagonistic antibodies, i.e., antibodies that inhibit one or more functions of a ubiquitinating enzyme; and agonistic antibodies; etc. The antibody according to the present invention may be a human antibody, a non-human antibody, a humanized antibody of a non-human origin, etc. The antibodies may be commercially available antibodies or in-house prepared antibodies. The antibody can be prepared by attaching a ubiquitinating enzyme polypeptide or peptide (an antigenic fragment of a ubiquitinating enzyme) to another molecule, or by administering a ubiquitinating enzyme or peptide together with an adjuvant. The coding sequence of the immunogen may be included in an expression cassette or vector that allows the immunogen to be expressed in vivo (see, for example, Katsumi (1994) Hum. Gene Ther. 5:1335-9). The preparation methods of polyclonal or monoclonal antibodies are known to those skilled in the art, and may be a known method such as the methods described in scientific literature and patent literature.

Human antibodies can be prepared in mice manipulated to produce only human antibodies as described in, for example, U.S. Pat. Nos. 5,877,397; 5,874,299; 5,789,650; and 5,939,598. B cells of the mice can be immortalized by standard techniques (for example, by fusing to an immortal cell line such as myeloma, or by manipulating B cells to persistently survive by another technique) (see, e.g., U.S. Pat. Nos. 5,916,771 and 5,985,615) to give cells capable of producing monoclonal human antibodies. Besides the traditional in vivo methods using animals, the antibodies can also be generated in vitro by using, for example, phage display libraries expressing recombinant antibody binding sites.

A "humanized" form of a non-human (for example, rodent) antibodies is a chimeric antibody that contains a minimal sequence derived from non-human immunoglobulin. A humanized antibody is a human immunoglobulin in which the hypervariable region is replaced with the residues of a hypervariable region with the desired specificity, affinity, and/or capacity derived from a non-human species, such as mice, rats, rabbits, or non-human primates. In some cases, the residues of the framework region (FR) of the human immunoglobulin may be substituted with the corresponding residues of a non-human species. The humanized antibody may contain residues that are not found in a human or non-human antibody. These modifications are made to further enhance the ability of the antibody. In general, a humanized antibody substantially contains at least one full-length variable region, typically two full-length variable regions, and all or substantially all of the hypervariable loops are from a non-human immunoglobulin, and all or substantially all of the FRs are from a human immunoglobulin sequence. The humanized antibody may typically contain the constant region (Fc) of a human immunoglobulin, and may optionally contain at least part of the constant region (Fc) of a human immunoglobulin. The humanization techniques are described in, for example, U.S. Pat. Nos. 5,585,089, 5,693,761; 5,693,762; and 6,180,370 granted to Queen et al., which are incorporated herein by reference.

In addition to full-length monoclonal and polyclonal antibodies, various types of genetically engineered antibodies and antibody fragments (e.g., $F(ab')_2$, Fab', Fab, Fv, and sFv fragments), and other fragments that retain antigen binding function and specificity of a parent antibody can be produced by standard techniques. A shorter version of a monoclonal antibodies can be produced by, for example, a recombinant technique by preparing a plasmid that expresses a desired fragment of a monoclonal antibody in an appropriate host. Ladner (U.S. Pat. Nos. 4,946,778 and 4,704,692) describes methods for preparing single polypeptide chain antibodies.

The term "antigenic fragment" as used herein refers to part of a polypeptide that contains one or more epitopes. Epitopes may be linear epitopes substantially containing a linear sequence from an antigen, or conformational epitopes containing sequences that are genetically separated by other sequences but come together structurally at the binding site for a polypeptide ligand. The "antigenic fragment" may be up to 5000, 1000, 500, 400, 300, 200, 100, 50, 25, 20, 10 or 5 amino acids in length.

The term "fragment" as used herein refers to a peptide or polypeptide containing at least 5 adjacent amino acid residues, at least 10 adjacent amino acid residues, at least 15 adjacent amino acid residues, at least 20 adjacent amino acid residues, at least 25 adjacent amino acid residues, at least 40 adjacent amino acid residues, at least 50 adjacent amino acid residues, at least 60 adjacent amino residues, at least 70 adjacent amino acid residues, at least adjacent 80 amino acid residues, at least adjacent 90 amino acid residues, at least adjacent 100 amino acid residues, at least adjacent 125 amino acid residues, at least 150 adjacent amino acid residues, at least adjacent 175 amino acid residues, at least adjacent 200 amino acid residues, or at least adjacent 250 amino acid residues of the amino acid sequence of a polypeptide or a protein.

In a specific embodiment, the fragment of a protein or polypeptide retains at least one function of the protein or polypeptide. In another embodiment, the fragment of a protein or polypeptide retains at least one, two, three, four or five functions of the protein or polypeptide. Preferably, the fragment of an antibody retains the ability to specifically bind to an antigen.

siRNA

A siRNA (short interfering RNA) is a double-stranded RNA of about 20 nucleotides or less in length, and can be introduced into cells to inhibit the expression of a target gene. A protein specific to a siRNA binds to the siRNA to form the RISC complex. The RISC complex recognizes and binds to a mRNA of the same sequence as that of the siRNA and cleaves the mRNA at the center of the siRNA. The siRNA in the present invention may be any siRNA that induce RNAi to inhibit the production of a protein from a ubiquitinating enzyme gene, and may include an artificially synthesized siRNA, a biochemically synthesized siRNA, a siRNA synthesized in a living body, or a double-stranded short RNA of 10 base pairs or more resulted from degradation of a double-stranded RNA of about 40 bases or more in a living body. The siRNA sequence and the mRNA sequence to be cleaved as a target are preferably match at 100%, but the sequences are not always required to match at 100% as long as the cleaving activity remains.

The siRNA can be designed and prepared by a known method. For example, the siRNA may be prepared as follows. The sense and antisense strands of a target sequence on a mRNA are synthesized with a DNA/RNA automatic synthesizer based on the sequence information of a ubiquitinating enzyme acquired from a database such as GenBank. The sense and antisense strands are then denatured in a appropriate annealing buffer at about 90 to about 95° C. for about 1 minute, and then annealed at about 30 to about 70° C. for about 1 to about 8 hours. Alternatively, the siRNA may be prepared by synthesizing a short hairpin RNA (shRNA) as a siRNA precursor, and cleaving the shRNA with a dicer.

shRNA

A shRNA (short hairpin RNA) is a single-stranded RNA molecule of about 20 or more base pairs containing a palindromic nucleotide sequence over part of its length to form a hairpin double-strand structure. Such a shRNA, after introduced into cells, is degraded in the cells into a length of about 20 bases, and induces RNAi in a similar manner as siRNAs. The shRNA in the present invention may be any shRNA that induces RNAi to inhibit the production of a protein from the Klhl18 gene, but the shRNA preferably have a 3' overhang. The length of the double-stranded portion of the shRNA is preferably about 10 or more nucleotides, and more preferably about 20 or more nucleotides.

The shRNA can be designed and prepared by a known method. For example, the shRNA can be prepared by obtaining the sequence information of a ubiquitinating enzyme from a databases such as GenBank, then designing, based on the sequence information, an oligo RNA containing nucleotide sequences connected by a spacer sequence of a length (for example, about 5 to 25 bases) that enables the formation of a loop structure appropriate for the sense and antisense strands of a target sequence on a mRNA, and synthesizing the oligo RNA with an automated DNA/RNA synthesizer.

A nucleic acid designed to produce a siRNA against the mRNA of a ubiquitinating enzyme gene in vivo is also defined herein to be included in the nucleic acid containing or partially containing a nucleotide sequence complementary or substantially complementary to the nucleotide sequence of the mRNA of a ubiquitinating enzyme gene. Such a nucleic acid include an expression vector designed to express the above shRNA or siRNA. Vectors that express a shRNA includes the tandem type or the stem loop (hairpin) type. The former is an expression vector in which an expression cassette for the sense siRNA strand is connected with an expression cassette for the antisense siRNA strand in tandem, and the strands are expressed in cells and then annealed to form a double-stranded siRNA (dsRNA). The latter is an expression vector in which an expression cassette for a shRNA is inserted, and the shRNA is expressed in cells and undergoes processing by a dicer to form a dsRNA. The promoter may be a pol III promoter. Examples of the pol III promoter include mouse and human U6-snRNA promoter, human Hl-RNase P RNA promoter, human valine-tRNA promoter, etc. The transcription termination signal may be a sequence of contiguous 4 or more T residues.

The siRNA or shRNA expression cassette constructed as described above may be then inserted into a plasmid vector or a virus vector. Examples of the vector include virus vectors such as retrovirus, lentivirus, adenovirus, adeno-associated virus, herpesvirus and Sendai virus; and expression plasmids for animal cells.

dsRNA

A dsRNA (double-stranded RNA) is a molecule that can be converted into a siRNA in cells. A dsRNA that generates the above siRNA may be used in the present invention. The dsRNA in the present invention may be any dsRNA that induces RNAi to inhibit the production of a protein from a ubiquitinating enzyme gene. Preferably, the sequence of the dsRNA matches at 100% with the sequence of the mRNA as a target to be cleaved, but the sequences are not always required to match at 100% as long as the cleaving activity by RNAi remains.

The dsRNA can be designed and prepared by a known method.

microRNA

The term “microRNA” means a single-stranded RNA molecule that regulates gene expression and is composed of 10 to 50 nucleotides, preferably 15 to 40 nucleotides, and more preferably 17 to 25 nucleotides over the length. The microRNA is preferably an oligonucleotide that is not expressed in cells and has a short stem-loop structure. The microRNA is preferably has a complete or partial homology to one or more mRNAs, but may be any microRNA that inhibits the expression of the target gene via complementary binding to the mRNAs.

The microRNA can be designed and prepared by a known method. For example, the microRNA can be prepared in accordance with the method described above for the siRNA.

Antisense Polynucleotide

The antisense polynucleotide may be any polynucleotide that inhibits the production of a protein from a ubiquitinating enzyme gene. For example, the antisense polynucleotide is a polynucleotide that hybridizes to contiguous 5 to 100 nucleotides in the DNA sequence of a ubiquitinating enzyme gene. The antisense polynucleotide may be a DNA or RNA, and may be modified DNA or RNA. The antisense polynucleotide is preferably 5 to 50 nucleotides in length, and more preferably 9 to 25 nucleotides in length.

The antisense polynucleotide can be designed and prepared by a known method.

Aptamer

The term “aptamer” means a nucleic acid molecule or a peptide that specifically binds to a specific molecular target. The aptamer in the present invention may be any aptamer that inhibits the activity and/or expression of a ubiquitinating enzyme.

Gene-Targeting Ssubstance

Gene targeting is a technique that uses homologous recombination or other means to modify an endogenous gene to delete a gene, introduce a gene, or introduce a point mutation. Examples of gene targeting methods include genome editing. Genome editing enables specific modification (deletion, substitution, insertion) of nucleotides in a genome region of interest. In particular, genome editing can be performed by introducing double-strand break (DSB) at a specific site of a genomic region, for example, a specific locus; isolating a DNA sequence homologous to the genomic region of interest; modifying the isolated DNA; introducing the modified DNA into cells to allow recombination to occur between the genome sequence and the exogenous homologous sequence, thereby modifying the genome.

The gene-targeting substance may be any substance that is capable of modifying a genome sequence, and may be, for example, a DNA or RNA. The specific embodiments of the gene-targeting substance are not limited as long as the gene-targeting substance can modify the genome sequence. The gene-targeting substance may be a gene-targeting vector (plasmid), and a viral DNA or RNA, or a portion thereof. The gene-targeting vector (plasmid) for genome editing may be, for example, a vector that can modify a gene (genomic sequence) encoding a ubiquitinating enzyme to inhibit or reduce ubiquitination, or a vector that can modify a genomic sequence of, for example, a protein involved in ubiquitination via the interaction with a ubiquitinating enzyme to inhibit or reduce ubiquitination. The virus containing the gene-targeting substance may be any virus that is capable of modifying a genome sequence, and may be, for example, a retrovirus or a lentivirus.

The genome editing is not limited to a particular one, and may be, for example, a known genome editing technique. Examples of the known genome editing technique include gene editing systems such as CRISPR/Cas9 (clustered regularly interspaced short palindromic repeats/CRISPR associated proteins 9) system.

The gene-targeting substance can be designed and produced by a known method. The gene-targeting substance can be introduced into a living body, cultured cells, etc. by a known method.

Substance that Inhibits the Activity of Ubiquitination Complex Protein

The substance that inhibits the activity of a ubiquitination complex protein include a substance that inhibits the activity of a protein component of a ubiquitination complex. Examples of the substance that inhibits the activity of a protein component of a ubiquitination complex include MLN4924 and DI-591, which inhibit the activity of Cullin 3 protein; Suramin, which inhibits the activity of Cullin 2, 3 and 4A proteins, and PYR-41, which is an inhibitor of E1 ubiquitin ligase; etc.

The protein component of a ubiquitination complex protein include Cullin 1, 2, 3, 4A, 4B, 5, 7 and 9, ROC1 protein, E1 ubiquitin ligase, E2 ubiquitin ligase, ubiquitin protein, etc.

Substance that Inhibits or Reduces Ubiquitination by Ubiquitinating Enzyme

The substance that inhibits or reduces ubiquitination by a ubiquitinating enzyme include, for example, a target protein of a ubiquitinating enzyme, a gene encoding a target protein of a ubiquitinating enzyme, and a substance that induces or promotes the expression of a target protein of a ubiquitinating enzyme, etc. The target protein of a ubiquitinating enzyme may be the full-length of a target protein, part of a target protein, etc., and examples of the part of a target protein include part of a protein containing the region to be ubiquitinated in the target protein. Examples of the target protein include those described in paragraph [0018] of WO 2018/169090.

Symptoms Related to Light Reception and Specific Use of the Agent

The agent of the present invention is capable of inhibiting or reducing light sensitivity (photosensitivity). Therefore the agent is effective for ameliorating or preventing a symptom related to or associated with the light sensitivity. In particular, the regulation of light sensitivity plays the central role (the starting point) of light reception, and hence inhibition or reduction of light sensitivity ameliorates or prevents a symptom associated with light reception (overall light reception). For example, the inhibition or reduction of light sensitivity leads to inhibition or suppression of direct regulatory functions on light reception (for example, light adaptation and dark adaptation), and then leads to inhibition or suppression of a series of subsequent light reception functions (for example, conversion of the light stimulus into signals, transmission of the converted signals to cells, transmission of the converted signals to the brain, etc.).

The symptom associated with light reception (sometimes called the symptom (B), etc.) may be any symptom affected by light reception, and typically may be symptom that progress or worsen by light reception.

The cause of the occurrence (onset) of the symptom is not limited to a particular one as long as the symptom is affected by light reception, but the symptom is not necessarily caused by light reception. For example, retinal degeneration is worsened or progressed by light reception, but the cause of its occurrence is not necessarily light reception. Therefore the amelioration or prevention of such a symptom not caused by light reception is also included in the present invention.

The symptom (B) may be, for example, a symptom in the retina or a symptom that occurs due to impairment in the retina. The symptom that occurs due to impairment in the retina may be, for example, a symptom that occurs in the brain. The symptoms that occur in the retina may be, for example, a symptom caused by light stimulation or light stress received in daily life, or a symptom caused by exposure to strong light. The symptom that occurs in the brain due to impairment in the retina may be, for example, a symptom caused by hyperesthesia.

Specifically, the agent of the present invention may be used as, for example, a retinal protective agent [for example, an agent for maintaining or retaining the conditions and/or functions of the retina (for example, an agent for preventing or ameliorating retinal disorders, retinal disorders such as reduction in vision, visual field constriction and blindness due to retinal degeneration induced by light exposure, and eye strain caused by light exposure)], an inhibitory agent for retinal degeneration (for example, an agent for preventing retinal cells from degeneration or for protecting retinal cells from degeneration), an inhibitory agent for retinal aging (for example, an agent for preventing the accumulation of damage in retinal cells), an agent for ameliorating or inhibiting hyperesthesia (for example, an agent for ameliorating or preventing a symptom caused or exacerbated by hyperesthesia to light stimulation), an agent for ameliorating or preventing light-induced diseases (for example, an agent for ameliorating or preventing diseases induced by light stimulation), an agent for ameliorating or preventing light-induced disorders (an agent for ameliorating or preventing disorders induced by light stimulation), or the like.

More specifically, the agent of the present invention may be used in amelioration or prevention of age-related macular degeneration, retinitis pigmentosa, Leber congenital amaurosis, Stargardt disease (juvenile macular degeneration), cone-rod dystrophy, diabetic retinopathy, macular edema, retinal ischemia, photosensitive seizure, photosensitive epilepsy, photic maculopathy, asthenopia, retinal dysfunction (for example, due to aging etc.), sleep disturbance, migraine, light-induced damage (for example, light-induced damage caused by outdoor activities, sports, or mountaineering under the sun or caused by the blue light emitted from computer displays, etc.), psychiatric disorders accompanied by hyperesthesia or visual cognitive impairment [for example, depression, depressive state, bipolar disorder (manic depression), autism, mental development disorder, schizophrenia, etc.], etc.

As is clear from the above description, the inhibition of light sensitivity leads to amelioration or prevention of the above diseases or symptoms. For example, mice deficient in the RPE65 gene or the Sag (arrestin) gene, which is a causative gene for human retinitis pigmentosa, develop the degeneration of photoreceptor cells and are used as a model mouse of inherited retinitis pigmentosa. The mechanism of photoreceptor degeneration due to gene defect is different depending on the responsive gene. The degeneration of photoreceptor cells due to the deficiency of the RPE65 gene is caused by abnormal metabolism of vitamin A, whereas the degeneration of photoreceptor cells due to the deficiency of the Sag gene is caused by the abnormal light reaction of photoreceptor cells. Mice deficient in the Gnat1 gene, which is transducin, is known as a mouse model with suppressed light sensitivity. As previously reported, when RPE65 gene-deficient mice or Sag gene-deficient mice are crossed with Gnat1 gene-deficient mice, hereditary retinal degeneration due to the RPE65 gene deficiency or Sag gene deficiency is suppressed (BioEssays. 2006, 28: 344-354; Nat. Genet., 2002, 32, 254-260). These reports provide the basis of understanding that the agent of the present invention can be used for amelioration or prevention of the above diseases or symptoms.

Other Ingredients

The agent of the present invention is only required to contain a substance that inhibits or reduces ubiquitination, and may further contain as appropriate another ingredient depending on the type of the substance (A), the dosage form, the administration mode, the desired efficacy, etc. Examples of said another ingredient include another pharmacologically active ingredient, a carrier, and an additive (such as a preservative, a surfactant, a stabilizer, an isotonic agent, a pH adjuster, etc.). These ingredients may be used alone or in combination of two or more types.

Administration Method, Dosage Form, etc.

The administration mode (or the dosage form) of the agent or substance (A) of the present invention may be any mode of administration that allows the agent or substance (A) to exhibit the effect of ameliorating or preventing a symptom associated with light reception. The agent or substance (A) may be administered, for example, via an oral route (as an oral agent) or a parenteral route (a parenteral agent), etc.

Examples of the parenteral agent include injections (for example, intraocular, subcutaneous, intravenous, intramuscular, and intraperitoneal injections), eye drops, intravenous infusions, external preparations (for example, transnasal preparations, transdermal preparations or ointments), suppositories (for example, rectal suppositories, vaginal suppositories), etc. The oral agent may be prepared by blending the substance that inhibits or reduces a ubiquitinating enzyme with a pharmaceutically acceptable carrier and formulating into a suitable dosage form, including, for example, a solid dosage form such as tablets (including sugar-coated tablets), pills, capsules, powders and granules; a liquid dosage form such as solutions, suspensions, emulsions, syrups and elixirs; and a semi-solid dosage form such as jelly preparations; etc.

In particular, the agent or substance (A) of the present invention is preferably administered in such a manner that the agent or substance (A) efficiently inhibits or reduces ubiquitination in the retina. Therefore, the agent of the present invention is preferably in the form of an injection (an intraocular or intravitreous injection), an eye drop (an ophthalmic composition), or the like, and is preferably administered via an intraocular injection, an eye drop, etc.

The agent or substance (A) of the present invention can be used to prepare various types of preparations (compositions, and pharmaceutical compositions) according to various embodiments, as described above. The present invention thus includes a composition [for example, an injectable composition, an ophthalmic composition (an eye drop composition)] containing the agent (or the substance).

The agent or substance (A) of the present invention can be used in the field of food products. That is, the agent (or substance (A)) of the present invention may be a food additive. Such a food additive can be used to prepare a food product. The present invention therefore also includes a food product (a food composition) containing the agent (or the substance (A)).

Examples of the food product include food and drink products, such as supplemental foods, balanced nutritional foods, health foods, foods with nutrient function claims, foods for specified health use, and foods for patients. These food and drink products may be produced by any method that allows the food and drink products to exhibit the effect of ameliorating or preventing a symptom associated with light reception. Specific examples of suitable food products include supplements in the form of a powder, granules, a capsule, a tablet, etc. In addition to the food products in the form as described above, the foods and drinks also include, for example, confectionaries such as chewing gum, hard candy, gummy candy, tablet candy, cookies, cakes, chocolate, ice cream, jelly, mousse, pudding, biscuits, corn flakes, chewable tablets, wafers, and rice crackers; drinks such as carbonated drinks, soft drinks, milk beverages, coffee drinks, black tea drinks, fruit juice drinks, nutritional drinks, alcoholic drinks, and mineral water; powdered drinks such as powdered juice and powdered soup; seasonings such as dressing and sauce; bread; noodles; steamed fish paste such as fish cake; and rice seasonings. Besides such forms for oral intake, the food product may be in the form for enteral intake (a liquid food, etc.).

The amount of the agent contained in the food product of the present invention can be adjusted as appropriate for the dose, the form of the food product, or the like selected as appropriate depending on the age, sex, health conditions and other conditions of the subject. The food product of the present invention containing a large amount of the agent can also be provided to allow the agent to effectively exhibit the amelioration effects or prevention effects according to the present invention.

The animal to which the agent of the present invention is to be administered may be a human or a non-human animal, and includes mammals, but is not limited thereto. Examples of mammals include primates such as humans, monkeys, orangutans, chimpanzees, and gorillas; experimental animals such as rabbits and rodents such as mice, rats, hamsters, and guinea pigs; domestic animals such as cow, horses, pigs, sheep, and goats; pets such as dogs and cats; and birds such as chickens, ducks and geese. The mammals are preferably primates (such as humans) or pets, more preferably humans, dogs or cats, and further preferably humans.

The dose (or intake) of the agent or substance (A) of the present invention varies depending on the administration subject, the target disease, the symptoms, the administration route, the administration interval, etc. The single dose of the substance (A) may be, for example, about 0.0001 mg to about 100 g, about 0.001 mg to about 50 g, about 0.01 mg to about 10 g, about 0.1 mg to about 1 g, or the like. The dose of the antibody varies depending on the administration subject (for example, a primate), the administration route (for example, administration to the vitreous body), etc., and the single dose of the antibody may be, for example, about 0.01 mg to about 100 mg, about 0.1 mg to about 50 mg, about 1 mg to about 20 mg, about 1.5 mg to about 10 mg, or the like. The dose of the proteasome inhibitor varies depending on the administration subject (for example, a pet), the administration route (for example, administration to the vitreous body), etc., and the single dose of the proteasome inhibitor may be, for example, about 0.001 mg to about 10 mg, about 0.01 mg to about 1 mg, about 0.05 mg to about 0.5 mg, about 0.07 mg to about 0.1 mg, or the like.

The interval of administration of the antibody varies depending on the administration subject (for example, a primate), the administration route (for example, administration to the vitreous body), etc., and the antibody may be administered, for example, once a month for consecutive three months or may be administered once every two months. The interval of administration of the proteasome inhibitor varies depending on the administration subject (for example, a pet), the administration route (for example, administration to the vitreous body), etc., and the proteasome inhibitor may be administered, for example, every day, every several days, or every several weeks.

The environment during administration of the agent or substance (A) of the present invention is not limited as long as the agent or substance (A) efficiently inhibits or reduces ubiquitination in the retina, and may be the dark environment (in a dark place) or the light environment (in a light place). The agent is preferably administered in the light environment (in a light place) to more effectively inhibit ubiquitination by Klhl18.

The level of illumination in the light environment (in a light place) in which the agent or substance (A) of the present invention is administered is not limited as long as the level of illumination is, for example, 300 lux or more, 500 lux or more, 800 lux or more, 1,000 lux or more, etc. The level of illumination may be, for example, 1,000,000 lux or less, 200,000 lux or less, etc. The level of illumination in the dark environment (in a dark place) may be, for example, 0 lux or more and less than 300 lux, 0 lux to 200 lux, 0 lux to 100 lux, 0 lux to 50 lux, 0 lux to 10 lux, 0 lux to 8 lux, 0 lux to 5 lux, 0 lux to 3 lux, 0 lux to 1 lux, 0 lux to 0.5 lux, 0 lux to 0.1 lux, etc.

Evaluation of Inhibition

The degree of inhibition or reduction of ubiquitination may be evaluated or determined by, for example, a forced expression experiment using cultured cells, in vitro experiments such as the FRET method, etc. When the degree of inhibition or reduction of ubiquitination is evaluated or determined by a forced expression experiment using cultured cells, the ubiquitination may be inhibited or reduced by, for example, 20% to 100%, preferably by 50% to 100%, more preferably by 70% to 100%, and further preferably by 90% to 100%.

Screening Method

The present invention also includes a screening method using a ubiquitinating enzyme for screening for a substance that inhibits or reduces ubiquitination, or for an agent for ameliorating or preventing a symptom associated with light reception. The term "screening" as used herein refers to screening for a substance having an activity of interest from a large number of various test substances, or the detection of a test substance to determine whether the test substance has characteristics of interest.

In a preferred embodiment of the present invention, the effect of ameliorating or preventing a symptoms associated with light reception is used as an indicator, and is evaluated by determining the degree of ubiquitination of a target protein of a ubiquitinating enzyme. The degree of ubiquitination may be evaluated by the above determination method.

The degree of ubiquitination of the target protein is determined by, for example, introducing a gene encoding a ubiquitinating enzyme together with a gene encoding a target protein into cells, and determining that the test substance has the effect of ameliorating or preventing a symptom associated with light reception when the amount of ubiquitin conjugated to the target protein in the cells with addition of the test substance is reduced as compared with that in cells with no addition of the test substance. When the amount of the ubiquitin is increased, the test substance can be determined to have an effect of enhancing the activity of a ubiquitinating enzyme. The amount of ubiquitin can be measured by, for example, extracting proteins from cells and performing quantitative detection by Western blotting etc.

In another embodiment, the effect of ameliorating or preventing a symptom associated with light reception as an indicator may be evaluated by determining the activity of a ubiquitinating enzyme. The activity of a ubiquitinating enzyme may be expressed in the expression level of the target protein. The effect of ameliorating or preventing a symptom associated with light reception is determined by, for example, introducing a gene encoding a ubiquitinating enzyme into cells, and determining that the test substance has the effect of ameliorating or preventing a symptom associated with light reception when the expression level of the target protein in the cells with addition of the test substance is increased as compared with that in cells with no addition of the test substance. When the expression level of the target protein is reduced, the test substance can be determined to have an effect of enhancing the activity of a ubiquitinating enzyme. The expression level of the target protein can be measured by, for example, extracting proteins from cells and performing quantitative detection by Western blotting etc. Alternatively, the expression level of the target protein may be determined by quantifying the amount of the protein in cells by a known method.

The type of cells used for the screening may be any cells that are capable of growing in the presence of a ubiquitinating enzyme and/or a target protein of a ubiquitinating enzyme, and are capable of producing a ubiquitinating enzyme and/or a target protein introduced therein. Examples of the cells include HEK293T cells, Neuro2a cells, NIH3T3 cells, etc. The cells are cultured under the standard conditions in, for example, a commercially available DMEM medium, and the culture conditions are not limited as long as the screening method of the present invention is not difficult to perform.

In an embodiment, the screening method of the present invention is for screening for a substance that inhibits or reduces the interaction between an enzyme involved in ubiquitination and a target protein or the interaction between an enzyme involved in ubiquitination and a protein component of a ubiquitin ligase complex. Specifically, for example, when the interaction between a ubiquitinating enzyme and a target protein or the interaction between a ubiquitinating enzyme and a protein component of a ubiquitin ligase complex in the presence of the test substance is reduced as compared with that in the absence of the test substance, the test substance is determined to have an effect of ameliorating or preventing a symptom associated with light reception. When the interaction between a ubiquitinating enzyme and a target protein or the interaction between a ubiquitinating enzyme and a protein component of a ubiquitin ligase complex is increased in the presence of the test substance, the test substance can be determined to have an effect of enhancing the activity of the ubiquitinating enzyme. The interaction can be measured by using a complex composed of a ubiquitinating enzyme and a target protein (protein association) as an indicator. The interaction can be evaluated by known techniques, such as FRET (Fluorescence Resonance Energy Transfer), Alpha Screen (Amplified Luminescence Proximity Homogenous Assay), immunoprecipitation, Western blotting, $^{35}$S-methionine labeling of proteins, microsequencing of proteins, silver staining and two-dimensional gel electrophoresis. In an embodiment, for example, the protein interaction between Klhl18 protein and Unc119 protein in the presence or absence of a test substance is evaluated by measuring the interaction by FRET.

The test substance targeted by the screening method of the present invention may be any substance that inhibits or reduces ubiquitination. The test substance is preferably has the ability to inhibit or reduce a ubiquitinating enzyme, a gene encoding a ubiquitinating enzyme, and/or the expression of a ubiquitinating enzyme. Examples of the test substance include the substance (A) etc. The test substance may be a mixture containing the substance (A).

Agent for Enhancing or Maintaining Light Sensitivity

The present invention includes an agent for enhancing or maintaining light sensitivity. In the present invention, the agent for enhancing or maintaining light sensitivity may be any agent containing a substance having the ability to induce, promote or maintain ubiquitination. For example, the agent may comprise at least one selected from a ubiquitinating enzyme (for example, the ubiquitinating enzyme as described above), a gene encoding a ubiquitinating enzyme (for example, a gene encoding the ubiquitinating enzyme as described above), a substance having the ability to induce or promote the expression of a ubiquitinating enzyme, a substance having the ability to enhance the activity of a ubiquitinating enzyme, and a substance having the ability to enhance the interaction between a ubiquitinating enzyme and a target protein or the interaction between a ubiquitinating enzyme and a protein component of a ubiquitin ligase complex, and a combination of two or more thereof. The substance having the ability to induce or promote the expression of a ubiquitinating enzyme may be, for example, a transcription factor. The transcription factor is only required to have the ability to induce or promote the expression of a ubiquitinating enzyme. For example, the transcription factor may be capable of inducing or promoting the expression of a ubiquitinating enzyme directly or indirectly. The term "directly" means, for example, that a transcription factor induces or promotes the expression of a ubiquitinating enzyme. The term "indirectly" means, for example, that a transcription factor induces or promotes the expression of a ubiquitinating enzyme via another protein or the like. Examples of the transcription factor that directly induce or promote the expression of a ubiquitinating enzyme include Otx2 (Orthodenticle homeobox 2), Crx (Cone-rod homeobox), and Nrl (Neural retina leucine zipper). The substance having the ability to induce or promote the expression of a ubiquitinating enzyme may be, for example, a gene encoding a transcription factor. The gene encoding a transcription factor may be, for example, the gene encoding a transcription factor, or a gene containing a sequence encoding a transcription factor.

The amino acid sequence and nucleotide sequence of a transcription factor are available from databases etc. known in the art.

The agent for enhancing or maintaining light sensitivity may be used for, for example, a symptom associated with reduction in the light sensitivity of the retina and other symptoms. The symptom associated with reduction in the light sensitivity may be any symptom affected by light reception, and typically may be symptom that progress or worsen by light reception.

The cause of the occurrence (onset) of the symptom is not limited to a particular one as long as the symptom is affected by light reception, but the symptom is not necessarily caused by light reception. Therefore the amelioration or prevention of such a symptom not caused by light reception is also included in the present invention.

The agent for enhancing or maintaining the light sensitivity of the retina may be used as, for example, an agent for ameliorating or preventing for night blindness, etc.

The environment during administration of the agent for enhancing or maintaining light sensitivity is not limited as long as the agent efficiently enhances or maintains ubiquitination in the retina, and may be the dark environment (in a dark place) or the light environment (in a light place). The agent is preferably administered in the dark environment (in a dark place) to more effectively enhance ubiquitination effect of Klhl18.

The level of illumination in the light environment (in a light place) in which the agent for enhancing or maintaining light sensitivity is administered is not limited as long as the level of illumination is, for example, 300 lux or more, 500 lux or more, 800 lux or more, 1,000 lux or more, etc. The level of illumination may be, for example, 1,000,000 lux or less, 200,000 lux or less, etc. The level of illumination in the dark environment (in a dark place) may be, for example, 0 lux or more and less than 300 lux, 0 lux to 200 lux, 0 lux to 100 lux, 0 lux to 50 lux, 0 lux to 10 lux, 0 lux to 8 lux, 0 lux to 5 lux, 0 lux to 3 lux, 0 lux to 1 lux, 0 lux to 0.5 lux, 0 lux to 0.1 lux, etc.

Embodiments of the present invention will be described in more detail with reference to Examples below, but the present invention is not limited thereto.

EXAMPLES

Example 1: Expression Analysis of Klhl18 Gene in Mouse Tissue

Northern Blotting (1) Preparation of Probe for Northern Blot Analysis

RNA was extracted from the retina of ICR mice of postnatal 14 days (purchased from Oriental Yeast Co., Ltd.) using Trizol reagent (Thermo Fisher Scientific) according to the attached protocol, and then a cDNA library was prepared according to the conventional method. PCR was performed with Ex Taq (Takara) using the cDNA library as a template according to the attached protocol to amplify the Klhl18 gene. The primers used for the PCR were a forward primer (SEQ ID NO: 58) and a reverse primer (SEQ ID NO: 59). The amplified PCR fragment was integrated into the pGEM-T-easy plasmid (Promega) using Ligation High Ver. 2 (TOYOBO) according to the attached protocol to give the pGEM-T-easy-Klhl18 plasmid.

A Klhl18 DNA fragment was excised from the pGEM-T-easy-Klhl18 plasmid with the restriction enzyme EcoRI. The Klhl18 DNA fragment was radioactively labeled with $^{32}$P dCTP (PerkinElmer) according to the attached protocol using Rediprime™ Ramdom Prime Labeling System (GE Healthcare) to give a probe for Northern blotting.

(2) RNA Preparation and Hybridization

Four weeks old ICR mice (purchased from Oriental Yeast Co., Ltd.) were dissected according to the conventional method, and the retina, cerebrum, cerebellum, brainstem, thymus, heart, lung, kidney, liver, spleen, muscle, small intestine, ovary and testis were harvested. RNA was purified using Trizol reagent (Thermo Fisher Scientific) according to the attached protocol. Then, 5 μL of formamide, 0.75 μL of MOPS buffer (pH 7.0) (0.4 M MOPS, 100 mM NaOAc and 20 mM EDTA-2Na) and 2 μL of formaldehyde were added to the RNA, and the mixture was heat-treated at 65° C. for 10 minutes, followed by rapid cooling for 2 minutes on ice to afford a sample for electrophoresis. The RNA was separated by electrophoresis (at 100 V for 135 minutes) on a 1% denaturing agarose gel in 5% MOPS buffer and 16.5% formaldehyde. MOPS served as a migration buffer. The RNA separated on the agarose gel was transferred to a nylon membrane (Pall) by capillary action with 20×SSC (Saline Sodium Citrate buffer), and the transferred RNA was heated at 80° C. for 2 hours to be fixed on the nylon membrane. The membrane was immersed in hybridization buffer (7% SDS, 50% formamide, 0.12 M sodium phosphate buffer (pH 7.2), and 0.25 M sodium chloride), and pre-hybridization was performed at 37° C. for 1 hour or longer. After completion of pre-hybridization, 60 ng of the probe prepared in the above section (1) of this Example and fragmented salmon sperm DNA at a final concentration of 100 μg/mL in the hybridization buffer were added to the membrane to perform hybridization at 43° C. overnight. After completion of the hybridization, the nylon membrane was washed with 2×SSC (Saline Sodium Citrate buffer)/0.1% SDS, and then with 0.1×SSC/0.1% SDS at 50° C. The nylon membrane was exposed to an X-ray film (FUJIFILM), and the X-ray film was developed with a film processor (FPM100, FUJIFILM).

Results

This Example revealed that the Klhl18 gene is specifically expressed in mouse retinal tissue (FIG. 1).

Example 2: Expression Analysis of Klhl18 Gene in Mouse Retina In Situ Hybridization (1) Preparation of Probe for In Situ Hybridization Analysis The pGEM-T-easy-Klhl18 plasmid prepared in Example 1 was treated with the restriction enzyme ApaI according to the conventional method to linearize the plasmid. A digoxigenin (DIG)-labeled antisense RNA strand was synthesized using the linearized DNA as a template with SP6 RNA Polymerase (GE Healthcare) according to the attached protocol. After completion of the synthesis of the antisense RNA strand, the linear DNA used as a template was degraded with RNase free DNase (GE Healthcare). The antisense RNA strand was purified by ethanol precipitation, dissolved in 50 μL of sterile water, and stored at −80° C.

(2) Hybridization

The retina of ICR mice of postnatal 9 days and 21 days (purchased from Oriental Yeast Co., Ltd.) were harvested according to the conventional method, and fixed in 4% paraformaldehyde/PBS (Phosphate Buffer Saline) at 4° C. overnight. The retina was washed with PBS and immersed in 30% sucrose/PBS to replace the 4% paraformaldehyde/PBS in the retina. The retina was then embedded in O.C.T. Compound (Sakura Finetek). Fresh frozen samples of the retina were embedded in O.C.T. Compound without the above fixing procedure.

Frozen retinal sections of 16 μm in thickness were prepared with a cryostat, mounted on glass slides, and dried at room temperature. The sections were treated with 4% paraformaldehyde/PBT (0.1% Tween 20 in PBS) for 15 minutes. The sections were washed with PBT, decolorized in 6% $H_2O_2$/PBT for 5 minutes and washed with PBT. The sections were treated with proteinase K (Roche)/PBT for 4 minutes and with 2 mg/mL glycine/PBT for 15 minutes to stop the reaction with proteinase K, and washed with PBT. The sections were post-fixed in 4% paraformaldehyde/0.2% glutaraldehyde/PBT for 15 minutes and washed with PBT. Pre-hybridization was performed with 50% formamide/5× SSC (Saline Sodium Citrate buffer) (pH 4.5)/50 μg yeast RNA/1% SDS at 70° C. for 1 hour. A hybridization solution containing 2 μg probe/50% formamide/5×SSC (Saline Sodium Citrate buffer) (pH 4.5)/50 μg yeast RNA/1% SDS was prepared using the probe prepared in the above section in this Example. After completion of pre-hybridization, the hybridization solution was applied to the sections to perform hybridization at 70° C. overnight.

(3) Color Development and Analysis

The sections were treated with 50% formamide/4×SSC (Saline Sodium Citrate buffer) (pH 4.5)/1% SDS at 70° C. for 15 minutes, and this procedure was repeated three times to wash the sections. The sections were treated with 50% formamide/2×SSC (pH 4.5) at 65° C. for 15 minutes, and this procedure was repeated three times to wash the sections. The sections were washed with 0.1% Tween 20/TBS and treated with 5% normal sheep serum/0.1% Tween 20/TBS for 1 hour. The sections were treated with an antibody reaction solution (anti-DIG antibody, 1% normal sheep serum, and 0.1% Tween 20 in TBS) at 4° C. overnight. The sections were washed with 0.1% Tween 20/TBS and NTMT (100 mM sodium chloride, 100 mM Tris-HCl (pH 9.5), 50 mM magnesium chloride, 0.1% Tween 20 and 2 mM levamisole), and were reacted with NBT/BCIP. After color development, the sections were washed with NTMT, and treated with PBT (pH 5.5) to stop the color development reaction. The sections were treated with 4% paraformaldehyde/0.1% glutaraldehyde/PBT for 10 minutes, washed with PBT, and sealed in mounting medium. The specimens were observed under an upright microscope equipped with a differential interference contrast objective lens.

Results

Figure 2:
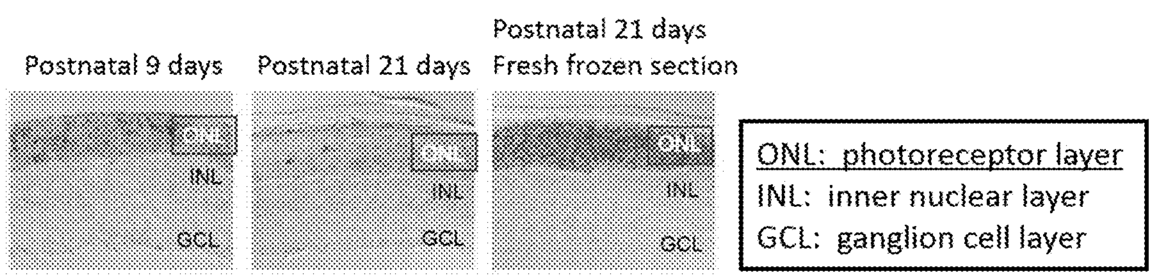
FIG. 2 shows the in situ hybridization analysis of the retinal region with expression of mouse Klhl18 RNA in the retinal sections of mice.

This Example revealed that the Klhl18 gene is specifically and strongly expressed in the retinal photoreceptor layer of mice of postnatal 9 days and 21 days (FIG. 2).

Example 3: Preparation of Klhl18 Gene-Deficient Mice (1) Establishment of ES Cell Line that are Heterozygous for Klhl18 Gene by Homologous Recombination The ES cell line JM8A3 from mice of C57BL/6N background was used as ES cells. ES cells were cultured in DMEM medium (Sigma) supplemented with inactivated fetal bovine serum (FBS), L-glutamine (GIBCO), MEM Non-Essential Amino Acids Solution (GIBCO), Na-pyruvate (GIBCO), penicillin (100 μg/mL)/streptomycin (100 μg/mL) (Nacalai Tesque), 2-mercaptoethanol (Nacalai Tesque), and LIF (CHEMICON). Mouse primary embryonic fibroblast cells having a neomycin-resistant transgene were treated with mitomycin C to arrest cell division and used as feeder cells. The Klhl18 KO vector (Clone name: PRPGS00036_C_D09) was purchased from KOMP (Knockout Mouse Project, USA). The Klhl18 KO vector was linearized by cleaving it with AsiSI (New England Biolabs), and the linearized DNA fragment was electroporated into the mouse ES cells at 240 V and 500 μF to introduce the targeting vector.

At 24 hours after the electroporation, the ES cells were cultured in medium containing 260 μg/mL G418 antibiotic (Nacalai Tesque) to select neomycin-resistant clones (ES cells into which the targeting vector was introduced). The ES cell colonies were harvested 8 to 10 days after the start of selection. The ES cell colonies were dissociated by treatment with 0.25% Trypsin/EDTA in a $CO_2$ incubator at 37° C. for 5 minutes. The cells were transferred to 96-well feeder plates and cultured to confluence. After the ES cells in the feeder plates reached 90% to 100% confluence, the cells were dissociated again with 0.25% Trypsin/EDTA. A portion of the cells was transferred to 96-well plates for DNA extraction, and the remaining portion of the ES cells were suspended in freezing medium (DMSO:FBS:ESDMEM+LIF (DMEM medium (Sigma) supplemented with L-glutamine (GIBCO), MEM Non-Essential Amino Acids Solution (GIBCO), Na-pyruvate (GIBCO), Penicillin (100 μg/mL)/Streptomycin (100 μg/mL) (Nacalai Tesque), 2-mercaptoethanol (Nacalai Tesque), LIF (CHEMICON) and FBS)=1:1:3), and frozen and stored at −80° C.

The ES cells were grown on the 96-well plate for DNA extraction until they reached 90% to 100% confluence, and the ES cells in each well were washed twice with PBS. Then, 50 μL of Lysis buffer (10 mM Tris (pH 7.5), 10 mM EDTA, 10 mM sodium chloride, 0.5% sarcosyl, and 200 μg/mL proteinase K) was added to each well, and the cells were incubated at 60° C. overnight. On the following day, 100 μL of 10 mM sodium chloride/ethanol was added to each well, and the cells were allowed to stand at 4° C. for 30 minutes or more without mixing. The supernatant was removed, and the DNA was washed with 70% ethanol. The DNA was air-dried and dissolved in 10-fold diluted TE containing RNase (20 μg/mL). Southern blotting was performed as described later on the genomic DNA of each clone as a sample to screen for heterozygous recombinants containing the mutant allele of interest resulted from homologous recombination.

The probe for Southern blotting was prepared as follows. For preparation of a 5'-probe, PCR was performed using the genomic DNA of ES cells as a template with 50 μM Forward 5' (SEQ ID NO: 60) as a forward primer and 50 μM Reverse 5' (SEQ ID NO: 61) as a reverse primer and Ex Taq (TaKaRa) according to the attached protocol. Similarly, for preparation of a 3'-probe, PCR was performed using the genomic DNA of ES cells as a template with 50 μM Forward 3' (SEQ ID NO: 62) as a forward primer and 50 μM Reverse 3' (SEQ ID NO: 63) as a reverse primer and Ex Taq (TaKaRa) according to the attached protocol. The PCR product was electrophoresed on a 1% agarose gel, and the bands of about 330 bp and about 536 bp detected on the gel were cut out and cloned into the T-EASY vector (Promega). The plasmid was digested with EcoRI (TaKaRa), and the digest (DNA) was subjected to electrophoresis on an agarose gel. The DNA fragments of 330 bp and 536 bp were each excised and the resulting DNA fragments were purified using glass beads. The purified DNA fragments were labeled with $^{32}$P dCTP and used for the following procedures.

Figure 3A:
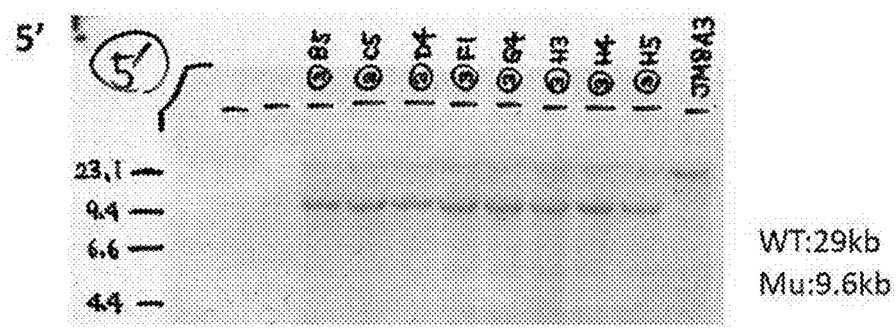
FIG. 3A shows the results of the Southern hybridization of the 5'-region in screening for ES cells for establishment of mouse Klhl18 gene-deficient mice.
Figure 3B:
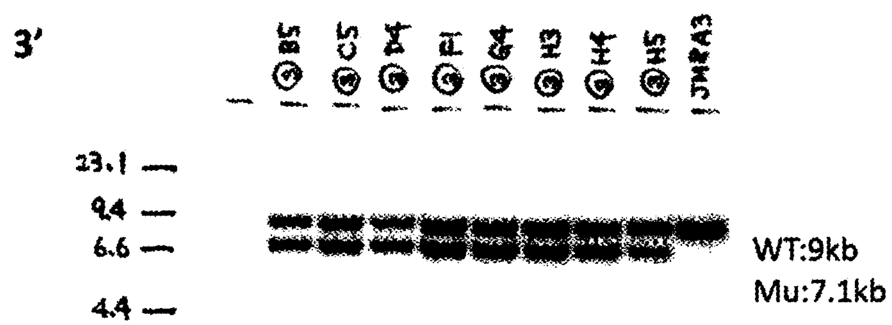
FIG. 3B shows the results of the Southern hybridization of the 3'-region in screening for ES cells for establishment of mouse Klhl18 gene-deficient mice.

The genomic DNA (10 μg) prepared from each clone was digested completely with the restriction enzyme KpnI (for confirmation of the 5' end of the homologous recombination region of the gene) or BamHI (for confirmation of the 3' end of the homologous recombination region of the gene), the digest was subjected to electrophoresis on a 0.8% agarose gel. The separated proteins were transferred from the gel to a nitrocellulose membrane (PALL), and hybridized with the 5'-probe or 3'-probe labeled with $^{32}$P as described above. The results of the hybridization detected by autoradiography are shown in FIGS. 3A and 3B. The detection of a 9.6 Kb fragment derived from the 29 Kb KpnI fragment of the wild-type allele reflects the successful introduction of the desired mutation. The detection of a 7.1 Kb fragment derived from the 9 Kb BamHI fragment of the wild-type allele reflects the successful introduction of the desired mutation. After Southern blotting, only a 29 Kb KpnI fragment and a 9 Kb BamHI fragment were detected in wild-type cells. In contrast, a 9.6 Kb KpnI fragment and a 7.1 Kb BamHI fragment were detected in the clones that were heterozygous for the Klhl18 gene (clone Nos. B5, C5, D4, F1, G4, H3, H4 and H5) resulting from homologous recombination (FIGS. 3A and 3B). The experiment confirmed that the clones were underwent the desired homologous recombination and the resulting ES cells were heterozygous for the Klhl18 gene.

(2) Preparation of Klhl18 Gene-Deficient Mice

One clone (clone No. C5) was selected from the ES cell clones that were heterozygous for the Klhl18 gene obtained by homologous recombination in the above section (1), and was injected into C57BL/6J mouse blastocysts to prepare chimeric mice. Briefly, one clone selected from the ES cell clones that were heterozygous for the Klhl18 gene obtained by homologous recombination was injected into C57BL/6J mouse blastocysts, and the blastocysts were transplanted into the uterus of foster mothers to prepare chimeric mice. The chimeric male mice were crossed with females of wild-type C57BL/6J mice to prepare primary (F1) mice. From these F1 mice, Klhl18f$^{flox/wt}$ mice were selected by Southern blotting. The F1 Klhl18f$^{flowx/wt}$ mice were crossed with CAG-Cre$^{+}$ mice (gifted from Institute of Resource Development and Analysis of Kumamoto University; MGI ID: MGI: 2176435) to prepare Klhl18$^{flox/wt}$ CAG-Cre$^{+/-}$ mice (hereinafter, called Klhl18 heterozygous KO mice). The Klhl18$^{flox/wt}$ CAG-Cre$^{+/-}$ mice were crossed with each other to prepare Klhl18$^{flox/flox}$ CAG-Cre$^{+/-}$ mice, which completely lacked the Klhl18 gene (hereinafter called Klhl18 KO mice).

Example 4: Determination of the Expression Level of Klhl18 Gene in Klhl18 KO Mice The Klhl18 KO mice prepared in Example 3 and wild-type mice were housed in a temperature-controlled room at 23° C., at a humidity of 55% with a 12 hour light and dark cycle until at the age of 12 weeks. The mice were dissected according to the conventional method to harvest the retina. One milliliter of Trizol reagent (Thermo Fisher Scientific) was added to the mouse retinal tissue, and the tissue was homogenized with a homogenizer. The homogenate was left to stand at room temperature for 5 minutes, and 200 μL of chloroform was added. The mixture was thoroughly vortexed and then left to stand at room temperature for 3 minutes. The supernatant was collected, and isopropanol in an equal volume to that of the supernatant was added, followed by centrifugation (at 14,000 rpm, at a radius of 5 cm, at 4° C. for 15 minutes) to precipitate RNA. The RNA was collected and suspended in 100 μL of sterile water. The RNA concentration of the RNA solution was measured with a spectrophotometer. Reverse transcription was performed using 2 μg of the RNA as a template with Super Script II (Invitrogen). PCR was performed using a 1 μL aliquot of 20 μL of the reverse transcript as a template with mouse Klhl18 gene primers (KO forward and KO reverse) and rTaq (PCR enzyme, TaKaRa) according to the attached protocol. Then, PCR was performed using mouse β-actin primers (forward primer (SEQ ID NO: 64); reverse primer (SEQ ID NO: 65)) according to the attached protocol. β-actin was used as a positive control.

Results

Figure 4:
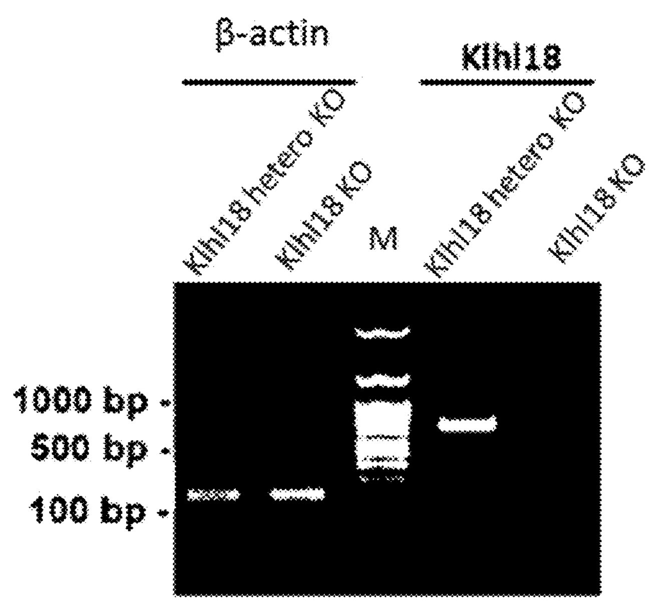
FIG. 4 shows the RT-PCR analysis showing disappearance of expression of the mouse Klhl18 gene in the retina of mouse Klhl18 gene-deficient mice.

This Example revealed that the expression of the Klhl18 gene was lost in the Klhl18 KO mice (FIG. 4).

Example 5: Effects of Klhl18 Gene Deficiency on Mouse Retinal Tissue

Toluidine Blue Staining

Retinal sections were prepared from one month old Klhl18 KO mice and wild-type (C57BL/6J strain) mice (purchased from Japan SLC) in the same manner as in Example 2 (2). The sections of mouse retina were washed with PBS and stained with 0.1% toluidine blue (Sigma)/PBS for 1 minute. The sections were washed three times with PBS, and the specimens were sealed in mounting medium. The specimens were observed under an upright microscope equipped with a differential interference contrast objective lens.

Results

Figure 5:
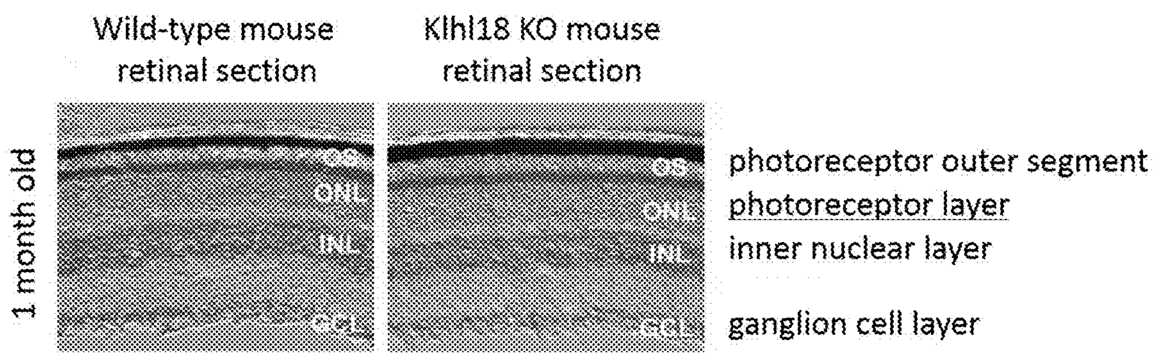
FIG. 5 shows toluidine blue staining of the retinal sections of wild-type mice and mouse Klhl18 gene-deficient mice.

This Example revealed that the deletion of the Klhl18 gene exhibited no effects on the cell layers (photoreceptor outer segment, photoreceptor layer, inner nuclear cell layer and ganglion cell layer) in the mouse retinal tissue (FIG. 5).

Example 6: Effects of Klhl18 Protein on Unc119 Protein as a Target

Western Blotting

Retinal tissue was harvested from one month old Klhl18 KO mice and wild-type (C57BL/6J strain) mice (purchased from Japan SLC) according to the conventional method. The retinal tissue was dissolved in 2× sample buffer (0.1 M Tris-HCl (pH 6.8), 1% SDS, 5% β-mercaptoethanol, 10% glycerol, and 0.02% BPB) and heat-treated at 100° C. for 5 minutes. SDS-PAGE was performed and the separated proteins on the gel were electrically transferred to a PVDF membrane (Merck Millipore) at 12 V for 90 minutes. The PVDF membrane was blocked with blocking solution (5% skim milk and 0.05% Tween 20/TBS) with shaking at room temperature for 1 hour. The PVDF membrane was reacted with a primary antibody diluted in the blocking solution at 4° C. overnight. The primary antibody was anti-Unc119 antibody (mouse monoclonal, a gift from Dr. Haeseleer (University of Washington, USA) (Haeseleer, 2008), 1:10 dilution) or α-Tublin antibody (mouse monoclonal, Sigma, 1:6,000 dilution). After completion of reaction with the primary antibody, the PVDF membrane was washed three times with 0.05% Tween 20/TBS with shaking at room temperature for 10 minutes. The PVDF membrane was reacted with a secondary antibody diluted in the blocking solution at room temperature for 1 hour. The secondary antibody was anti-mouse IgG (H+L) HRP-conjugated antibody (goat polyclonal, Zymed, 1:6,000 dilution). After completion of reaction with the secondary antibody, the PVDF membrane was again washed three times with 0.05% Tween 20/TBS with shaking at room temperature for minutes. The PVDF membrane was reacted with chemiluminescent reagent (Chemi-Lumi One (Nacalai Tesque)) or Pierce Western Blotting Substrate Plus (Thermo Fisher Scientific). The membrane was exposed to an X-ray film, and the protein of interest was detected using a film processor.

Results

Figure 6:
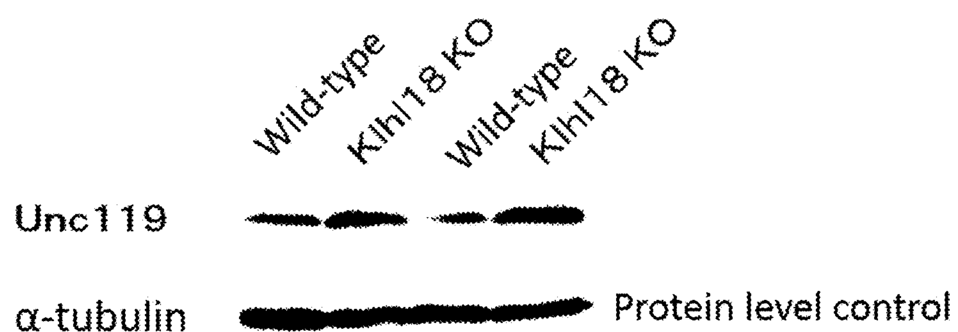
FIG. 6 shows the Western blot analysis of the amount of Unc119 protein in the retina of wild-type mice and mouse Klhl18 gene-deficient mice.

In this Example, a comparison between the bands from the wild-type and the bands from the Klhl18 KO protein revealed that the retinal ubiquitinating enzyme Klhl18 protein targets the Unc119 protein (FIG. 6). The amount of Unc119 protein increased due to the lack of ubiquitination in the retina of the Klhl18 KO mice (FIG. 6).

Example 7: Effects of Klhl18 Protein Deficiency on Visual Function

Electroretinogram (ERG) Recording

Figure 7A:
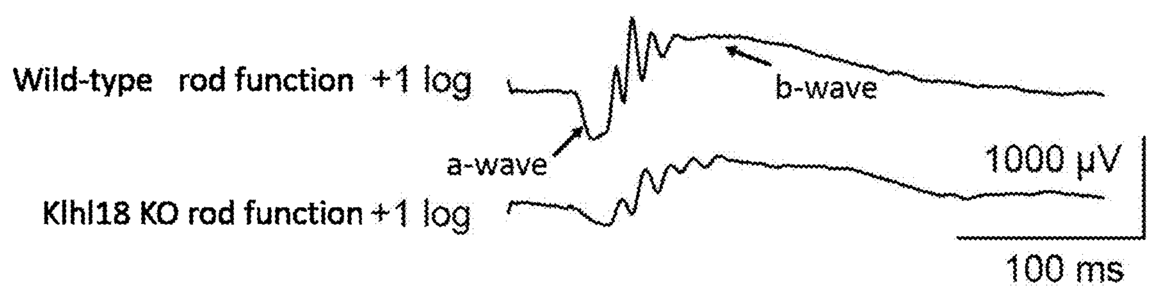
FIG. 7A shows the rod function of wild-type mice or Klhl18 KO mice under dark conditions as measured by electroretinography.
Figure 8A:
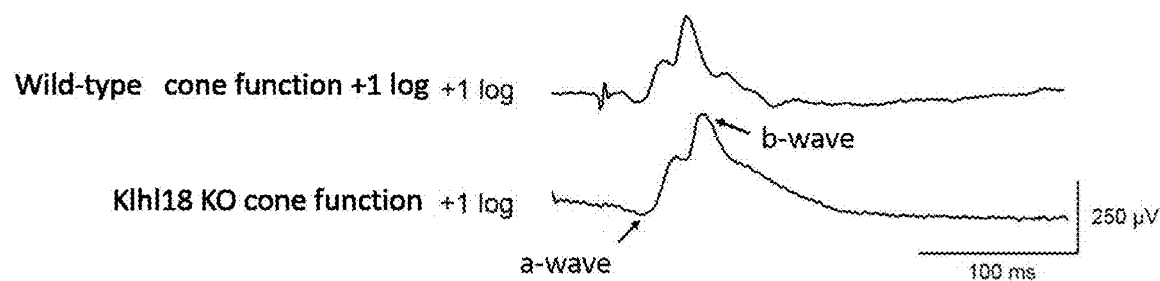
FIG. 8A shows the cone function of wild-type mice or Klhl18 KO mice under light conditions as measured by electroretinography.

Wild-type or Klhl18 KO mice of postnatal 2 months were light adapted or dark adapted. Light adaptation was performed at a light level of about 1000 lux for 1 hour or longer, and dark adaptation was performed by keeping the mice in a dark room for 4 hours or longer. Anesthesia was performed on dark-adapted or light-adapted mice with intraperitoneal injection of ketamine (100 mg/kg body weight per mouse) and xylazine (10 mg/kg body weight per mouse) in saline. Pupils were dilated with topical administration to the eyes with a mixture of 0.5% tropicamide and 0.5% phenylephrine HCl. ERG responses were measured with LED electrodes that emit a white flash (PuREC; Mayo Corporation). The mouse cornea was brought into contact with the electrodes, and stimulated with the stimulating flash using LED Visual Stimulator (LS-100, Mayo Corporation), and the ERG waves were recorded by TA-100 (Mayo Corporation) (FIGS. 7A and 8A). Strobe light stimulation with four levels of stimulus intensities ranging from −4.0 to 1.0 log cd−s/$m^2$ (−4.0, −3.0, −1.0 and 1 log cd−s/$m^2$) were used for the scotopic ERGs to measure the function of rod photoreceptor cells. Strobe light stimulation with four levels of stimulus intensities ranging from −0.5 to 1.0 log cd−s/$m^2$ (−0.5, 0, 0.5 and 1 log cd−s/$m^2$) were used for the photopic ERGs to measure the function of cone photoreceptor cells. From the wave data, a-waves and b-waves were quantified and expressed as the mean value±standard error. The photopic ERGs were recorded on a rod-suppressing white background of 1.3 log cd/$m^2$.

Results

Figure 7B:
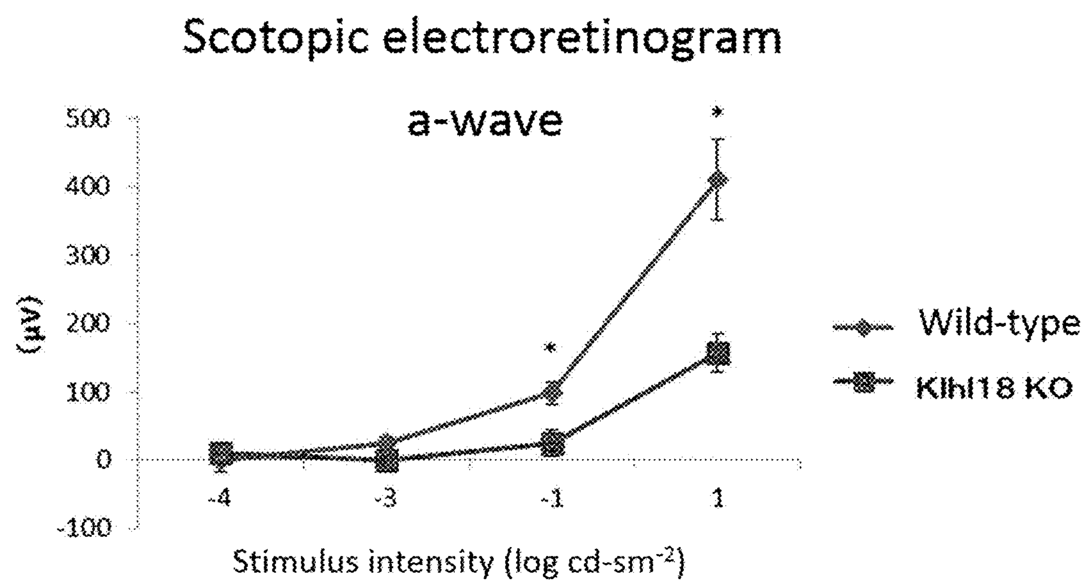
FIG. 7B is a chart showing the a-wave amplitudes at each stimulus intensity as measured by electroretinography in FIG. 7A.
Figure 7C:
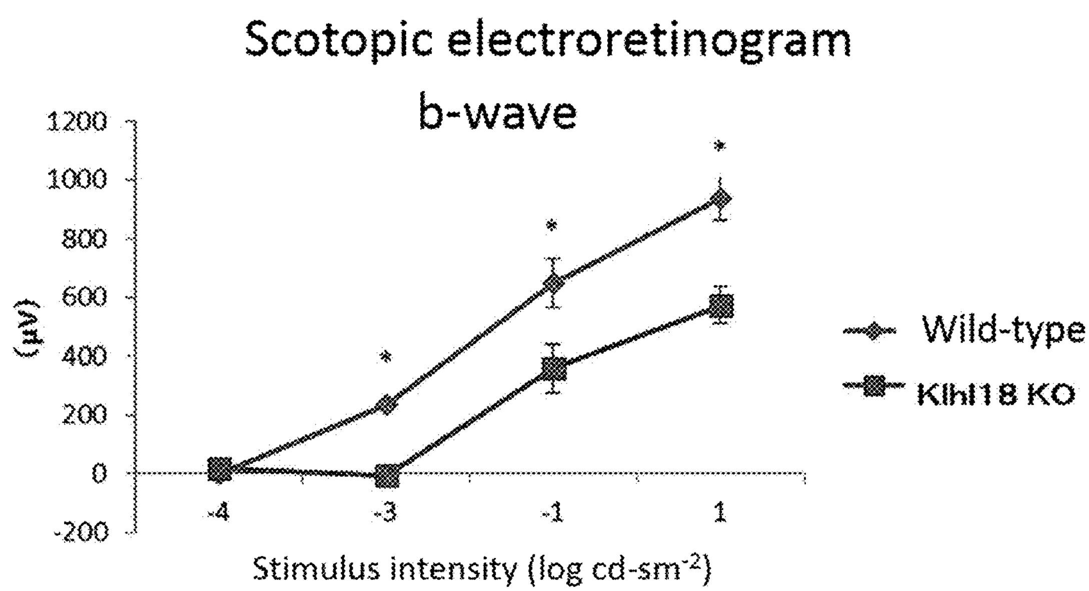
FIG. 7C is a chart showing the b-wave amplitudes at each stimulus intensity as measured by electroretinography in FIG. 7A.

This Example revealed that, under dark adaptation conditions, the amplitudes of a-waves and b-waves decreased in Klhl18 KO mice (FIGS. 7B and 7C). The Klhl18 KO mice manifested a weaker response to light stimulation than the wild-type mice in the dark place (mainly related to the function attributed to rod photoreceptor cells in the retina), indicating that the function of rod photoreceptor cells decreased (FIGS. 7A to 7C). These suggests that the overall photoreceptor cells in the retina were light-adapted due to the Klhl18 gene deficiency and the loss of the Klhl18 protein function in photoreceptor cells in the retina.

Figure 8B:
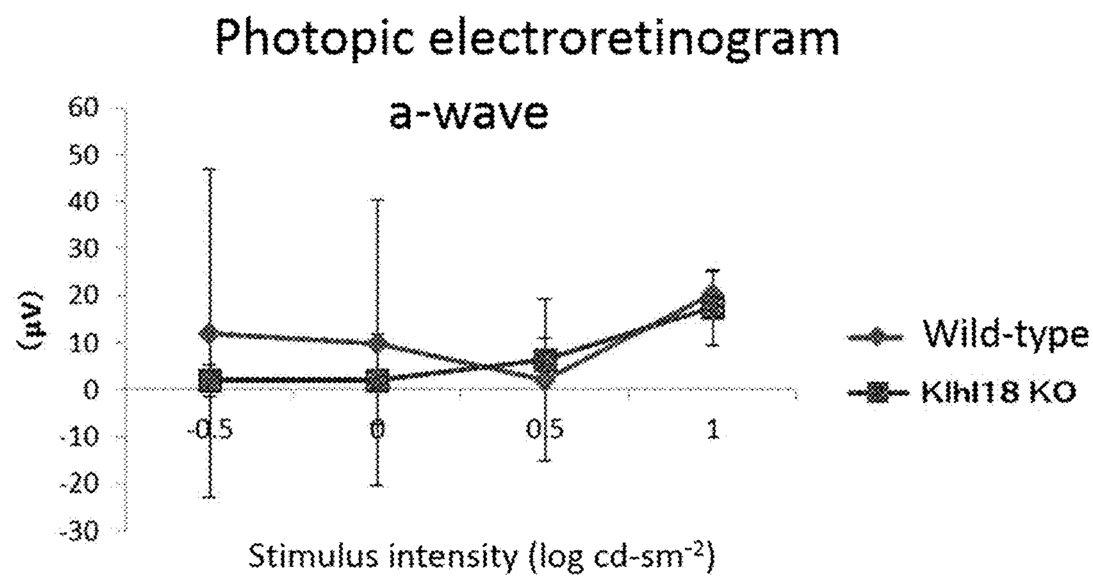
FIG. 8B is a chart showing the a-wave amplitudes at each stimulus intensity as measured by electroretinography in FIG. 8A.
Figure 8C:
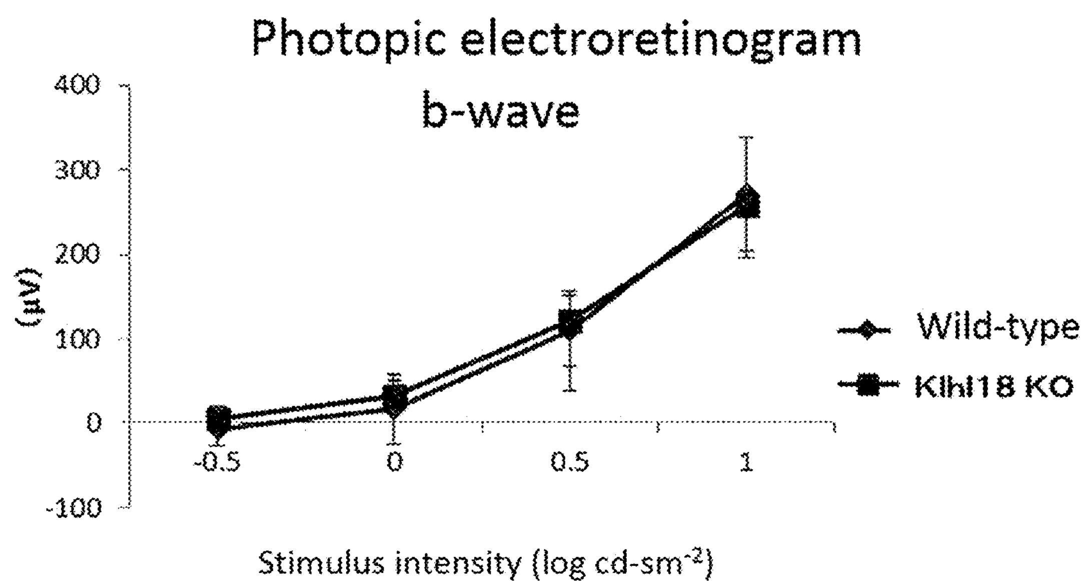
FIG. 8C is a chart showing the b-wave amplitudes at each stimulus intensity as measured by electroretinography in FIG. 8A.

In contrast, under light adaptation conditions, the amplitudes of a-waves and b-waves were normal in both wild-type mice and Klhl18 KO mice (FIGS. 8B and 8C). This indicated that, no differences were observed in the response to the light stimulus between the Klhl18 KO mice and the wild-type mice in a light place (mainly related to the function attributed to cone photoreceptor cells in the retina), and the function in a light place was normal (FIGS. 8A to 8C).

Example 8: Localization Analysis of the Light Signal Transduction Protein Transducin α in the Retina of Klhl18 KO Mice (1) Harvest of Mouse Retina Under Dark and Light Conditions Wild-type or Klhl18 KO mice of postnatal 2 months were light-adapted or dark-adapted. Light adaptation was performed at a light level of about 1000 lux for 1 hour or longer, and dark adaptation was performed by keeping the mice in a dark room for 4 hours or longer. The eyeballs in the light adaptation conditions were harvested at a light level of about 1000 lux, and the eyeballs in the dark adaptation conditions were harvested under a red lamp in a dark room. The eyeballs were fixed in 4% paraformaldehyde/PBS for 60 minutes to 90 minutes. The eyeballs were washed with PBS and embedded in O.C.T. Compound.

(2) Immunohistochemical Staining

The retina harvested under the above conditions was used to prepare the retinal sections of each mouse in the same manner as in Example 2 (2). The sections were washed twice with PBS and then blocked with blocking buffer (4% Normal donkey serum/0.1% Triton X-100/PBS) at room temperature for 1 hour. The sections were reacted with a primary antibody at 4° C. overnight. The sections were washed three times with PBS, and reacted with a secondary antibody at room temperature for 2 hours. The primary antibody was anti-GαT1 antibody (transducin, rabbit polyclonal, Santa Cruz, 1:500 dilution), and the secondary antibody was Alexa Flour 488-conjugated anti-rabbit antibody (Thermo Fisher Scientific, 1:500 dilution). After completion of the secondary antibody reaction, the sections were washed three times with PBS and sealed in mounting medium. All fluorescence images were taken under a confocal laser scanning microscope (LSM 700, Carl Zeiss).

Results

Figure 9:
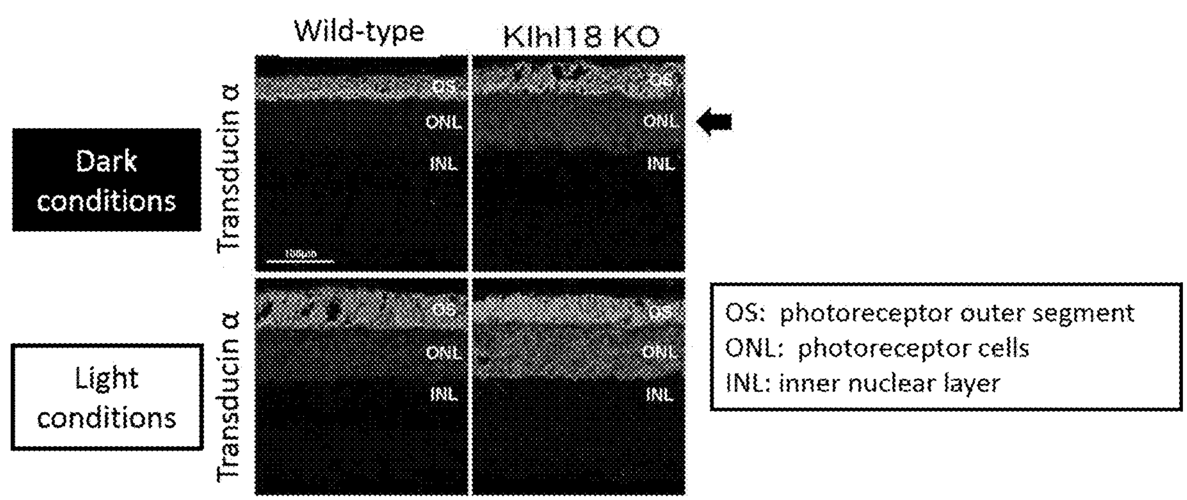
FIG. 9 shows the immunostaining of transducin α protein in the retina of wild-type mice or Klhl18 KO mice under dark or light conditions.

This Example confirmed that the light signal transduction protein transducin α in the retina of the Klhl18 KO mice was localized in the photoreceptor layer even under the dark conditions as compared with the retina of the wild-type mice (FIG. 9). Under light adaptation, transducin α subunit in photoreceptor cells of the retina is translocated from the outer segment to the cell body, leading to a decrease in light sensitivity. On the contrary, under dark adaptation, transducin α subunit is translocated from the cell body to the outer segment, leading to an increase in light sensitivity. Therefore, the results indicate that the retina of the Klhl18 KO mice were light-adapted in spite of the dark conditions.

Example 9: Experiment on Inhibition of Function of the Retinal Ubiquitinating Enzyme Klhl18 Protein: C-Terminal Fragment of Klhl18 Protein (1) Preparation of Plasmids pCAG-N-3× FLAG-Klhl18

The mouse Klhl18 gene contains a full-length open reading frame encoding a protein (574 residues), and the open reading frame was amplified by PCR using the pCMV-SPORT6-Klhl18 plasmid DNA (GenBank accession No. BC025563) (Open Biosystems) as a template with KOD-plus- (TOYOBO) according to the attached protocol. The primer sequences used for PCR were a forward primer (SEQ ID NO: 66) and a reverse primer (SEQ ID NO: 67). The amplified DNA fragment was treated with restriction enzymes ClaI (New England Biolabs) and NotI (TaKaRa). Similarly, the pCAG-N-3× FLAG plasmid (Omori et al., Proc Natl Acad Sci U.S.A. 107, 22671-22676, 2010) was treated with restriction enzymes ClaI and NotI. The restriction enzyme-treated DNA fragment and pCAG-N-3× FLAG plasmid were ligated using Ligation High Ver. 2 (TOYOBO) according to the attached protocol to prepare the FLAG-tagged full-length Klhl18 protein expression plasmid pCAG-N-3× FLAG-Klhl18.

pCAG-N-3× FLAG-C-Klhl18

The mouse Klhl18 gene contains an open reading frame encoding the C-terminal protein (298 residues at the C-terminal), and the open reading frame was amplified by PCR using the above FLAG-tagged Klhl18 expression plasmid pCAG-N-3× FLAG-Klhl18 as a template with KOD-plus-(TOYOBO) according to the attached protocol. The primer sequences used for PCR were a forward primer (SEQ ID NO: 68) and a reverse primer (SEQ ID NO: 69). The amplified DNA fragment was treated with restriction enzymes EcoRI (TaKaRa) and SalI (TaKaRa). Similarly, the pCAG-N-3× FLAG plasmid was treated with restriction enzymes EcoRI and XhoI (TOYOBO). The restriction enzyme-treated C-terminal protein fragment and pCAG-N-3× FLAG plasmid were ligated using Ligation High Ver. 2 (TOYOBO) according to the attached protocol to prepare the FLAG-tagged C-terminal Klhl18 protein expression plasmid pCAG-N-3× FLAG-C-Klhl18.

pCAG-N-2× HA-Unc119

The mouse Unc119 gene contains a full-length open reading frame encoding a protein (262 residues), and the open reading frame was amplified by PCR with KOD-plus-(TOYOBO) according to the attached protocol using cDNA prepared from the retina of adult C57BL/6N wild-type mice by the conventional method as a template. The primer sequences used for PCR were a forward primer (SEQ ID NO: 70) and a reverse primer (SEQ ID NO: 71). The amplified DNA fragment was treated with restriction enzymes XhoI (TOYOBO) and NotI. Similarly, the pCAG-N-2× HA plasmid was treated with restriction enzymes XhoI and NotI. The restriction enzyme-treated DNA fragment and the pCAG-N-2× HA plasmid were ligated using Ligation High Ver. 2 (TOYOBO) according to the attached protocol to prepare the HA-tagged Unc119 protein expression plasmid pCAG-N-2× HA-Unc119.

(2) Inhibition Experiment

The HEK293T cell line was cultured in DMEM (Wako Pure Chemical Industries) supplemented with antibiotics (penicillin (100 μg/mL)/streptomycin (100 μg/mL)) and 10% FBS at 37° C. under 5% $CO_2$. Introduction of the FLAG-tagged full-length Klhl18 protein expression plasmid and/or the FLAG-tagged C-terminal Klhl18 protein expression plasmid and/or the HA-tagged Unc119 protein expression plasmid into HEK293T cells was performed by the calcium phosphate method as conventionally applied. Specifically, the day before the introduction of the plasmids, the cells were re-seeded at a density of $1\times10^6$ cells in a 100 mm petri dish. The culture medium was replaced immediately before introduction of the plasmids. The plasmid DNAs each in a volume of 1 μg were mixed together in sterile water according to each combination, and 0.5 M calcium chloride (final concentration: 125 mM) was added to each of the resulting DNA solutions. Then, 2×BES (50 mM BES, 280 mM NaCl, and 1.5 mM $Na_2HPO_4.12H_2O$, pH 6.95) was added in an equal volume to that of the solution, and the mixture was vortexed. This mixture was added to the cells dropwise and the cells were cultured for 24 hours. The medium was replaced with fresh medium, and the cells were further cultured for 24 hours and harvested.

The cells were used for Western blotting in the same manner as in Example 6. The primary antibody was an anti-HA antibody (rat monoclonal, Roche, 1:10,000 dilution), and the secondary antibody was an anti-rat IgG (H+L) HRP-conjugated antibody (goat polyclonal, Zymed, 1:6,000 dilution).

Results

Figure 10:
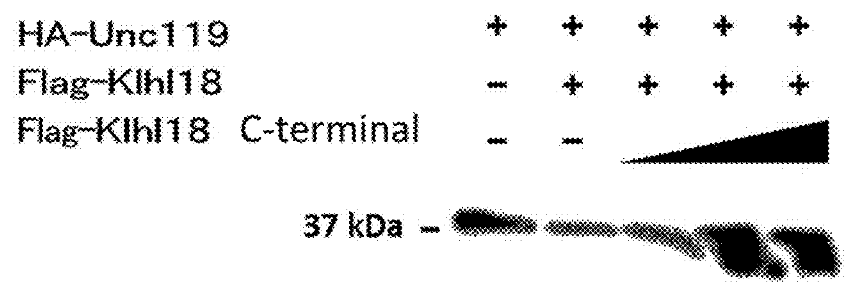
FIG. 10 shows the Western blot analysis of inhibitory effect on Klhl18 protein.

This Example confirmed that the C-terminal protein (C-terminal 298 residues) of the mouse Klhl18 gene inhibits degradation of the target protein Unc119 by the full-length Klhl18 protein (FIG. 10).

Example 10: Experiment of Inhibition of Function of the Retinal Ubiquitinating Enzyme Klhl18 Protein: Proteasome Inhibitor (MG-132)

The introduction of the pCAG-N-3× FLAG-Klhl18 plasmid and/or the pCAG-N-2× HA-Unc119 plasmid prepared in Example 9 into HEK293T cells was performed by the calcium phosphate method as conventionally applied. The proteasome inhibitor MG-132 (Merck Millipore) was prepared as a stock solution by dissolving it in DMSO (dimethyl sulfoxide) at a concentration of 10 mM. The medium was replaced with medium containing 0.1% MG-132 (final concentration: 10 μM) or medium containing 0.1% DMSO as a control, and 6 hours after the medium replacement, the cells were harvested. The cells were subjected to Western blotting in the same manner as in Example 9.

Further experiments were also performed on Neuro2a cells by the same experimental procedure.

Results

Figure 11:
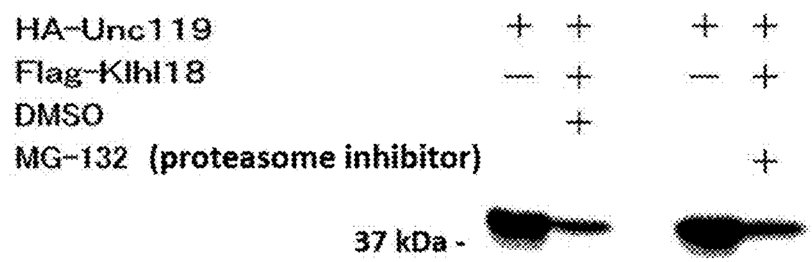
FIG. 11 shows the Western blot analysis of the inhibitory effect of MG-132 (proteasome inhibitor) on Klhl18 protein.

This Example confirmed that the proteasome inhibitor MG-132 inhibits degradation of the target protein Unc119 by the full-length Klhl18 protein (FIG. 11). Similar effects were confirmed in Neuro2a cells.

Example 11: Experiment 1 of Binding Analysis of Klhl18 and Unc119

(1) Preparation of Plasmids pCAG-N-3× FLAG-Unc119

A Unc119 cDNA fragment was excised from pCAG-N-2× HA-Unc119 prepared in Example 9 by treating the plasmid with restriction enzymes XhoI and NotI, and integrated into pCAG-N-2× HA plasmid treated with the restriction enzymes XhoI and NotI using Ligation High Ver. 2 (TOYOBO) to prepare the HA-tagged Unc119 expression plasmid pCAG-N-3× FLAG-Unc119.

pCAG-N-2× HA-Klhl18

A Klhl18 cDNA fragment was excised from pCAG-N-3× FLAG-Klhl18 prepared in Example 9 by treating the plasmid with restriction enzymes ClaI and NotI, and integrated into pCAG-N-2× HA plasmid treated with restriction enzymes ClaI and NotI using Ligation High Ver. 2 (TOYOBO) to prepare the FLAG-tagged full-length Klhl18 expression plasmid pCAG-N-2× HA-Klhl18.

(2) Immunoprecipitation

Immunoprecipitation was performed using pCAG-N-3× FLAG-Klhl18 and pCAG-N-2× HA-Unc119 prepared in Example 9 and pCAG-N-3× FLAG-Unc119 and pCAG-N-2× HA-Klhl18 prepared in Example 11. Anti-FLAG M2 Affinity Gel (Sigma) was used for immunoprecipitation. A combination of the Klhl18 expression plasmid pCAG-N-3× FLAG-Klhl18 and the Unc119 expression plasmid pCAG-N-2× HA-Unc119 were co-expressed in HEK293T cells, and a combination of the Klhl18 expression plasmid pCAG-N-2× HA-Klhl18 and the Unc119 expression plasmid pCAG-N-3× FLAG-Unc19 were co-expressed in HEK293T cells. The cells were lysed in Lysis buffer (TBS, 1% NP-40, 1 mM EDTA, 5 μg/μL Aprotinin, 2 μg/μL Leupeptin, 3 μg/μL Pepstatin A, and 1 mM PMSF), and centrifuged (at 14,000 rpm, at a radius of 5.4 cm, at 4° C. for 10 minutes). Anti-FLAG M2 Affinity Gel was added to the supernatant and the mixture was reacted at 4° C. overnight. FLAG peptide (Sigma) was used for elution of the precipitation. The immunoprecipitation samples were analyzed by Western blotting.

Results

Figure 12A:
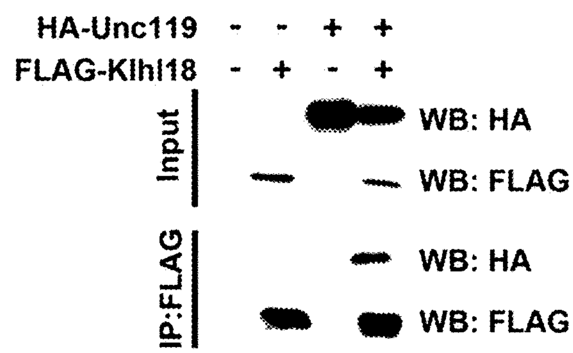
FIG. 12A shows the immunoprecipitation analysis of the interaction between HA-Unc119 protein and FLAG-Klhl18 protein.
Figure 12B:
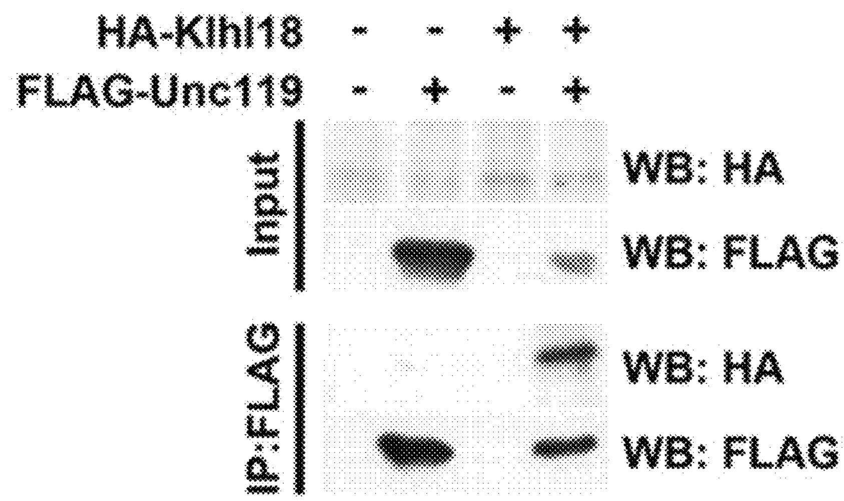
FIG. 12B shows the immunoprecipitation analysis of the interaction between HA-Klhl18 protein and FLAG-Unc119 protein.

This Example confirmed the interaction between pCAG-N-3× FLAG-Klhl18 and pCAG-N-2× HA-Unc119 (FIG. 12A). The experiments by switching the Flag tag and the HA tag confirmed the interaction between pCAG-N-3× FLAG-Unc119 and pCAG-N-2× HA-Klhl18 (FIG. 12B).

Example 12: Analysis of Ubiquitination of Unc119 Protein by Klhl18 Protein (1) Preparation of Plasmids pCAG-N-6× His-Ub The full-length open reading frame encoding mouse ubiquitin protein (76 residues) was amplified by PCR with KOD-plus- (TOYOBO) using cDNA prepared from the retina of adult C57BL/6 wild-type mice as a template. A forward primer (SEQ ID NO: 72) and a reverse primer (SEQ ID NO: 73) were used for PCR. The amplified DNA fragment was treated with restriction enzymes XhoI and NotI, and integrated into the pCAG-N-6× His plasmid treated with restriction enzymes XhoI and NotI using Ligation High Ver. 2 (TOYOBO) to prepare 6His-tagged ubiquitin protein expression plasmid pCAG-N-6× His-Ub.

pCAG-Klhl18-swap

The mouse Klhl18 gene contains a full-length open reading frame encoding a protein (574 residue), and the open reading frame was amplified by PCR with KOD-plus- (TOYOBO) using cDNA prepared from the retina of adult 129Sv/Ev wild-type mice as a template. A forward primer (SEQ ID NO: 74) and a reverse primer (SEQ ID NO: 75) were used for PCR. The amplified DNA fragment was integrated into the pCR-Blunt II plasmid using Ligation High Ver. 2 (TOYOBO) to prepare pCR-Blunt II-Klhl18-swap. Then, the pCR-Blunt II-Klhl18-swap plasmid and the pCAG-N-3× Flag-Klhl18 plasmid were treated with restriction enzymes XmaI and SacI, and genomic integration was used to replace the XmaI-SacI DNA fragment excised from pCAG-N-3× Flag-Klhl18 with the XmaI-SacI DNA fragment excised from pCR-Blunt II-Klhl18-swap using Ligation High Ver. 2 (TOYOBO) to prepare the Flag-tagged Klhl18 expression plasmid pCAG-N-3× Flag-Klhl18-swap.

PCR amplification was performed using primers with the sequences below with KOD-plus- (TOYOBO) using the pCAG-N-3× Flag-Klhl18-swap as a template. A forward primer (SEQ ID NO: 76) and a reverse primer (SEQ ID NO: 77) were used for PCR. The amplified DNA fragment was integrated into pCR-Blunt II using Ligation High Ver. 2 (TOYOBO) to prepare the pCR-Blunt II-Klhl18-N-terminal +Kozak plasmid. The pCR-Blunt II-Klhl18-N-terminal +Kozak plasmid was subjected to restriction enzyme treatment using EcoRI and Hind III, and the pCAG-N-3× Flag-Klhl18-swap plasmid was subjected to restriction enzyme treatment using Hind III and NotI to prepare DNA inserts. These DNA inserts were integrated into pCAGGSII (Omori et al., 2010) treated with restriction enzymes EcoRI and NotI using Ligation High Ver. 2 (TOYOBO) to prepare the untagged Klhl18 expression plasmid pCAG-Klhl18-swap.

(2) Ubiquitination Analysis Experiment

The pCAG-N-6× His-Ub plasmid, the pCAG-N-2× HA-Unc119 plasmid, and/or the pCAG-Klhl18-swap plasmid were introduced into Neuro2a cells according to the conventional method, and were allowed to express in the cells. The cells were lysed in Lysis buffer (20 mM Tris-HCl (pH 7.5), 0.5 M NaCl, 8 M Urea, and 5 mM imidazole), disrupted with a sonicator, and then centrifuged (at 14,000 rpm, at a radius of 5.4 cm, at 4° C. for 10 minutes). Ni-NTA-agarose beads (QIAGEN) were added to the supernatant and the mixture was reacted at 4° C. overnight. The precipitation was washed with Lysis buffer, and 2×SDS Sample buffer was added to prepare samples. The samples were analyzed by SDS-PAGE and Western blotting.

Results

Figure 13:
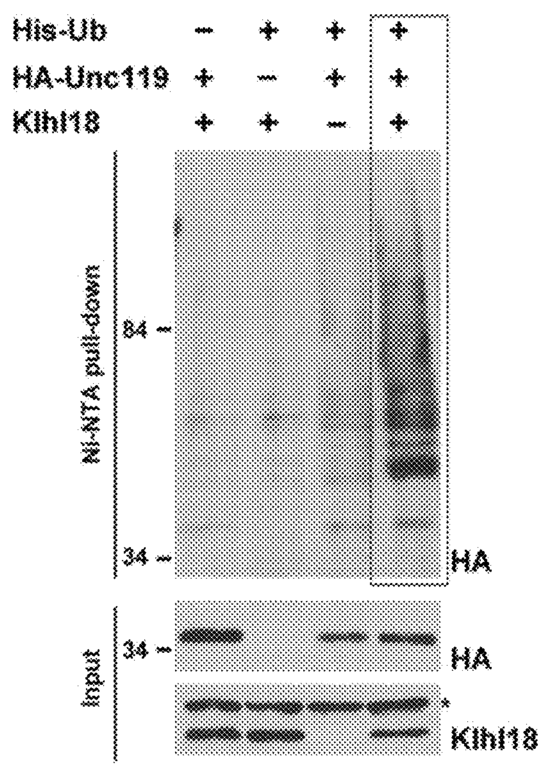
FIG. 13 shows the analysis of ubiquitination of HA-Unc119 protein by Klhl18 protein.

This Example confirmed that Klhl18 protein ubiquitinates Unc119 protein (FIG. 13).

Example 13: Experiment 2 of Binding Analysis of Klhl18 Protein and Unc119 Protein (1) Preparation of Plasmids pCAG-N-3× FLAG-N-Klhl18

The mouse Klhl18 gene contains an open reading frame encoding the N-terminal protein (N-terminal 276 residues), and the open reading frame was amplified by PCR with PrimeSTAR Max (Takara) using the above prepared pCAG-Klhl18-swap plasmid as a template. A forward primer (SEQ ID NO: 78) and a reverse primer (SEQ ID NO: 79) were used for PCR. The amplified DNA fragment was integrated into the pCAG-N-3× FLAG plasmid to prepare the FLAG-tagged N-terminal Klhl18 expression plasmid pCAG-N-3× FLAG-N-Klhl18.

(2) Immunoprecipitation

Immunoprecipitation was performed in the same manner as in Example 11 using the pCAG-N-2× HA-Unc119 plasmid and the pCAG-N-3× FLAG-C-Klhl18 plasmid prepared in Example 9 and the pCAG-N-3× FLAG-N-Klhl18 plasmid prepared in Example 13.

Results

This Example confirmed that Unc119 protein interacts with the full-length Klhl18 protein and the C-terminal region of the Klhl18 protein (FIG. 14). The results confirmed that interaction with Unc119 protein is mediated by the C-terminal region of Klhl18 protein.

Example 14: Experiment of Inhibition of Function of the Retinal Ubiquitinating Enzyme Klhl18 Protein: Nedd8-Activating Enzyme Inhibitor (MLN4924)

The pCAG-N-3× FLAG-Klhl18 plasmid and/or the pCAG-N-2× HA-Unc119 plasmid were introduced into HEK293T cells in the same manner as in Example 10. MLN4924 (Active Biochem) was dissolved in DMSO (Dimethyl Sulfoxide) to prepare a 100 μM stock solution. The medium containing 0.1% DMSO was replaced with medium containing the stock solution or DMSO so that the medium contained 0.3% MLN4924 stock solution (final concentration: 0.3 μM) or 0.3% DMSO (control) at 6 hours before harvest of the cells. The cells were harvested 6 hours post medium exchange. The cells were subjected to Western blotting in the same manner as in Example 9.

Results

This Example confirmed that the Nedd8-activating enzyme inhibitor MLN4924 inhibits degradation of the target Unc119 protein by the full-length Klhl18 protein (FIG. 15).

Example 15: In Vivo Electroporation (1) Preparation of Plasmids pCAGIG-N-3× FLAG-Unc119

The CAG promoter region and the N-3× FLAG-Unc119 region were obtained by treating pCAG-N-3× FLAG-Unc119 of Example 11 with restriction enzymes SalI and NotI, and were integrated into pCAGIG (Matsuda and Cepko, 2004) treated with restriction enzymes SalI and NotI using Ligation High Ver. to prepare the FLAG-tagged Unc119-IRES-EGFP expression plasmid (FIG. 16).

(2) In Vivo Electroporation

The pCAGIG-N-3× FLAG-Unc119 plasmid and the control pCAGIG plasmid was introduced into ICR mice of postnatal day 0 (PO) (purchased from Oriental Yeast Co., Ltd.). The mice were anesthetized with ice and the eyelid was excised with a 30-gauge injection needle (TERUMO) to make a small hole at the boundary between the cornea and the retina. A 33-gauge microsyringe (Ito Seisakusho) was inserted into the small hole, and 0.3 μL of DNA solution (5 μg/μL) was injected into the subretinal space. An electric pulse of 80 V and 50 ms was applied five times at intervals of 950 ms with an electrode according to the conventional method. The electroporated retina was harvested at 1 month of age and immunostained according to the conventional method.

Results

Figure 17:
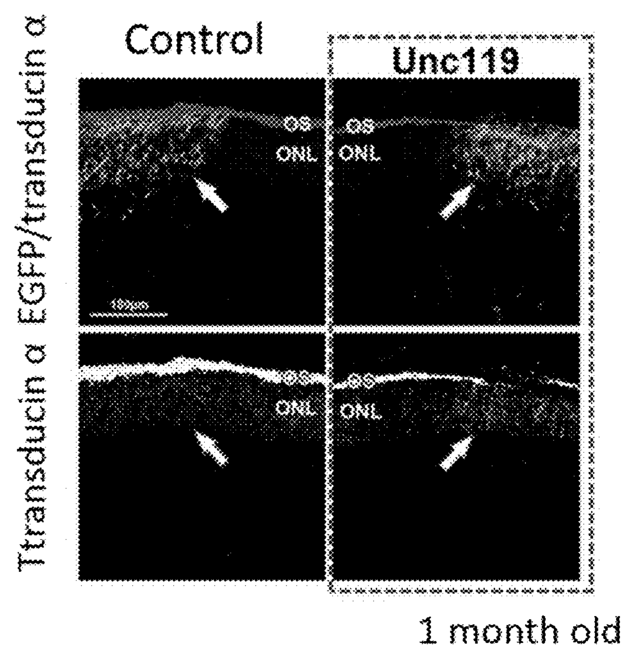
FIG. 17 shows the fluorescence immunostaining analysis of the localization of EGFP protein and transducin α protein in mouse retina after in vivo electroporation.

This Example confirmed that the signals of transducin α in the cell bodies increased in EGFP-positive photoreceptor cells in which Unc119 protein was overexpressed under the dark conditions (FIG. 17). The results suggested that the translocation of transducin α in Klhl18-deficient mice is induced by an excessive amount of Unc119.

Figure 18:
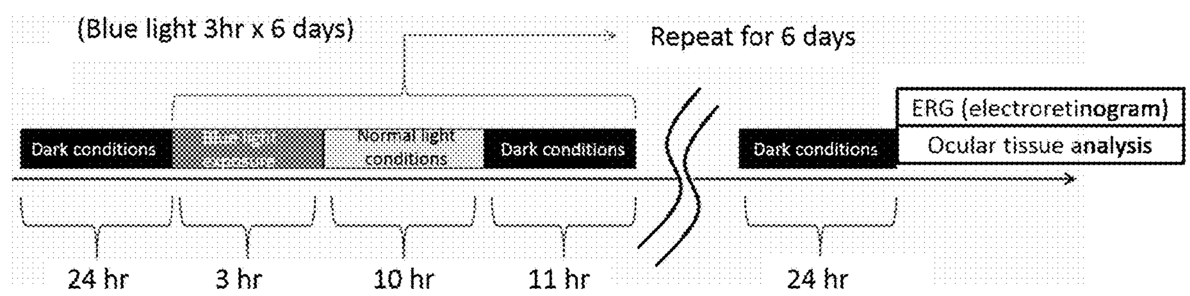
FIG. 18 is a schematic view showing the time schedule of a light-induced damage experiment.

Example 16: Experiment of Light-Induced Damage of Mouse Retina (1) Light-Induced Damage Adult mice (albino mice homozygous for Leu450 in the protein encoded by the Rpe65 gene, at an age of 4 to 5 weeks, generated by crossing Klhl18 KO mice with BALB/c mice (Japan SLC)) are kept under the dark conditions for about 24 hours to allow full dark adaption. The mydriatic agent Cyplegin (Santen Pharmaceutical Co., Ltd.) is administered to the eyes of the mice, and the mice are placed in a box with four mirrored walls and a mirrored floor. After 30 minutes, the mice are exposed to blue LED light. The wavelength of the light is about 450 nm, and the light reaching the mice is at about 7000 lux. The mice are exposed to the blue light for 3 hours and kept in the normal environment. From day 2, in the 12 hour light and dark cycle of room lighting, the mydriatic agent (Cyplegin) is administered to the mice after about 11 hours of the dark cycle, and 30 minutes later, the mice are exposed to blue light for 3 hours. The exposure to the blue light was repeated for 6 days in total. This time line is shown in FIG. 18. In the following day, ERG was recorded in the same manner as in Example 7.

Results

Figure 19:
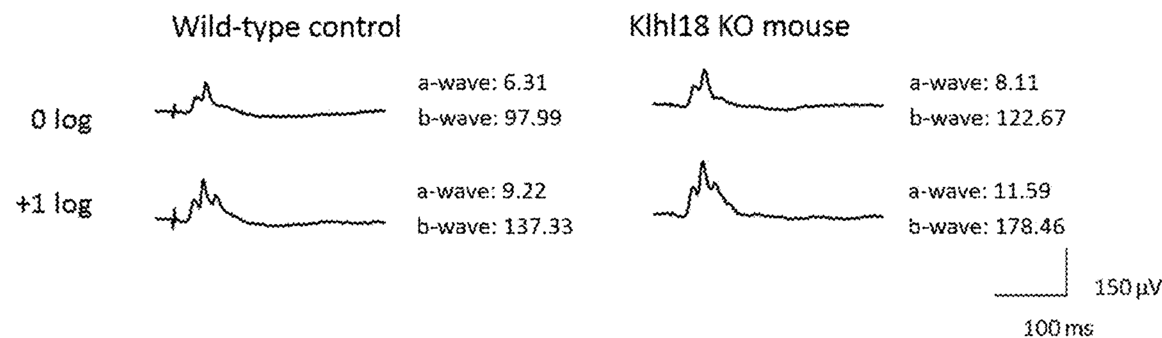
FIG. 19 shows the cone function of wild-type mice or Klhl18 KO mice after a light-induced damage experiment as measured by electroretinography.

In this Example, the electric amplitudes of the a-waves (photoreceptor cell activity) and the b-waves (bipolar cell activity) in the electroretinograms of Klhl18 KO mice with light-induced damage were higher than those in the wild-type control mice with light-induced damage (FIG. 19). These results support that the light-induced damage in photoreceptor cells is suppressed by deficiency or inhibition of Klhl18.

(2) Measurement of Thickness of Photoreceptor Layer by Roluidine Blue Staining

Retinal sections of wild-type control mice and Klhl18 KO mice with light-induced damage were prepared in the same manner as in Example 2 (2). The mouse retinal sections were used to measure the thickness of the photoreceptor layer in the same manner as in Example 5. Specifically, the sections were washed with PBS and stained with 0.1% toluidine blue (Sigma)/PBS for 1 minute. The sections were washed three times with PBS, and sealed in mounting medium. The sealed specimens were observed under an upright microscope equipped with a differential interference contrast objective lens. The thickness of the photoreceptor layer was determined by measuring the distance from the optic nerve.

Results

Figure 20:
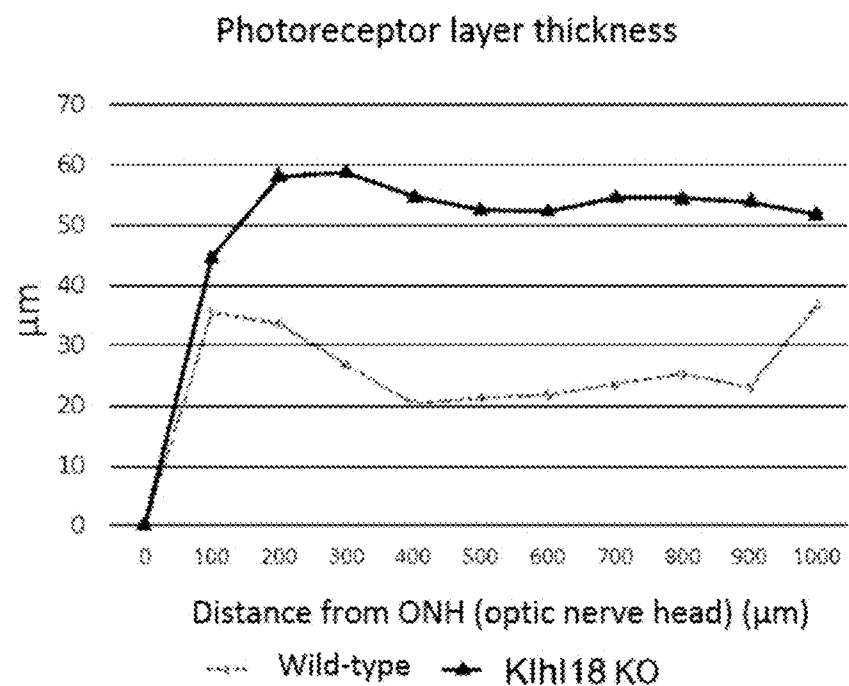
FIG. 20 shows the thickness of the retinal photoreceptor layer of wild-type mice or Klhl18 KO mice after a light-induced damage experiment.

The thickness of the photoreceptor layer was maintained better in the retina of the Klhl18 KO mice with light-induced damage as compared with that of the retina of the wild-type control mice with light-induced damage (FIG. 20). These results support that the degeneration of photoreceptor cells due to light-induced damage is suppressed by deficiency or inhibition of Klhl18.

(3) Fluorescent Immunostaining

Fluorescent immunostaining was performed using the mouse retinal sections. Specifically, the mouse retinal sections prepared in the same manner as in Example 2 (2) were washed twice with PBS, and blocked with blocking buffer (4% Normal donkey serum/0.1% Triton X-100/PBS) at room temperature for 1 hour. The sections were reacted with a primary antibody at 4° C. overnight. The sections were washed three times with PBS, and reacted with a secondary antibody at room temperature for 2 hours. The primary antibody was anti-Rhodopsin antibody (rhodopsin, rabbit polyclonal, Santa Cruz, 1:500 dilution) or anti-S-opsin antibody (S-opsin (blue cone opsin), goat polyclonal, Santa Cruz, 1:500 dilution). The secondary antibody was Alexa Flour 488-conjugated anti-rabbit antibody (Thermo Fisher Scientific, 1:500 dilution) or Cy3 antibody (Jackson ImmunoResearch Laboratories, 1:500 dilution). After completion of reaction with the secondary antibody, the specimens were washed three times with PBS and sealed in mounting medium. All fluorescence images were taken under a confocal laser scanning microscope (LSM 700, Carl Zeiss).

Results

Figure 21:
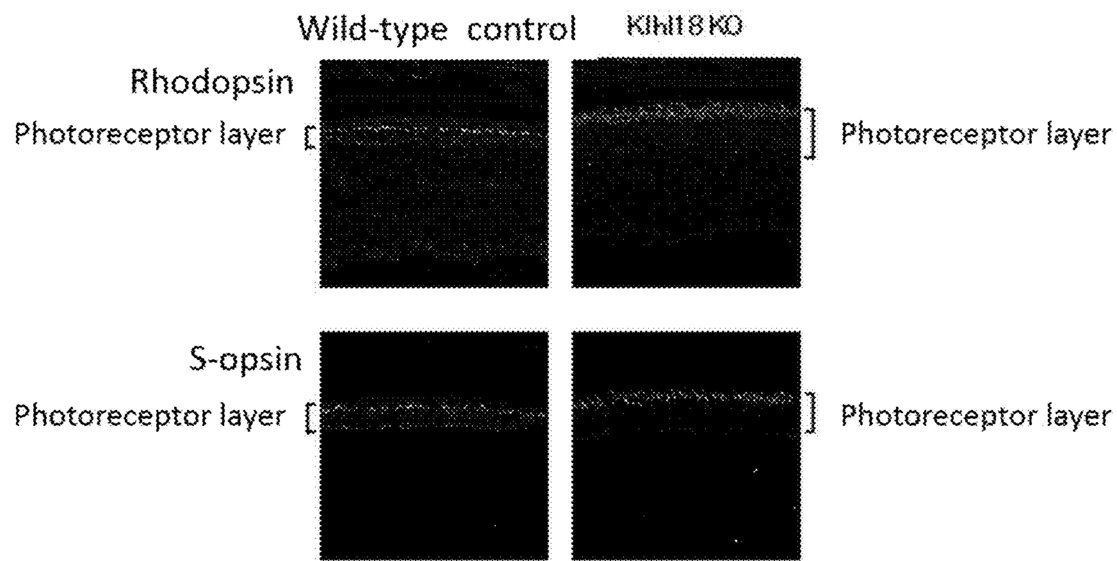
FIG. 21 shows the fluorescent immunostaining analysis of photoreceptor cell marker-positive cells in the retina of wild-type mice or Klhl18 KO mice after a light-induced damage experiment.

The fluorescence immunostaining analysis of the retina of Klhl18 KO mice with light-induced damage revealed that the signal intensities and thickness of rod photoreceptor cells (marker: rhodopsin) and cone photoreceptor cells (marker: S-opsin) were better retained as compared with those of the wild-type control mice with light-induced damage (FIG. 21). These results support that the degeneration of photoreceptor cells due to light-induced damage is suppressed by deficiency or inhibition of Klhl18, thereby maintaining photoreceptor cells.

Example 17: Analysis of Expression Level of Unc119 in Retina Under Light and Dark Conditions (1) Preparation of Anti-Mouse Unc119 Antibody (1-1) Preparation of Plasmids pGEX4T-1-Unc119

The antigenic site for the production of anti-mouse Unc119 antibody was amplified by PCR with PrimeSTAR Max DNA Polymerase (TaKaRa) using 129 Adult retina cDNA as a template. A forward primer (SEQ ID NO: 80) and a reverse primer (SEQ ID NO: 81) were used for PCR. The amplified DNA fragment was treated with restriction enzymes EcoRI and SalI, and then integrated into the pGEX4T-1 plasmid treated with restriction enzymes EcoRI and SalI, using Ligation High Ver. 2 to prepare the GST-tagged Unc119 expression plasmid pGEX4T-1-Unc119.

(1-2) Expression and Purification of GST-Tagged Unc119 Protein

*E. coli* BL21 (DE3) strain was transformed with the pGEX4T-1-Unc119 plasmid. The *E. coli* was pre-cultured in 100 mL of LB medium ($Amp^+$) overnight, and the *E. coli* culture medium was diluted with LB medium ($Amp^+$) so that the absorbance at $OD_{600}$ was about 0.2. The *E. coli* was grown in the culture medium so that the absorbance at $OD_{600}$ was around 0.6. IPTG was added to the medium at a final concentration of 1 mM at 25° C. for 3.5 hours to induce expression of GST-Unc119 protein.

BL21 (DE3) cells that were induced to express GST-Unc119 protein were disrupted by sonication in 0.1 M EDTA, 1% Triton X-100, 1 mM PMSF, 2 μg/ml Leupeptin, 5 μg/ml Aprotinin, 3 μg/ml Pepstatin A in PBS. After centrifugation (at 10,000 rpm, at a radius of 5.4 cm, at 4° C. for 10 minutes), the supernatant was adsorbed on Glutathione Sepharose™ 4B (GE Healthcare), and the resin was washed with 1% NP-40, 150 mM NaCl, 20 mM Tris (pH 7.4), 5 mM EDTA, 1 mM PMSF, 2 μg/ml Leupeptin, 5 μg/ml Aprotinin, and 3 μg/ml Pepstatin A. Elution from the resin was performed with 20 mM Glutathione/120 mM NaCl/100 mM Tris (pH 8.0) was used.

(1-3) Preparation of Anti-Mouse Unc119 Antibody

The purified antigen was injected into guinea pigs every two weeks, in total five times, according to the conventional method. One week after the final antigen injection, the blood was drawn to give an antiserum against Unc119.

(2) Harvest of Mouse Retinal Protein Under Dark and Light Conditions

Light adaptation was performed by keeping the mice at a light level of about 1,000 lux for about 4 hours, and dark adaptation was performed by keeping the mice in a dark room for about 4 hours. Retina was harvested from the eyeballs of wild-type mice and Klhl18 KO mice under the light and dark adaptation conditions, and lysed in Lysis buffer (TBS, 1% NP-40, 1 mM EDTA, 5 μg/μL Aprotinin, 2 μg/μL Leupeptin, 3 μg/μL Pepstatin A, 1 mM PMSF) by pipetting, and allowed to stand on ice for 30 minutes. After centrifugation (at 14,000 rpm, at a radius of 5.4 cm, at 4° C. for 10 minutes), the supernatant was recovered. Then, 2× sample buffer (0.1 M Tris-HCl (pH 6.8), 1% SDS, β-mercaptoethanol, glycerol and BPB) in an equal volume to that of the supernatant was added, and the mixture was allowed to stand at room temperature for 30 minutes.

(3) Western Blotting and Immunostaining Analysis

Western blotting was performed using the collected protein in the same manner as in Example 6. The anti-Unc119 antibody for Western blotting was diluted at 1:500 dilution.

Eyeballs were harvested from the wild-type mice and the Klhl18 KO mice under light and dark adaptation conditions, and allowed to stand in 4% PFA/PBS at room temperature for 30 minutes. The eyeballs were fixed, washed with PBS and immersed in 30% Sucrose/PBS overnight. All specimens were embedded in O.C.T. Compound, and the sections were prepared in the same manner as in Example 2 (2) and immunostained. The primary antibody was an anti-Unc119 antibody at 1:200 dilution.

Results

Figure 22A:
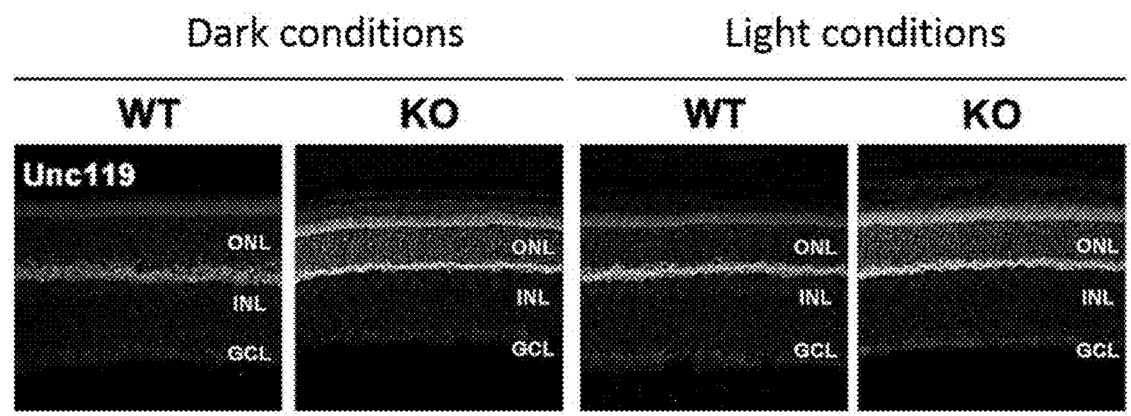
FIG. 22A shows the fluorescent immunostaining analysis of the expression level of Unc119 protein in the retina of wild-type mice or Klhl18 KO mice under dark and light conditions.
Figure 22B:
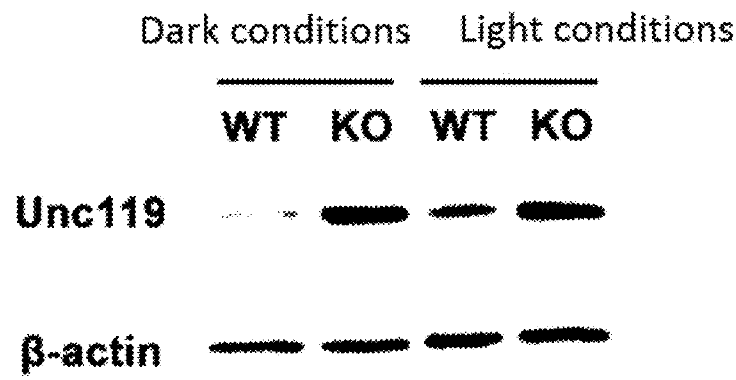
FIG. 22B shows the Western blot analysis of the expression level of Unc119 protein in the retina of wild-type mice or Klhl18 KO mice under light and dark conditions.

This Example confirmed that the amount of Unc119 protein in the retina of the wild-type mice under the light conditions was larger than that in the retina of the wild-type mice under the dark conditions (FIGS. 22A and 22B). The amount of Unc119 protein in the retina of the Klhl18 KO mice is larger than that in the retina of the wild-type mice under both light and dark conditions (FIGS. 22A and 22B). These results suggest that Klhl18 protein degrades Unc119 protein more efficiently under the dark conditions than under the light conditions.

Example 18: Effects of Klhl18 Protein Deficiency on Visual Function in RPE65 Gene-Deficient Mice (1) Preparation of RPE65 Gene-Deficient Mice RPE65-deficient mice were prepared using the CRISPR/Cas9 system. Two types of guide RNA sequences were designed to target the sequences in exon 2 and exon 3 of the mouse RPE65 gene by CRISPR/Cas9. Oligo DNAs containing the guide RNA sequences were prepared. RPE65 CRISPR-51 was mixed together with RPE65 CRISPR-31, and RPE65 CRISPR-52 was mixed together with RPE65 CRISPR-32, each in an equal amount (100 pg). The mixtures were heated at 65° C. for 10 minutes, allowed to stand at 20° C. for 30 minutes, and annealed to give double-stranded DNAs. The annealing was performed by integrating the DNAs into pX330 vector (Addgene) treated with BbsI (NEB) using Ligation High Ver. 2 kit (TOYOBO). The oligo DNAs containing the guide RNA sequences were DNAs of SEQ ID NOs: 82 to 85.

The prepared two types of plasmid DNAs were each adjusted to a concentration of 3 ng/μL in saline (6 ng/μL in total), then introduced into a glass capillary (G-1.2, Narishige) whose tip was sharpened into a needle-shape with a micropipette puller (P-97/IVF, Stutter), and injected into the pronucleus of fertilized eggs of BDF1 mice (offspring generated by crossing C57BL/6N females with DBA2 males, Japan SLC) using an manipulator (TransferMan NK2, Eppendorf) under an inverted microscope (AxioVert200, Zeiss). The fertilized eggs were transplanted into the oviduct of pseudo-pregnant female mice (ICR mice, SLC). Animals harboring nucleotide deletion mutations in the DNA sequence of the RPE65 gene were selected from the offspring by sequencing to give RPE65 heterozygous-deficient mice. RPE65 heterozygous-deficient mice were crossed with each other to generate RPE65-completely deficient mice (referred to as RPE65 KO mice).

(2) Preparation of RPE65 and Klhl18 Double-Deficient Mice

The RPE65 KO mice generated above were crossed with the Klhl18 KO mice prepared in Example 3 to generate mice heterozygously deficient for the RPE65 gene and the Klhl18 gene. Mice heterozygously deficient for the RPE65 gene and the Klhl18 gene were crossed with each other to generate mice completely deficient for the RPE65 gene and the Klhl18 gene (referred to as double KO mice).

(3) Electroretinogram (ERG) Recording

Mice were light-adapted or dark-adapted and ERG was recorded in the same manner as in Example 7 except that using the RPE65 deficient mice or double KO mice of postnatal 6 months.

Results

Figure 23:
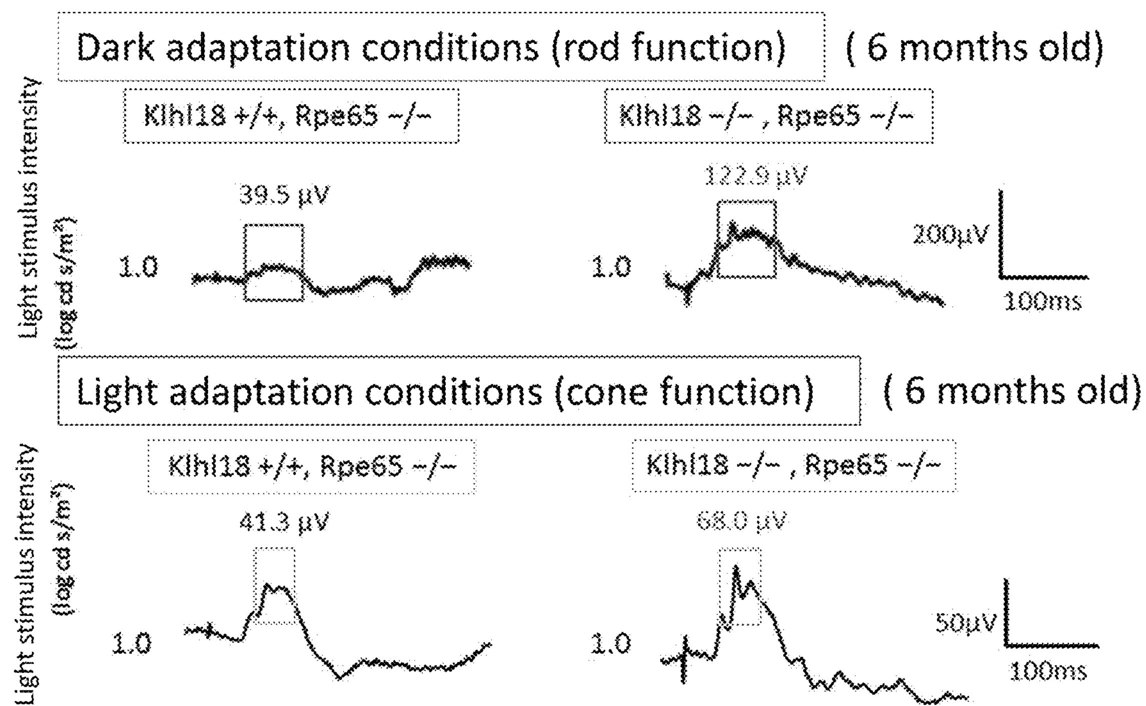
FIG. 23 shows the effects of Klhl18 protein deficiency in RPE65 gene-deficient mice as measured by electroretinography.

The results revealed that the electric amplitudes in the electroretinograms of the double KO mice were higher than those in the RPE65-deficient mice in both dark conditions and light conditions (FIG. 23). These results suggest that the degeneration of retinal photoreceptor cells in RPE65-deficient mice is suppressed by deficiency of Klhl18, and deficiency or inhibition of Klhl18 is effective for ameliorating or preventing hereditary retinitis pigmentosa.

Example 19: Experiment of Light-Induced Damage in Mice that Received Inhibitor of Activity of Ubiquitination Complex Protein MLN4924 (Chemscene) (60 mg/kg) was subcutaneously injected into the back of 4-weeks-old BALB/c mice (Japan SLC) that were kept in a dark place for 7 hours to be adapted to darkness. Four hours later, the mice were placed in a box with four mirrored walls and a mirrored floor, and exposed to blue LED light. The wavelength of the light was about 450 nm, and the light reaching the mice was at about 7000 lux. After three hours of exposure to the blue light, the mice were kept in the normal environment for 10 hours. This cycle was repeated for three days. Four days after the final exposure to the blue light, electroretinogram (ERG) recording and tissue analysis by retinal dissection were performed in the same manner as in Example 16. As a control, mice treated with DMSO were used.

Results

Figure 24:
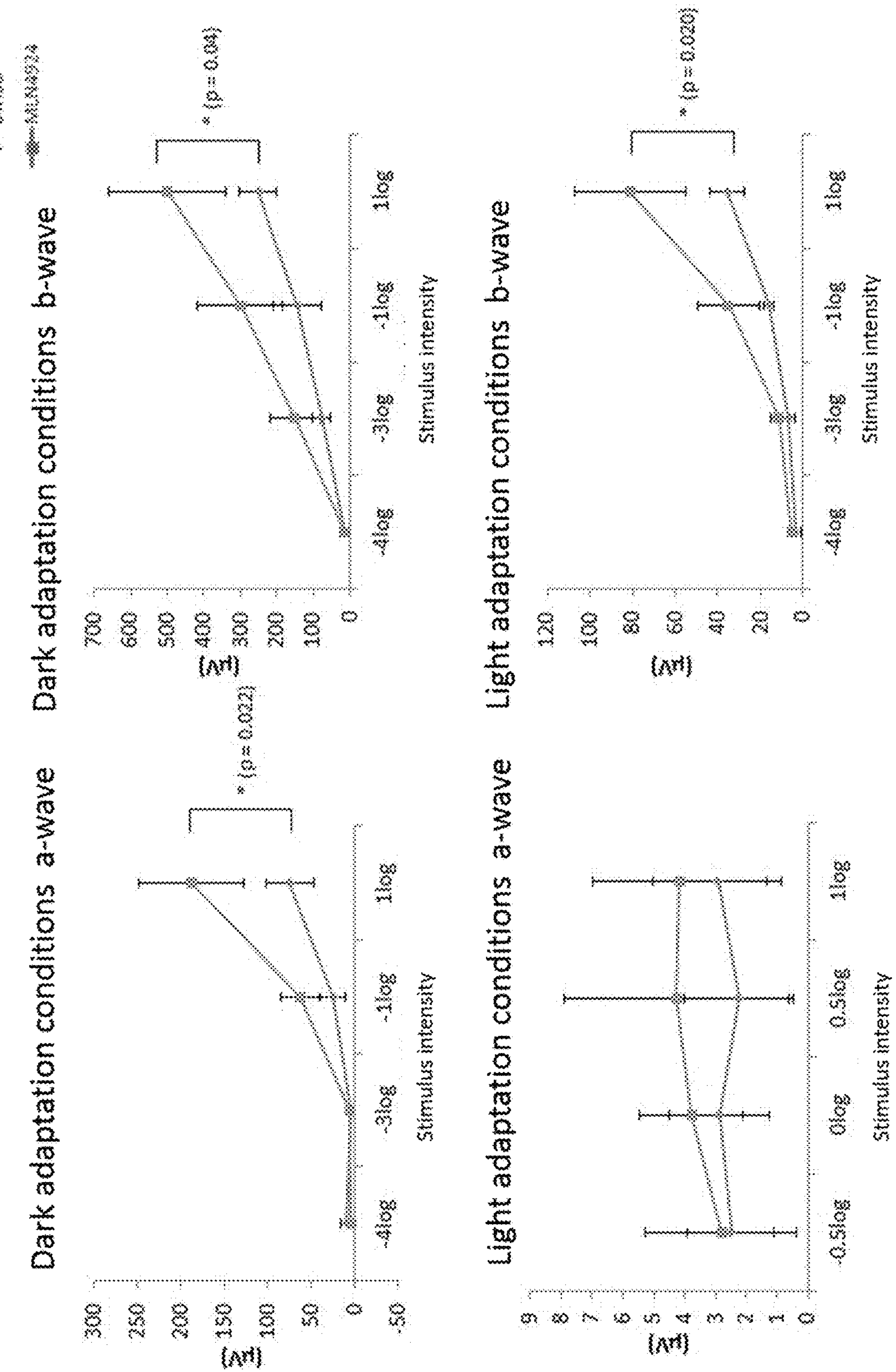
FIG. 24 shows the results of electroretinography in mice that received MLN4924 (an inhibitor of Nedd8-activating enzyme).

The results revealed that the electric amplitudes of the a-waves (photoreceptor cell activity) and b-waves (bipolar cell activity) in the mice that received MLN4924 were higher than those in the control mice (FIG. 24). These results indicate that administration of MLN4924 inhibits deterioration in the physiological function of the retina due to light-induced damage.

Figure 25:
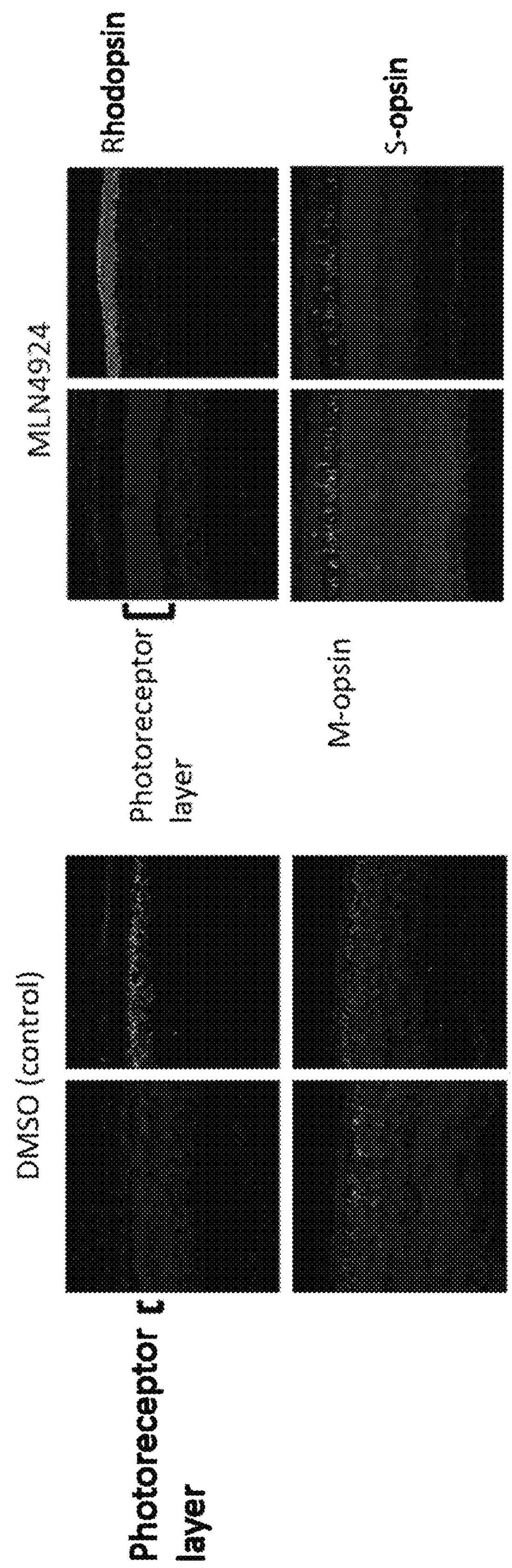
FIG. 25 shows the fluorescent immunostaining analysis of the retina of mice that received MLN4924 (an inhibitor of Nedd8-activating enzyme).

Fluorescence immunostaining analysis of the retina revealed that the signal intensities and thickness of rod photoreceptor cells (marker: rhodopsin) and cone photoreceptor cells (markers: S-opsin and M-opsin) in mice that received MLN4924 were better retained as compared with those in the control mice (FIG. 25). These results support that the administration of MLN4924 inhibits the degeneration of photoreceptor cells due to light-induced damage and maintains photoreceptor cells.

Figure 26:
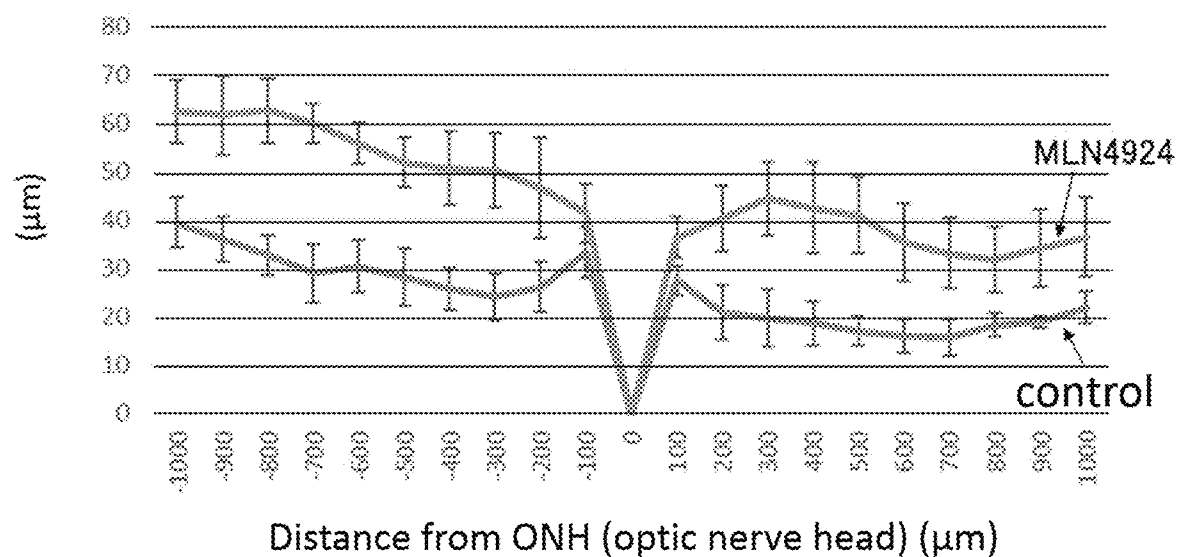
FIG. 26 shows the thickness of the retinal photoreceptor layer in mice that received MLN4924 (an inhibitor of Nedd8-activating enzyme).

The thickness of the photoreceptor layer in the retina of the mice that received MLN4924 was better maintained as compared with that of the control mice (FIG. 26). These results support that the administration of MLN4924 inhibits the degeneration of photoreceptor cells due to light-induced damage.

The invention claimed is:

1. A method for inhibiting or reducing light sensitivity of a retina, the method comprising administering to an animal a substance that inhibits or reduces Kelch-like 18 (Klhl18), wherein the substance is MLN4924 or the C terminal fragment of Klhl18, wherein the C-terminal fragment is the C-terminal 298 residues of Klhl18.

2. The method according to claim 1, wherein the method is provided to an animal in need of protection of a retina, inhibition of retinal degeneration and/or reduction in hyperesthesia.

3. The method according to claim 1, wherein the method is provided to an animal in need of an amelioration or prevention of a symptom associated with light reception, wherein the symptom associated with light reception is at least one selected from the group consisting of age-related macular degeneration, retinitis pigmentosa, Leber congenital amaurosis, Stargardt disease, cone-rod dystrophy and light-induced damage.

4. The method according to claim 1, wherein the Klhl18 is a protein consisting of the amino acid sequence of SEQ ID NO: 3 or 12.

5. The method according to claim 1, wherein the substance that inhibits or reduces Klhl18 is a substance that inhibits or reduces the expression and/or activity of Klhl18, or a substance that inhibits the activity of a protein component of a Klhl18 complex.

6. The method according to claim 1, wherein the substance is administered in the form of an injection or an eye drop.

* * * * *